(12) United States Patent
Lee et al.

(10) Patent No.: US 12,116,458 B2
(45) Date of Patent: Oct. 15, 2024

(54) CATIONIC POLYMER WITH ALKYL SIDE CHAINS AND USE FOR BIOMOLECULE DELIVERY

(71) Applicant: GenEdit, Inc., South San Francisco, CA (US)

(72) Inventors: Kunwoo Lee, South San Francisco, CA (US); Santanu Maity, South San Francisco, CA (US)

(73) Assignee: GenEdit Inc.

( * ) Notice: Subject to any disclaimer, the term of this patent is extended or adjusted under 35 U.S.C. 154(b) by 672 days.

(21) Appl. No.: 17/287,978

(22) PCT Filed: Oct. 24, 2019

(86) PCT No.: PCT/US2019/057959
§ 371 (c)(1),
(2) Date: Apr. 22, 2021

(87) PCT Pub. No.: WO2020/086910
PCT Pub. Date: Apr. 30, 2020

(65) Prior Publication Data
US 2021/0371590 A1    Dec. 2, 2021

Related U.S. Application Data

(60) Provisional application No. 62/750,123, filed on Oct. 24, 2018.

(51) Int. Cl.
*C08G 69/10*     (2006.01)
*A61K 47/59*     (2017.01)
*C08G 69/48*     (2006.01)

(52) U.S. Cl.
CPC ............ *C08G 69/10* (2013.01); *A61K 47/595* (2017.08); *C08G 69/48* (2013.01)

(58) Field of Classification Search
CPC ........ C08G 69/10; C08G 69/48; C08G 69/08; C08G 69/14; A61K 47/595; C09J 177/02; A61L 24/00; A61L 24/06; C08L 77/02
See application file for complete search history.

(56) References Cited

U.S. PATENT DOCUMENTS 5,516,758 A *  5/1996  Stevens ............... C08G 73/1092
                                                     514/357
2017/0362609 A1 * 12/2017 Ghoroghchian ......... C07K 2/00

FOREIGN PATENT DOCUMENTS

EP           2 399 948 A1    12/2011

OTHER PUBLICATIONS

International Search Report and Written Opinion issued in PCT/US2019/057959 mailed Feb. 17, 2020 (19 pages).
Itaka K. et al., "Biodegradable polyamino acid-based polycations as safe and effective gene carrier minimizing cumulative toxicity", *Biomaterials*, Elsevier Science Publishers BV., Barking, GB, vol. 31, No. 13, pp. 3707-3714 (2010).

* cited by examiner

*Primary Examiner* — Shane Fang
(74) *Attorney, Agent, or Firm* — Leydig, Voit & Mayer, Ltd.

(57) ABSTRACT

Provided is a polymer comprising a structure of Formula 1 or Formula 3 as provided herein, as well as a method of making the same; a composition comprising the polymer and a nucleic acid and/or polypeptide; and a method of delivering a nucleic acid and/or polypeptide to a cell.

20 Claims, 12 Drawing Sheets

Specification includes a Sequence Listing.

```
Streptococcus pyogenes Cas9
Genbank AKP81606

1 mdkkysigld igtnsvgwav itddykvpsk kfkvlgntdr hsikknliga llfdsgetae        [Motif 1]
  61 atrlkrtarr rytrkrnric ylgeifsnem akvddsffhr leesflveed kkherhpifg      Domain 1
 121 nivdevayhe kyptiyhlrk klvdstdkad lrliylalah mikfrghfli egdlnpdnsd
 181 vdklfiqlvq tynqlfeenp inasgvdaka ilsarlsksr rlenliaqlp gekknslfgn
 241 lialslgltp nfksnfdlae daklqlskdt ydddldnlla qigdqyadlf laaknlsdai
 301 llsdilrvnt eitkaplsas mikrydehhq dltllkalvr qqlpekykei ffdqskngya
 361 qyidgqasqe efykfikpil ekmdgteell vklnredllr kqrtfdnqsi phqihlgelh
 421 ailrrqedfy pflkdnreki ekiltfripy yvgplargns rfawmtrkse etitpwnfee
 481 vvdkgasaqs fiermtnfdk nlpnekvlpk hsllyeyftv yneltkvkyv tegmrkpafl
 541 sgeqkkaivd llfktnrkvt vkqlkedyfk kiecfdsvei sgvedrfnas lgtyhdllki
 601 ikdkdfldne enediediv ltltlfedre mieerlktya hlfddkvmkq lkrrrytgwg
 661 rlsrklingi rdkqsgktil dflksdgfan rnfmqlihdd sltfkediqk aqvsgqgdsl
 721 hehianlags paikgilqt vkvvdelvkv mgrhkpenIv lemarehqtt qkgqknsrer    [Motif 2]
 781 mkrieegike lgsqilkehp ventqlqnek lylyylqngr dmyvdqeldi nrlsdydvdh    [Motif 3]
 841 ivpqsflkdd sidnkvltrs dknrgksdnv pseevvkkmk nywrqllnak litqrkfdnl    Domain 2
 901 tkaergglse ldkagfikrq lvetrqitkh vaqildsrmn tkydendkli revkvitlks
 961 klvsdfrkdf qfykvreinn yhhaydayln avvgtalikk ypklesefvy gdykvydvrk   [Motif 4]
1021 miakseqeig katakyffys nimnffktei tlangeirkr plietngetg eivwdkgrdf
1081 atvrkvlsmp qvnivkktev qtggfskesi lpkrnsdkli arkkdwdpkk yggfdsptva
1141 ysvlvvakve kgkskklksv kellgitime rssfeknpid fleakgykev kkdliiklpk
1201 yslfelengr krmlasagel qkgnelalps kyvnflylas hyeklkgspe dneqkqlfve
1261 qhkhyldeii eqisefskrv iladanldkv lsaynkhrdk pireqaenii hlftltnlga
1321 paafkyfdtt idrkrytstk svldatlihq sitglyetri dlsqlggd
```

*Streptococcus pyogenes* Cas9
Genbank AKP81606

```
   1 mdkkysigld igtnsvgwav itddykvpsk kfkvlgntdr hsikknliga llfdsgetae
  61 atrlkrtarr rytrrknric ylgeifsnem akvddsffhr leesflveed kkherhpifg
 121 nivdevayhe kyptiyhlrk klvdstdkad lrliylalah mikfrghfli egdlnpdnsd
 181 vdklfiqlvq tynqlfeenp inasgvdaka ilsarlsksr rlenliaqlp gekknslfgn
 241 lialslgltp nfksnfdlae daklqlskdt ydddldnlla qigdqyadlf laaknlsdai
 301 llsdilrvnt eitkaplsas mikrydehhq dltllkalvr qqlpekykei ffdqskngya
 361 gyidggasqe efykfikpil ekmdgteell vklnredllr kqrtfdngsi phqihlgelh
 421 ailrrqedfy pflkdnreki ekiltfripy yvgplargns rfawmtrkse etitpwnfee
 481 vvdkgasaqs fiermtnfdk nlpnekvlpk hsllyeyftv yneltkvkyv tegmrkpafl
 541 sgeqkkaivd llfktnrkvt vkqlkedyfk kiecfdsvei sgvedrfnas lgtyhdllki
 601 ikdkdfldne enediledi ltltlfedre mieerlktya hlfddkvmkq lkrrrytgwg
 661 rlsrklingi rdkqsgktil dflksdgfan rnfmqlihdd sltfkediqk aqvsgqgdsl
 721 hehianlags paikkgilqt vkvvdelvkv mgrhkpeniv iemarangtt qkgqknsrer
 781 mkrieegike lgsqilkehp ventqlqnek lylyylqngr dmyvdqeldi nrlsdydvdh
 841 ivpqsflkdd sidnkvltrs dknrgksdnv pseevvkkmk nywrqllnak litqrkfdnl
 901 tkaergqlse ldkagfikrq lvetrqitkh vaqildsrmn tkydendkli revkvitlks
 961 klvsdfrkdf qfykvreinn yhhahdaylh avvgtalikk ypklesefvy gdykvydvrk
1021 miakseqeig katakyffys nimnffktei tlangeirkr plietngetg eivwdkgrdf
1081 atvrkvlsmp qvnivkktev qtggfskesi lpkrnsdkli arkkdwdpkk yggfdsptva
1141 ysvlvvakve kgkskklksv kellgitime rssfeknpid fleakgykev kkdliiklpk
1201 yslfelengr krmlasagel qkgnelalps kyvnflylas hyeklkgspe dneqkqlfve
1261 qhkhyldeii eqisefskrv iladanldkv lsaynkhrdk pireqaenii hlftltnlga
1321 paafkyfdtt idrkrytstk evldatlihq sitglyetri dlsqlggd
```

FIG. 1

Francisella tularensis subsp. novicida U112 Cpf1

```
   1 msiyqefvnk yslsktlrfe lipqgktlen ikarglildd ekrakdykka kqiidkyhqf
  61 fieeilssvc isedllqnys dvyfklkksd ddnlqkdfks akdtikkqis eyikdsekfk
 121 nlfnqnlida kkgqesdlil wlkqskdngi elfkansdit didealeiik sfkgwttyfk
 181 gfhenrknvy ssndiptsii yrivddnlpk flenkakyes lkdkapeain yeqikkdlae
 241 eltfdidykt sevnqrvfsl devfeianfn nylnqsgitk fntiiggkfv ngentkrkgi
 301 neyinlysqq indktlkkyk msvlfkqils dtesksfvid kleddsdvvt tmqsfyeqia
 361 afktveeksi ketlsllfdd lkaqkldlsk iyfkndkslt dlsqqvfddy svigtavley
 421 itqqiapknl dnpskkeqel iakktekaky lsletiklal eefnkhrdid kqcrfeeila
 481 nfaaipmifd eiaqnkdnla qisikyqnqg kkdllqasae ddvkaikdll dqtnnllhkl
 541 kifhisqsed kanildkdeh fylvfeecyf elanivplyn kirnyitqkp ysdekfklnf
 601 enstlangwd knkepdntai lfikddkyyl gvmnkknnki fddkaikenk gegykkivyk
 661 llpgankmlp kvffsaksik fynpsedilr irnhsthtkn gspqkgyekf efniedcrkf
 721 idfykqsisk hpewkdfgfr fsdtqrynsi defyrevenq gykltfenis esyidsvvnq
 781 gklylfqiyn kdfsayskgr pnlhtlywka lfdernlqdv vyklngeael fyrkqsipkk
 841 ithpakeaia nknkdnpkke svfeydlikd krftedkfff hcpitinfks sgankfndei
 901 nlllkekand vhilsidrge rhlayytlvd gkgniikqdt fniigndrmk tnyhdklaai
 961 ekdrdsarkd wkkinnikem kegylsqvvh eiaklvieyn aivvfedlnf gfkrgrfkve
1021 kqvyqklekm lieklnylvf kdnefdktgg vlrayqltap fetfkkmgkq tgliyyvpag
1081 ftskicpvtg fvnqlypkye svsksqeffs kfdkicynld kgyfefsfdy knfgdkaakg
1141 kwtiasfgsr linfrnsdkn hnwdtrevyp tkelekllkd ysieyghgec ikaaicgesd
1201 kkffakltsv lntilqmrns ktgteldyli spvadvngnf fdsrqapknm pqdadangay
1261 higlkglmll griknnqegk klnlviknee yfefvqnrnn
```

FIG. 2

AsCpf1

```
   1 mtqfegftnl yqvsktlrfe lipqgktlkh iqeqgfieed karndhykel kpiidriykt
  61 yadqclqlvq ldwenlsaai dsyrkektee trnalieeqa tyrnaihdyf igrtdnltda
 121 inkrhaeiyk glfkaelfng kvlkqlgtvt ttehenallr sfdkfttyfs gfyenrknvf
 181 saedistaip hrivqdnfpk fkenchiftr litavpslre hfenvkkaig ifvstsieev
 241 fsfpfynqll tqtqidlynq llggisreag tekikglnev lnlaiqknde tahiiaslph
 301 rfiplfkqil sdrntlsfil eefksdeevi qsfckyktll rnenvletae alfnelnsid
 361 lthifishkk letissalcd hwdtlrnaly erriseltgk itksakekvq rslkhedinl
 421 qeiisaagke lseafkqkts eilshahaal dqplpttlkk qeekeilksq ldsllglyhl
 481 ldwfavdesn evdpefsarl tgiklemeps lsfynkarny atkkpysvek fklnfqmptl
 541 asgwdvnkek nngailfvkn glyylgimpk qkgrykalsf eptektsegf dkmyydyfpd
 601 aakmipkcst qlkavtahfq thttpillsn nfiepleitk eiydlnnpek epkkfqtaya
 661 kktgdqkgyr ealckwidft rdflskytkt tsidlsslrp ssqykdlgey yaelnpllyh
 721 isfqriaeke imdavetgkl ylfqiynkdf akghhgkpnl htlywtglfs penlaktsik
 781 lngqaelfyr pksrmkrmah rlgekmlnkk lkdqktpipd tlyqelydyv nhrlshdlsd
 841 earallpnvi tkevsheiik drrftsdkff fhvpitlnyq aanspskfnq rvnaylkehp
 901 etpiigidrg ernliyitvi dstgkileqr slntiqqfdy qkkldnreke rvaarqawsv
 961 vgtikdlkqg ylsqviheiv dlmihyqavv vlenlnfgfk skrtgiaeka vyqqfekmli
1021 dklnclvlkd ypaekvggvl npyqltdqft sfakmgtqsg flfyvpapyt skidpltgfv
1081 dpfvwktikn hesrkhfleg fdflhydvkt gdfilhfkmn rnlsfqrglp gfmpawdivf
1141 eknetqfdak gtpfiagkri vpvienhrft gryrdlypan elialleekg ivfrdgsnil
1201 pkllenddsh aidtmvalir svlqmrnsna atgedyinsp vrdlnqvcfd srfqnpewpm
1261 dadangayhi alkgqlllnh lkeskdlklq ngisnqdwla yiqelrn
```

FIG. 11

LbCpf1

AASKLEKFTNCYSLSKTLRFKAIPVGKTQENIDNKRLLVEDEKRAEDYKGVKKLLDRYYL
SFINDVLHSIKLKNLNNYISLFRKKTRTEKENKELENLEINLRKEIAKAFKGAAGYKSLF
KKDIIETILPEAADDKDEIALVNSFNGFTTAFTGFFDNRENMFSEEAKSTSIAFRCINEN
LTRYISNMDIFEKVDAIFDKHEVQEIKEKILNSDYDVEDFFEGEFFNFVLTQEGIDVYNA
IIGGFVTESGEKIKGLNEYINLYNAKTKQALPKFKPLYKQVLSDRESLSFYGEGYTSDEE
VLEVFRNTLNKNSEIFSSIKKLEKLFKNFDEYSSAGIFVKNGPAISTISKDIFGEWNLIR
DKWNAEYDDIHLKKKAVVTEKYEDDRRKSFKKIGSFSLEQLQEYADADLSVVEKLKEIII
QKVDEIYKVYGSSEKLFDADFVLEKSLKKNDAVVAIMKDLLDSVKSFENYIKAFFGEGKE
TNRDESFYGDFVLAYDILLKVDHIYDAIRNYVTQKPYSKDKFKLYFQNPQFMGGWDKDKE
TDYRATILRYGSKYYLAIMDKKYAKCLQKIDKDDVNGNYEKINYKLLPGPNKMLPKVFFS
KKWMAYYNPSEDIQKIYKNGTFKKGDMFNLNDCHKLIDFFKDSISRYPKWSNAYDFNFSE
TEKYKDIAGFYREVEEQGYKVSFESASKKEVDKLVEEGKLYMFQIYNKDFSDKSHGTPNL
HTMYFKLLFDENNHGQIRLSGGAELFMRRASLKKEELVVHPANSPIANKNPDNPKKTTTL
SYDVYKDKRFSEDQYELHIPIAINKCPKNIFKINTEVRVLLKHDDNPYVIGIDRGERNLL
YIVVVDGKGNIVEQYSLNEIINNFNGIRIKTDYHSLLDKKEKERFEARQNWTSIENIKEL
KAGYISQVVHKICELVEKYDAVIALEDLNSGFKNSRVKVEKQVYQKFEKMLIDKLNYMVD
KKSNPCATGGALKGYQITNKFESFKSMSTQNGFIFYIPAWLTSKIDPSTGFVNLLKTKYT
SIADSKKFISSFDRIMYVPEEDLFEFALDYKNFSRTDADYIKKWKLYSYGNRIRIFAAAK
KNNVFAWEEVCLTSAYKELFNKYGINYQQGDIRALLCEQSDKAFYSSFMALMSLMLQMRN
SITGRTDVDFLISPVKNSDGIFYDSRNYEAQENAILPKNADANGAYNIARKVLWAIGQFK
KAEDEKLDKVKIAISNKEWLEYAQTSVK

FIG. 12

CATIONIC POLYMER WITH ALKYL SIDE CHAINS AND USE FOR BIOMOLECULE DELIVERY

CROSS-REFERENCE TO RELATED APPLICATIONS

This application is the U.S. national phase of International Patent Application No. PCT/US2019/057959, filed Oct. 24, 2019, which claims the benefit of U.S. Provisional Patent Application No. 62/750,123 filed Oct. 24, 2018, the entire disclosures of which are is hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted concurrently herewith and identified as follows: One 49,262 Byte ASCII (Text) file named "512974_ST25.TXT," created on Oct. 22, 2019.

BACKGROUND OF THE INVENTION

Peptide, protein, and nucleic based technologies have countless applications to prevent, cure and treat diseases. For instance, clustered regularly-interspaced short palindromic repeats ("CRISPR") based technologies have countless applications to prevent, cure and treat genetic diseases. However, the safe and effective delivery of large molecules (e.g., polypeptides and nucleic acids) to their target tissues remains problematic. In the case of CRISPR type systems, delivery of the multiple components of a CRISPR system (RNA-guided endonuclease or nucleic acid encoding same, guide RNA, and, in some cases, donor DNA) provides a substantial additional challenge. Accordingly, there continues to be a need for new compositions and methods useful for delivering large molecules to cells.

BRIEF SUMMARY OF THE INVENTION

Provided herein is a polymer comprising a structure of Formula 1:

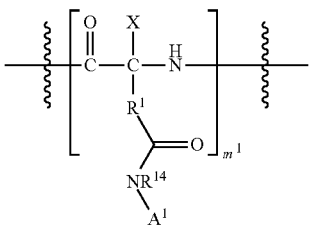

wherein,
$m^1$ is an integer from 1 to 2000;
$R^1$ is a methylene or ethylene group;
$R^{14}$ is hydrogen or a $C_1$-$C_{12}$ alkyl group, alkenyl group, cycloalkyl group, or cycloalkenyl group;
X is a $C_1$-$C_{12}$ alkyl group, cycloalkyl group, alkenyl group, cycloalkenyl group, aryl group, heteroalkyl group, or heterocyclic group;
$A^1$ is a group of formula

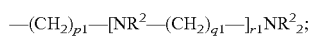

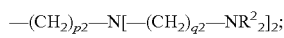

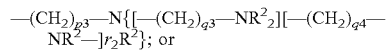

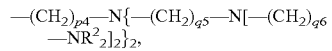

wherein p1 to p4, q1 to q6, and r1 and r2 are each independently an integer of 1 to 5; and each instance of $R^2$ is independently hydrogen or a $C_1$-$C_{12}$ alkyl group, alkenyl group, cycloalkyl group, or cycloalkenyl group.

Also provided is a polymer comprising a structure of Formula 3:

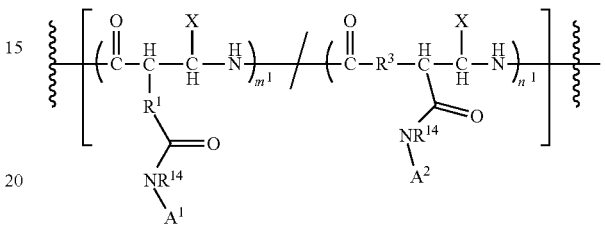

wherein,
each of $m^1$ and $n^1$ is an integer from 0 to 1000; provided that the sum of $m^1$+$n^1$ is greater than 5;
the symbol "/" indicates that the units separated thereby are linked randomly or in any order;
$R^1$ and $R^3$ each independently are a methylene or ethylene group;
each instance of $R^{14}$ is independently hydrogen or a $C_1$-$C_{12}$ alkyl group, alkenyl group, cycloalkyl group, or cycloalkenyl group;
each instance of X is independently a $C_1$-$C_{12}$ alkyl group, cycloalkyl group, alkenyl group, cycloalkenyl group, aryl group, heteroalkyl group, or heterocyclic group;
$A^1$ and $A^2$ are each independently a group of formula

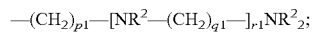

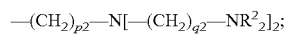

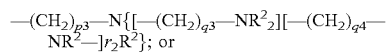

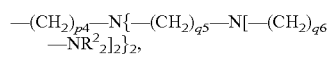

wherein p1 to p4, q1 to q6, and r1 and r2 are each independently an integer of 1 to 5; and each instance of $R^2$ is independently hydrogen or a $C_1$-$C_{12}$ alkyl group, alkenyl group, cycloalkyl group, or cycloalkenyl group.

The disclosure also provides a composition comprising a structure of Formula 1 and/or a structure of Formula 3, and a nucleic acid and/or polypeptide. Further provided is a method of preparing a polymer comprising a structure of Formula 1 and/or a structure of Formula 3, as well as methods of using the polymers and compositions comprising same, for example, to deliver a nucleic acid or protein to a cell.

BRIEF DESCRIPTION OF THE DRAWINGS

FIG. 1 provides the amino acid sequence of Cas9 from *Streptococcus pyogene* (SEQ ID NO:1).

FIG. 2 provides the amino acid sequence of Cpf1 from *Francisella tularensis* subsp. *Novicida* U112 (SEQ ID NO:2).

FIG. 11 provides the sequence of AsCpf1 (SEQ ID NO: 19).

FIG. 12 provides the sequence of LbCpf1 (SEQ ID NO: 20).

DETAILED DESCRIPTION OF THE INVENTION

Figure 3:
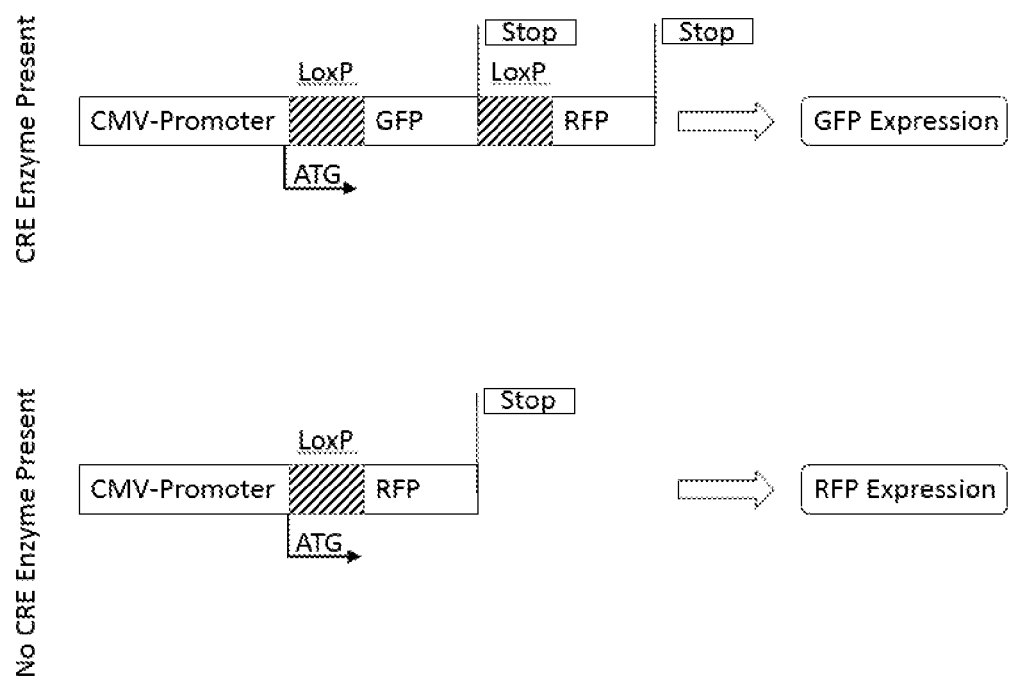
FIG. 3 is a schematic illustration of a traffic light reporter in HEK 293T.

The invention provides a polymer comprising a structure of Formula 1:

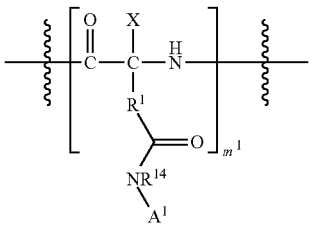

wherein,
$m^1$ is an integer from 1 to 2000;
$R^1$ is a methylene or ethylene group;
$R^{14}$ is hydrogen or a $C_1$-$C_{12}$ alkyl group, alkenyl group, cycloalkyl group, or cycloalkenyl group;
X is a $C_1$-$C_{12}$ alkyl group, cycloalkyl group, alkenyl group, cycloalkenyl group, aryl group, heteroalkyl group, or heterocyclic group;
$A^1$ is a group of formula

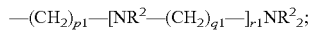

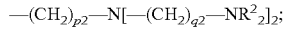

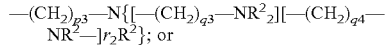

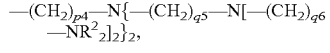

wherein p1 to p4, q1 to q6, and r1 and r2 are each independently an integer of 1 to 5; and each instance of $R^2$ is independently hydrogen or a $C_1$-$C_{12}$ alkyl group, alkenyl group, cycloalkyl group, or cycloalkenyl group.

The invention further provides a polymer having the structure of Formula 1A:

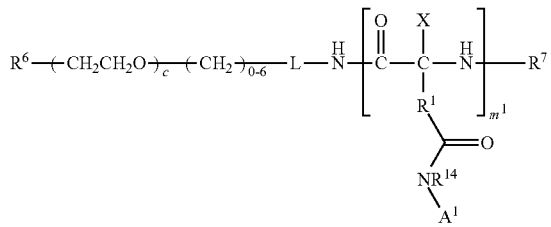

wherein,
c is an integer from 0 to 50;
L is optionally present and is a cleavable linker;
$m^1$ is an integer from 1 to 2000;
$R^1$ is a methylene or ethylene group;
$R^6$ is hydrogen, an amino group, an aryl group, a heterocyclic group (e.g., aromatic or non-aromatic), a $C_1$-$C_{12}$ alkyl group, alkenyl group, cycloalkyl group, or cycloalkenyl group, a $C_1$-$C_{12}$ linear or branched alkyl group optionally substituted with one or more amines; or a tissue-specific or cell-specific targeting moiety;
$R^7$ is hydrogen, an aryl group, a heterocyclic group (e.g., aromatic or non-aromatic), a $C_1$-$C_{12}$ alkyl group, alkenyl group, cycloalkyl group, or cycloalkenyl group, or a $C_1$-$C_{12}$ linear or branched alkyl group optionally substituted with one or more substituents;
$R^{14}$ is hydrogen or a $C_1$-$C_{12}$ alkyl group, alkenyl group, cycloalkyl group, or cycloalkenyl group;
X is a $C_1$-$C_{12}$ alkyl group, cycloalkyl group, alkenyl group, cycloalkenyl group, aryl group, heteroalkyl group, or heterocyclic group;
$A^1$ is a group of formula

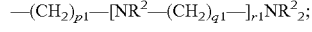

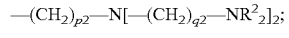

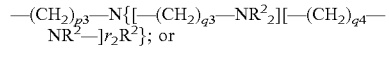

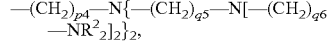

wherein p1 to p4, q1 to q6, and r1 and r2 are each independently an integer of 1 to 5; and each instance of $R^2$ is independently hydrogen or a $C_1$-$C_{12}$ alkyl group, alkenyl group, cycloalkyl group, or cycloalkenyl group.

As used herein, "alkyl" or "alkylene" refers to a substituted or unsubstituted hydrocarbon chain. The alkyl group can have any number of carbon atoms (e.g., $C_1$-$C_{100}$ alkyl, $C_1$-$C_{50}$ alkyl, $C_1$-$C_{12}$ alkyl, $C_1$-$C_8$ alkyl, $C_1$-$C_6$ alkyl, $C_1$-$C_4$ alkyl, $C_1$-$C_2$ alkyl, etc.), and can be saturated, unsaturated (e.g., alkenyl or alkynyl), linear, branched, straight-chained, cyclic (e.g., cycloalkyl or cycloalkenyl), or a combination thereof. Cyclic groups can be monocyclic, fused to form bicyclic or tricyclic groups, linked by a bond, or spirocyclic. In some embodiments, the alkyl substituent can be interrupted by one or more heteroatoms (e.g., oxygen, nitrogen, and sulfur), thereby providing a heteroalkyl, heteroalkylene, or heterocyclyl (i.e., a heterocyclic group). In some embodiments, the alkyl is substituted with one or more substituents.

The term "aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. In some embodiments, the aryl group comprises an alkylene linking group so as to form an arylalkyl group (e.g., a benzyl group). Some aryl groups have from 6 to 12 ring members, such as phenyl, naphthyl or biphenyl. Other aryl groups have from 6 to 10 ring members, such as phenyl or naphthyl. In some embodiments, the aryl substituent can be interrupted by one or more heteroatoms (e.g., oxygen, nitrogen, and sulfur), thereby proving a heterocyclyl (i.e., a heterocyclic group). In some embodiments, the aryl is substituted with one or more substituents.

The term "heterocyclyl," "heterocycle," or "heterocyclic group" refers to a cyclic group, e.g., aromatic (i.e., heteroaryl) or non-aromatic where the cyclic group has one or more heteroatoms (e.g., oxygen, nitrogen, and sulfur). Heterocyclic groups can be monocyclic, fused to form bicyclic or tricyclic groups, linked by a bond, or spirocyclic. In some embodiments, the heterocyclyl (i.e., a heterocyclic group) is substituted with one or more substituents.

As used herein, the term "substituted" can mean that one or more hydrogens on the designated atom or group (e.g., substituted alkyl group) are replaced with another group provided that the designated atom's normal valence is not exceeded. For example, when the substituent is oxo (i.e., =O), then two hydrogens on the atom are replaced. Substituent groups can include one or more of an aldehyde, an ester, an amide, a ketone, nitro, cyano, fluoroalkyl (e.g., trifluoromethane), halo (e.g., fluoro), aryl (e.g., phenyl), heterocyclyl (e.g., heteroaryl), heteroalkyl, oxo, or combinations thereof. Combinations of substituents and/or variables are permissible provided that the substitutions do not significantly adversely affect synthesis or use of the compound.

As used herein, the terms "independent" and "independently," when referring to one or more constituent (e.g., p1 to p4, q1 to q6, r1, r2, and $R^2$), means that each substituent is individually selected from the list and can be the same or different. For example, if constituent $R^2$ appears more than once in a formula and $R^2$ is independently selected from a recited list, then each $R^2$ may be the same or different and selected from the recited list.

In some embodiments, the polymer comprising a structure of Formula 1 is modified to form a polymer comprising a structure of Formula 2:

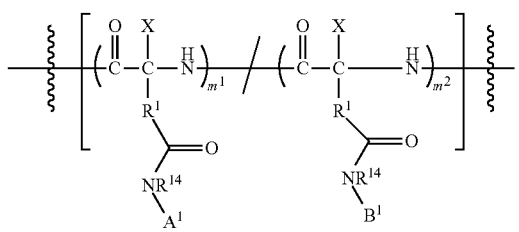

wherein,
$m^1$ is an integer from 1 to 1000;
$m^2$ is an integer from 1 to 1000;
the symbol "/" indicates that the units separated thereby are linked randomly or in any order;
each $R^1$ independently is a methylene or ethylene group;
each instance of $R^{14}$ is independently hydrogen or a $C_1$-$C_{12}$ alkyl group, alkenyl group, cycloalkyl group, or cycloalkenyl group;
each instance of X is independently a $C_1$-$C_{12}$ alkyl group, cycloalkyl group, alkenyl group, cycloalkenyl group, aryl group, heteroalkyl group, or heterocyclic group;
$A^1$ is a group of formula

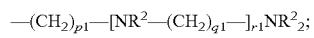

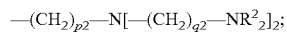

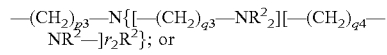; or

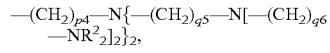

$B^1$ is a group of formula

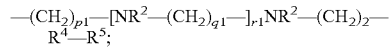

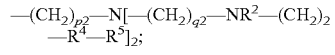

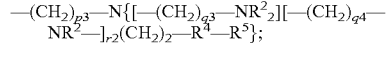

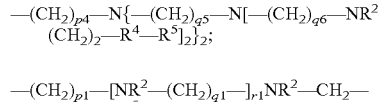

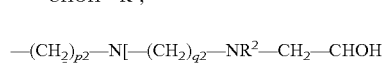

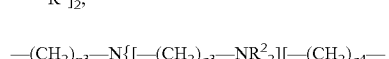

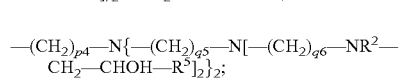

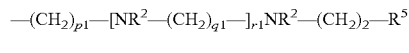

—$(CH_2)_{p1}$—[$NR^2$—$(CH_2)_{q1}$—]$_{r1}NR^2$—$(CH_2)_2$—$R^5$;

—$(CH_2)_{p2}$—N[—$(CH_2)_{q2}$—$NR^2$—$(CH_2)_{r2}$—$R^5$]$_2$;

—$(CH_2)_{p3}$—N{[—$(CH_2)_{q3}$—$NR^2_2$][—$(CH_2)_{q4}$—$NR^2$—]$_{r2}(CH_2)_2$—$R^5$}; or

—$(CH_2)_{p4}$—N{—$(CH_2)_{q5}$—N[—$(CH_2)_{q6}$—$NR^2$—$(CH_2)_2$—$R^5$]$_2$}$_2$, wherein p1 to p4, q1 to q6, and r1 and r2 are each independently an integer of 1 to 5; each instance of $R^2$ is independently hydrogen or a $C_1$-$C_{12}$ alkyl group, alkenyl group, cycloalkyl group, or cycloalkenyl group; each instance of $R^4$ is independently —C(O)O—, —C(O)NH—, or —S(O)(O)—; and each instance of $R^5$ is independently an alkyl group, cycloalkyl group, alkenyl group, cycloalkenyl group, aryl group, heteroalkyl group, or heterocyclic group optionally comprising from 2 to 8 tertiary amines or a substituent comprising a tissue-specific or cell-specific targeting moiety.

Accordingly, the invention also provides a polymer having the structure of Formula 2A:

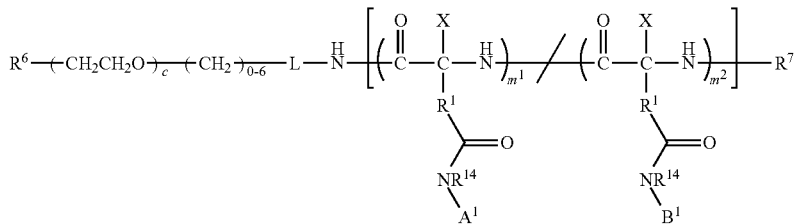

wherein, c is an integer from 0 to 50;

L is optionally present and is a cleavable linker;

$m^1$ is an integer from 1 to 1000;

$m^2$ is an integer from 1 to 1000;

the symbol "/" indicates that the units separated thereby are linked randomly or in any order;

each $R^1$ independently is a methylene or ethylene group;

$R^6$ is hydrogen, an amino group, an aryl group, a heterocyclic group (e.g., aromatic or non-aromatic), a $C_1$-$C_{12}$ alkyl group, alkenyl group, cycloalkyl group, or cycloalkenyl group, a $C_1$-$C_{12}$ linear or branched alkyl group optionally substituted with one or more amines; or a tissue-specific or cell-specific targeting moiety;

$R^7$ is hydrogen, an aryl group, a heterocyclic group (e.g., aromatic or non-aromatic), a $C_1$-$C_{12}$ alkyl group, alkenyl group, cycloalkyl group, or cycloalkenyl group, or a $C_1$-$C_{12}$ linear or branched alkyl group optionally substituted with one or more substituents;

each instance of $R^{14}$ is independently hydrogen or a $C_1$-$C_{12}$ alkyl group, alkenyl group, cycloalkyl group, or cycloalkenyl group;

each instance of X is independently a $C_1$-$C_{12}$ alkyl group, cycloalkyl group, alkenyl group, cycloalkenyl group, aryl group, heteroalkyl group, or heterocyclic group;

$A^1$ is a group of formula

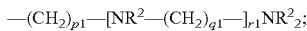

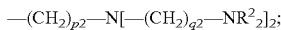

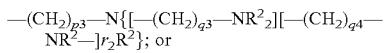

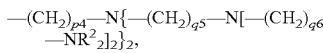

$B^1$ is a group of formula

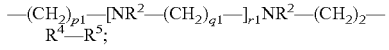

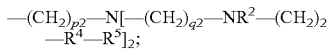

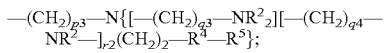

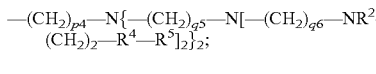

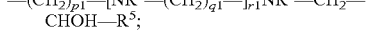

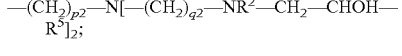

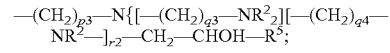

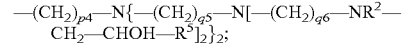

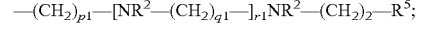

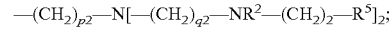

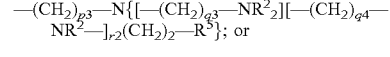

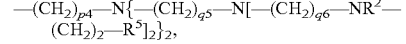

wherein p1 to p4, q1 to q6, and r1 and r2 are each independently an integer of 1 to 5; each instance of $R^2$ is independently hydrogen or a $C_1$-$C_{12}$ alkyl group, alkenyl group, cycloalkyl group, or cycloalkenyl group; each instance of $R^4$ is independently —C(O)O—, —C(O)NH—, or —S(O)(O)—; and each instance of $R^5$ is independently an alkyl group, cycloalkyl group, alkenyl group, cycloalkenyl group, aryl group, heteroalkyl group, or heterocyclic group optionally comprising from 2 to 8 tertiary amines or a substituent comprising a tissue-specific or cell-specific targeting moiety.

Thus, in the structures of Formula 2 and Formula 2A, the monomers (which can be referred to by their respective side chains $A^1$ and $B^1$) can be arranged randomly or in any order. Thus, $m^1$ and $m^2$ merely denote the number of the respective monomers that appear in the chain overall, and not necessarily represent blocks of those monomers, although blocks or stretches of a given monomer might be present in some embodiments.

In the polymer structures, each $R^1$ independently is a methylene or ethylene group. In certain embodiments, each $R^1$ is an ethylene group. In preferred embodiments, each $R^1$ is a methylene group.

In groups $A^1$ and $B^1$, integers p1 to p4 (i.e., p1, p2, p3, and p4), q1 to q6 (i.e., q1, q2, q3, q4, q5, and q6), and r1 and r2 are each independently an integer of 1 to 5 (e.g., 1, 2, 3, 4, or 5). In some embodiments, p1 to p4 (i.e., p1, p2, p3, and p4), q1 to q6 (i.e., q1, q2, q3, q4, q5, and q6), and/or r1 and r2 are each independently an integer of 1 to 3 (e.g., 1, 2, or 3). In certain embodiments, p1 to p4 (i.e., p1, p2, p3, and p4) and/or q1 to q6 (i.e., q1, q2, q3, q4, q5, and q6) are each 2. In some embodiments, p1 to p4 (i.e., p1, p2, p3, and p4) and/or q1 to q6 (i.e., q1, q2, q3, q4, q5, and q6) are each 2, and r1 and r2 are each 1.

In the polymer structures, each instance of $R^4$ is independently —C(O)O—, —C(O)NH—, or —S(O)(O)—. In some embodiments, each instance of $R^4$ is independently —C(O)O— or —C(O)NH—. In certain embodiments, each instance of $R^4$ is —C(O)O—. In certain embodiments, each instance of $R^4$ is —C(O)NH—.

In some embodiments of Formula 1, Formula 1A, Formula 2, or Formula 2A, $A^1$ is a group of formula $-(CH_2)_{p1}-[NH-(CH_2)_{q1}-]_{r1}NH_2$, such as a group $-(CH_2)_2-NH-(CH_2)_2-NH_2$. In addition, or alternatively, $B^1$, when present, can be a group of formula $-(CH_2)_{p1}-[NH-(CH_2)_{q1}-]_{r1}NH-(CH_2)_2-R^4-R^5$, such as a group $-(CH_2)_2-NH-(CH_2)_2-NH-(CH_2)_2-R^4-R^5$, or a group $-(CH_2)_2-NH-(CH_2)_2-NH-(CH_2)_2-C(O)-O-R^5$.

Furthermore, in the polymer structures, each instance of $R^5$ is independently an alkyl group, cycloalkyl group, alkenyl group, cycloalkenyl group, aryl group, heteroalkyl group, or heterocyclic group, optionally comprising from 2 to 8 tertiary amines or a substituent comprising a tissue-specific or cell-specific targeting moiety. $R^5$ can comprise from about 2 to about 50 carbon atoms (e.g., from about 2 to about 40 carbon atoms, from about 2 to about 30 carbon atoms, from about 2 to about 20 carbon atoms, from about 2 to about 16 carbon atoms, from about 2 to about 12 carbon atoms, from about 2 to about 10 carbon atoms, or from about 2 to about 8 carbon atoms). In some embodiments, $R^5$ is a heteroalkyl group comprising from 2 to 8 (i.e., 2, 3, 4, 5, 6, 7, or 8) tertiary amines. The tertiary amines can be part of the heteroalkyl backbone (i.e., the longest continuous chain of atoms in the heteroalkyl group, or a pendant substituent. Thus, for instance, the heteroalkyl group comprising the tertiary amines can provide an alkylamino group, amino alkyl group, alkylaminoalkyl group, aminoalkylamino group, or the like comprising 2 to 8 tertiary amines.

In some embodiments, each $R^5$ is independently selected from:

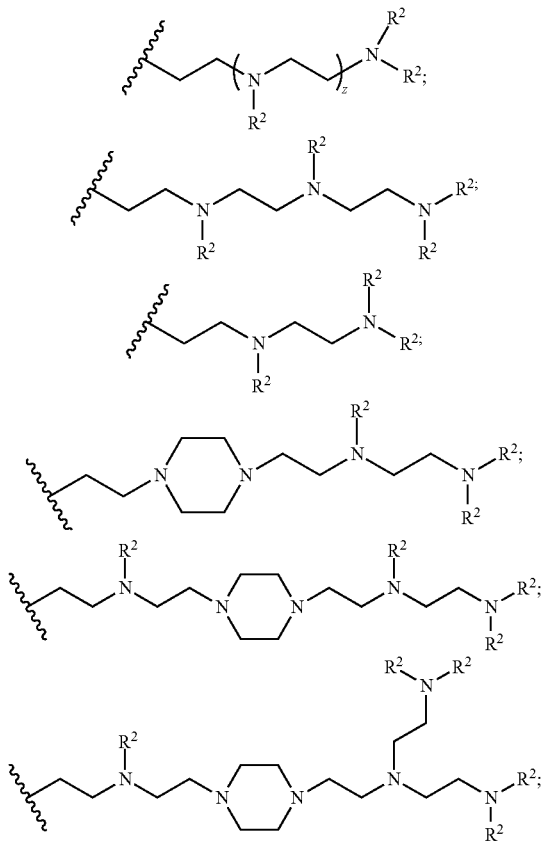

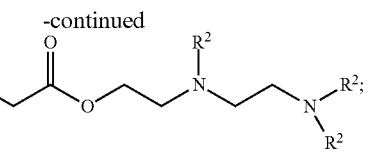

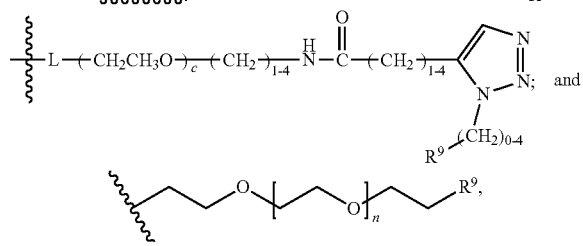

wherein
- each instance of $R^2$ is independently hydrogen or a $C_1$-$C_{12}$ alkyl group, alkenyl group, cycloalkyl group, or cycloalkenyl group;
- $R^8$ is a $C_1$-$C_{50}$ alkyl group, alkenyl group, cycloalkyl group, or cycloalkenyl group optionally substituted with one or more amines;
- z is an integer from 1 to 5;
- c is an integer from 0 to 50;
- L is optionally present and is a cleavable linker;
- n is an integer from 0 to 50; and
- $R^9$ is a tissue-specific or cell-specific targeting moiety.

$R^2$ can be hydrogen or a $C_1$-$C_{12}$ alkyl group, alkenyl group, cycloalkyl group, or cycloalkenyl group. In some embodiments, $R^2$ is a $C_1$-$C_{12}$ (e.g., a $C_1$-$C_{10}$ alkyl group; a $C_1$-$C_8$ alkyl group; a $C_1$-$C_6$ alkyl group; a $C_1$-$C_4$ alkyl group, a $C_1$-$C_3$ alkyl group, or a $C_1$ or $C_2$ alkyl group) linear or branched alkyl group. In certain embodiments, $R^2$ is methyl. In other embodiments, $R^2$ can be hydrogen. Typically, within a given polymer, each $R^2$ is the same (e.g., all methyl or all hydrogen); however, each $R^2$ is independently chosen and can be the same or different.

$R^6$ can be hydrogen, an amino group, an aryl group, a heterocyclic group (e.g., aromatic or non-aromatic), a $C_1$-$C_{12}$ alkyl group, alkenyl group, cycloalkyl group, or cycloalkenyl group, a $C_1$-$C_{12}$ linear or branched alkyl group optionally substituted with one or more amines; or a tissue-specific or cell-specific targeting moiety. In some embodiments, $R^6$ is a $C_1$-$C_{12}$ (e.g., a $C_1$-$C_{10}$ alkyl group; a $C_1$-$C_8$ alkyl group; a $C_1$-$C_6$ alkyl group; a $C_1$-$C_4$ alkyl group, a $C_1$-$C_3$ alkyl group, or a $C_1$ or $C_2$ alkyl group) linear or branched alkyl group substituted with one or more substituents (e.g., to form a heteroalkyl group). In certain embodiments, the heteroalkyl or alkyl group comprises or is substituted with one or more amines, for instance, from 2 to 8 (i.e., 2, 3, 4, 5, 6, 7, or 8) tertiary amines. The tertiary amines can be a part of the heteroalkyl backbone chain or pendant substituents.

$R^7$ can be hydrogen, an aryl group, a heterocyclic group (e.g., aromatic or non-aromatic), a $C_1$-$C_{12}$ alkyl group, alkenyl group, cycloalkyl group, or cycloalkenyl group, or a $C_1$-$C_{12}$ linear or branched alkyl group optionally substituted with one or more substituents (e.g., oxygen or amine). In some embodiments, $R^7$ is a $C_1$-$C_{12}$ (e.g., a $C_1$-$C_{10}$ alkyl group; a $C_1$-$C_8$ alkyl group; a $C_1$-$C_6$ alkyl group; a $C_1$-$C_4$ alkyl group, a $C_1$-$C_3$ alkyl group, or a $C_1$ or $C_2$ alkyl group) linear or branched alkyl group substituted with one or more substituents (e.g., to form a heteroalkyl group). In certain embodiments, the heteroalkyl or alkyl group comprises or is substituted with one or more amines, for instance, from 2 to 8 (i.e., 2, 3, 4, 5, 6, 7, or 8) tertiary amines. The tertiary amines can be a part of the heteroalkyl backbone chain or pendant substituents.

$R^8$ can be a $C_1$-$C_{50}$ (e.g., $C_1$-$C_{40}$, $C_1$-$C_{30}$, $C_1$-$C_{20}$, $C_1$-$C_{10}$, $C_4$-$C_{12}$, or $C_6$-$C_8$) alkyl group, alkenyl group, cycloalkyl group, or cycloalkenyl group optionally substituted with one or more amines. In some embodiments, $R^8$ is a $C_4$-$C_{12}$, such as a $C_6$-$C_8$, alkyl group, alkenyl group, cycloalkyl group, or cycloalkenyl group optionally substituted with one or more amines. In some embodiments, $R^8$ is substituted with one or more amines. In certain embodiments, $R^8$ is substituted with 2 to 8 (i.e., 2, 3, 4, 5, 6, 7, or 8) tertiary amines. The tertiary amines can be a part of the alkyl group (i.e., encompassed in the alkyl group backbone) or a pendant substituent.

$R^{14}$ can be hydrogen or a $C_1$-$C_{12}$ alkyl group, alkenyl group, cycloalkyl group, or cycloalkenyl group. In some embodiments, $R^{14}$ is a $C_1$-$C_{12}$ (e.g., a $C_1$-$C_{10}$ alkyl group; a $C_1$-$C_8$ alkyl group; a $C_1$-$C_6$ alkyl group; a $C_1$-$C_4$ alkyl group, a $C_1$-$C_3$ alkyl group, or a $C_1$ or $C_2$ alkyl group) linear or branched alkyl group. In certain embodiments, $R^{14}$ is methyl. In other embodiments, $R^{14}$ can be hydrogen. Typically, within a given polymer, each $R^{14}$ is the same (e.g., all methyl or all hydrogen); however, each $R^{14}$ is independently chosen and can be the same or different.

Each instance of L is optionally present. As used herein, the phrase "optionally present" means that a substituent designated as optionally present can be present or not present, and when that substituent is not present, the adjoining substituents are bound directly to each other. When L is present, L is a cleavable linker. As used herein, the phrase "cleavable linker" refers to any chemical element that connects two species that can be cleaved as to separate the two species. For example, the cleavable linker can be cleaved by a hydrolytic process, photochemical process, radical process, enzymatic process, electrochemical process, or a combination thereof. Exemplary cleavable linkers include, but are not limited to:

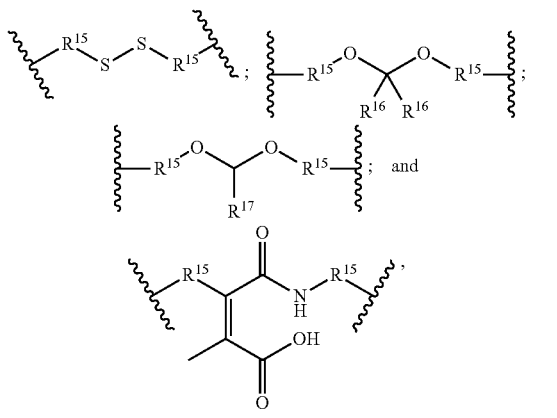

wherein each occasion of $R^{15}$ independently is a $C_1$-$C_4$ alkyl group, each occasion of $R^{16}$ independently is hydrogen, an aryl group, a heterocyclic group (e.g., aromatic or non-aromatic), a $C_1$-$C_{12}$ alkyl group, alkenyl group, cycloalkyl group, or cycloalkenyl group, and $R^{17}$ is a six-membered aromatic or heteroaromatic group optionally substituted with one or more —OCH$_3$, —NHCH$_3$, —N(CH$_3$)$_2$, —SCH$_3$, —OH, or a combination thereof.

By way of further illustration, the polymer could instead be described as Formula 2.1:

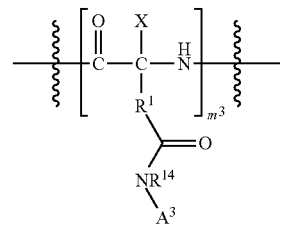

wherein,
$m^3$ is an integer from 5-2000 (e.g., 5-1000, 5-500, 5-100, 25-2000, 25-500, 25-100, 50-2000, 50-1000, 50-500, or 50-100);
each $R^1$ independently is a methylene or ethylene group;
$R^{14}$ is hydrogen or a $C_1$-$C_{12}$ alkyl group, alkenyl group, cycloalkyl group, or cycloalkenyl group;
each instance of X is independently a $C_1$-$C_{12}$ alkyl group, cycloalkyl group, alkenyl group, cycloalkenyl group, aryl group, heteroalkyl group, or heterocyclic group;
each $A^3$ independently is a group of formula

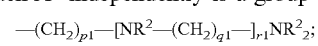

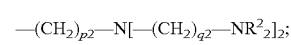

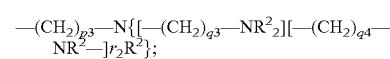

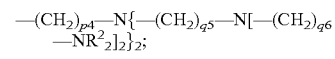

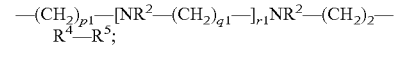

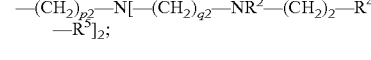

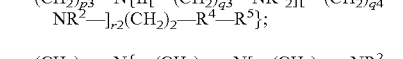

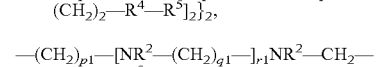

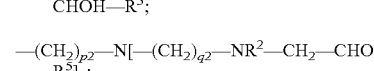

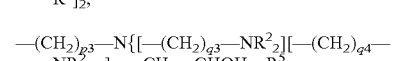

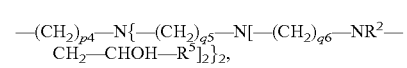

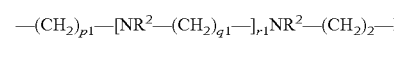

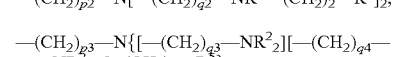

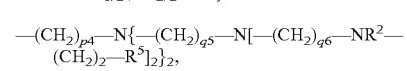

wherein p1 to p4, q1 to q6, and r1 and r2 are each independently an integer of 1 to 5; each instance of $R^2$ is independently hydrogen or a $C_1$-$C_{12}$ alkyl group, alkenyl group, cycloalkyl group, or cycloalkenyl group; each instance of $R^4$ is independently —C(O)O—, —C(O)NH—, or —S(O)(O)—; and each instance of $R^5$ is independently an alkyl group, cycloalkyl group, alkenyl group, cycloalkenyl group, aryl group, heteroalkyl group, or heterocyclic group optionally comprising from 2 to 8 tertiary amines or a substituent comprising a tissue-specific or cell-specific targeting moiety;

provided that at least about 5% (such as at least about 10%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or even 100%) of the $A^3$ groups are selected from

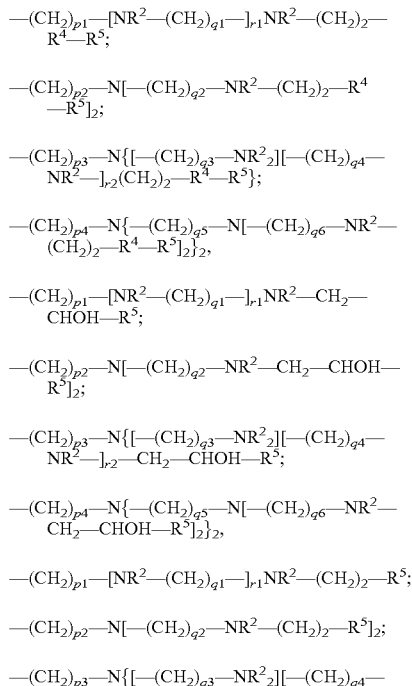

In still other embodiments, the polymer has some or even a majority of $A^3$ groups (at least about 5%, at least about 10%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%) that are selected from

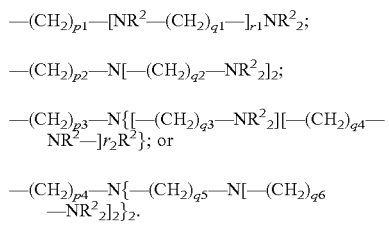

In some embodiments of Formula 2.1, $A^3$ is a group of the formula $-(CH_2)_{p1}-[NH-(CH_2)_{q1}-]_{r1}NH_2$, such as a group $-(CH_2)_2-NH-(CH_2)_2-NH_2$; or a group of formula $-(CH_2)_{p1}-[NH-(CH_2)_{q1}-]_{r1}NH-(CH_2)_2-R^4-R^5$, such as a group $-(CH_2)_2-NH-(CH_2)_2-NH-(CH_2)_2-R^4-R^5$, or a group $-(CH_2)_2-NH-(CH_2)_2-NH-(CH_2)_2-C(O)-O-R^5$; provided that at least about 5% (such as at least about 10%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or even 100%) of the $A^3$ groups are $-(CH_2)_{p1}-[NH-(CH_2)_{q1}-]_{r1}NH-(CH_2)_2-R^4-R^5$, such as a group $-(CH_2)_2-NH-(CH_2)_2-NH-(CH_2)_2-R^4-R^5$, or a group $-(CH_2)_2-NH-(CH_2)_2-NH-(CH_2)_2-C(O)-O-R^5$. Additionally, in some embodiments, the polymer has some or even a majority of $A^3$ groups (at least about 5%, at least about 10%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%) that are $-(CH_2)_{p1}-[NH-(CH_2)_{q1}-]_{r1}NH-(CH_2)_2-R^4-R^5$, such as a group $-(CH_2)_2-NH-(CH_2)_2-NH-(CH_2)_2-R^4-R^5$, or a group $-(CH_2)_2-NH-(CH_2)_2-NH-(CH_2)_2-C(O)-O-R^5$.

The polymer can be any suitable polymer, provided the polymer comprises the foregoing polymer structure. In some embodiments, the polymer is a block copolymer comprising a polymer block having the structure of Formula 1, 1A, 2, 2.1, or 2A, and one or more other polymer blocks (e.g., an ethylene oxide subunit, or a propylene oxide subunit). In other embodiments, the structure of Formula 1, 1A, 2, 2.1, or 2A is the only polymeric unit of the polymer. In certain embodiments, the polymer further comprises a substituent comprising a tissue-specific or cell-specific targeting moiety.

In some embodiments, the polymer has structure of Formula 1B:

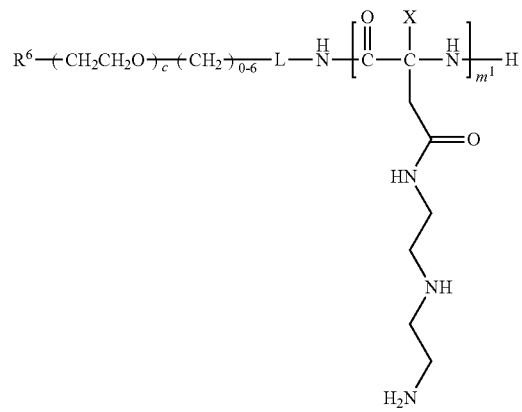

wherein,
c is an integer from 0 to 50;
L is optionally present and is a cleavable linker;
$m^1$ is an integer from 1 to 2000;
$R^6$ is hydrogen, an amino group, an aryl group, a heterocyclic group (e.g., aromatic or non-aromatic), a $C_1$-$C_{12}$ alkyl group, alkenyl group, cycloalkyl group, or cycloalkenyl group, a $C_1$-$C_{12}$ linear or branched alkyl group optionally substituted with one or more amines; or a tissue-specific or cell-specific targeting moiety; and
X is a $C_1$-$C_{12}$ alkyl group, cycloalkyl group, alkenyl group, cycloalkenyl group, aryl group, heteroalkyl group, or heterocyclic group, or Formula 2B:

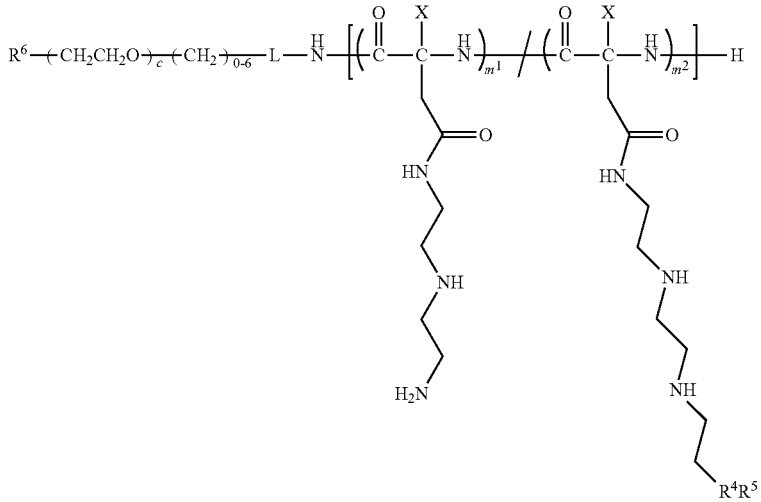

wherein,
c is an integer from 0 to 50;
L is optionally present and is a cleavable linker;
$m^1$ is an integer from 1 to 1000;
$m^2$ is an integer from 1 to 1000;
the symbol "/" indicates that the units separated thereby are linked randomly or in any order;
$R^6$ is hydrogen, an amino group, an aryl group, a heterocyclic group (e.g., aromatic or non-aromatic), a $C_1$-$C_{12}$ alkyl group, alkenyl group, cycloalkyl group, or cycloalkenyl group, a $C_1$-$C_{12}$ linear or branched alkyl group optionally substituted with one or more amines; or a tissue-specific or cell-specific targeting moiety;
each instance of X is independently a $C_1$-$C_{12}$ alkyl group, cycloalkyl group, alkenyl group, cycloalkenyl group, aryl group, heteroalkyl group, or heterocyclic group;
$R^4$ is —C(O)O—, —C(O)NH—, or —S(O)(O)—; and
$R^5$ is an alkyl group, cycloalkyl group, alkenyl group, cycloalkenyl group, aryl group, heteroalkyl group, or heterocyclic group optionally comprising from 2 to 8 tertiary amines or a substituent comprising a tissue-specific or cell-specific targeting moiety.

In certain embodiments, the polymer has structure of Formula 1C:

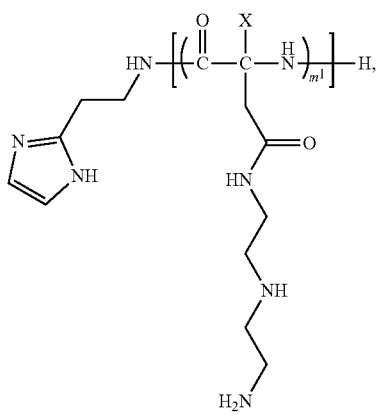

wherein $m^1$ is an integer from 1 to 2000 and X is a $C_1$-$C_{12}$ alkyl group, cycloalkyl group, alkenyl group, cycloalkenyl group, aryl group, heteroalkyl group, or heterocyclic group, or Formula 2C:

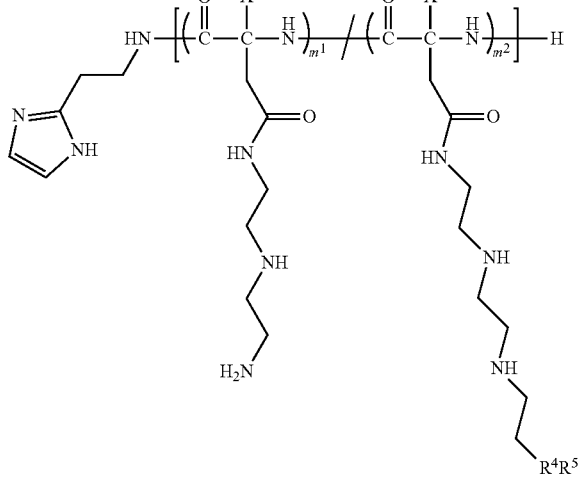

wherein,
$m^1$ is an integer from 1 to 1000;
$m^2$ is an integer from 1 to 1000;
the symbol "/" indicates that the units separated thereby are linked randomly or in any order;
each instance of X is independently a $C_1$-$C_{12}$ alkyl group, cycloalkyl group, alkenyl group, cycloalkenyl group, aryl group, heteroalkyl group, or heterocyclic group;
$R^4$ is —C(O)O—, —C(O)NH—, or —S(O)(O)—; and
$R^5$ is an alkyl group, cycloalkyl group, alkenyl group, cycloalkenyl group, aryl group, heteroalkyl group, or heterocyclic group optionally comprising from 2 to 8 tertiary amines or a substituent comprising a tissue-specific or cell-specific targeting moiety.

The invention also provides a polymer comprising a structure of Formula 3:

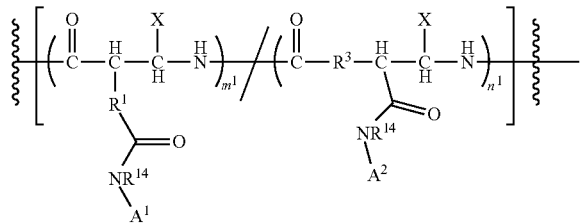

wherein,
each of $m^1$ and $n^1$ is an integer from 0 to 1000; provided that the sum of $m^1+n^1$ is greater than 5;
the symbol "/" indicates that the units separated thereby are linked randomly or in any order;
$R^1$ and $R^3$ each independently are a methylene or ethylene group;
each instance of $R^{14}$ is independently hydrogen or a $C_1$-$C_{12}$ alkyl group, alkenyl group, cycloalkyl group, or cycloalkenyl group;
each instance of X is independently a $C_1$-$C_{12}$ alkyl group, cycloalkyl group, alkenyl group, cycloalkenyl group, aryl group, heteroalkyl group, or heterocyclic group;
$A^1$ and $A^2$ are each independently a group of formula $-(CH_2)_{p1}-[NR^2-(CH_2)_{q1}-]_{r1}NR^2_2;$ $-(CH_2)_{p2}-N[-(CH_2)_{q2}-NR^2_2]_2;$ $-(CH_2)_{p3}-N\{[-(CH_2)_{q3}-NR^2_2][-(CH_2)_{q4}-NR^2-]_{r2}R^2\};$ or $-(CH_2)_{p4}-N\{-(CH_2)_{q5}-N[-(CH_2)_{q6}-NR^2_2]_2\}_2,$ wherein p1 to p4, q1 to q6, and r1 and r2 are each independently an integer of 1 to 5; and each instance of $R^2$ is independently hydrogen or a $C_1$-$C_{12}$ alkyl group, alkenyl group, cycloalkyl group, or cycloalkenyl group.

The invention further provides a polymer having the structure of Formula 3A:

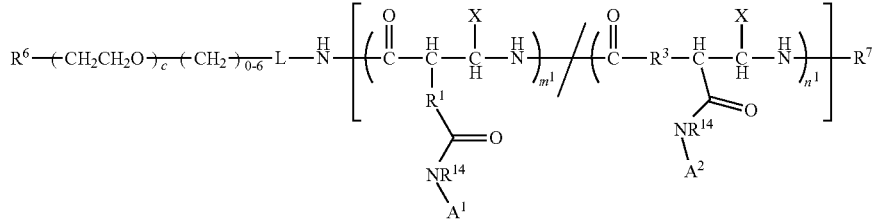

wherein,
c is an integer from 0 to 50;
L is optionally present and is a cleavable linker;
each of $m^1$ and $n^1$ is an integer from 0 to 1000; provided that the sum of $m^1+n^1$ is greater than 5;
the symbol "/" indicates that the units separated thereby are linked randomly or in any order;
$R^1$ and $R^3$ each independently are a methylene or ethylene group;
$R^6$ is hydrogen, an amino group, an aryl group, a heterocyclic group (e.g., aromatic or non-aromatic), a $C_1$-$C_{12}$ alkyl group, alkenyl group, cycloalkyl group, or cycloalkenyl group, a $C_1$-$C_{12}$ linear or branched alkyl group optionally substituted with one or more amines; or a tissue-specific or cell-specific targeting moiety;
$R^7$ is hydrogen, an aryl group, a heterocyclic group (e.g., aromatic or non-aromatic), a $C_1$-$C_{12}$ alkyl group, alkenyl group, cycloalkyl group, or cycloalkenyl group, or a $C_1$-$C_{12}$ linear or branched alkyl group optionally substituted with one or more substituents;
each instance of $R^{14}$ is independently hydrogen or a $C_1$-$C_{12}$ alkyl group, alkenyl group, cycloalkyl group, or cycloalkenyl group;
each instance of X is independently a $C_1$-$C_{12}$ alkyl group, cycloalkyl group, alkenyl group, cycloalkenyl group, aryl group, heteroalkyl group, or heterocyclic group;
$A^1$ and $A^2$ are each independently a group of formula $-(CH_2)_{p1}-[NR^2-(CH_2)_{q1}-]_{r1}NR^2_2;$ $-(CH_2)_{p2}-N[-(CH_2)_{q2}-NR^2_2]_2;$ $-(CH_2)_{p3}-N\{[-(CH_2)_{q3}-NR^2_2][-(CH_2)_{q4}-NR^2-]_{r2}R^2\};$ or $-(CH_2)_{p4}-N\{-(CH_2)_{q5}-N[-(CH_2)_{q6}-NR^2_2]_2\}_2,$ wherein p1 to p4, q1 to q6, and r1 and r2 are each independently an integer of 1 to 5; and each instance of $R^2$ is independently hydrogen or a $C_1$-$C_{12}$ alkyl group, alkenyl group, cycloalkyl group, or cycloalkenyl group.

Thus, in the structures of Formula 3 and Formula 3A, the monomers (which can be referred to by their respective side chains $A^1$ and $B^1$) can be arranged randomly or in any order. Thus, $m^1$ and $m^2$ merely denote the number of the respective monomers that appear in the chain overall, and not necessarily represent blocks of those monomers, although blocks or stretches of a given monomer might be present in some embodiments.

In some embodiments, the polymer comprising a structure of Formula 3 is modified to form a polymer comprising a structure of Formula 4:

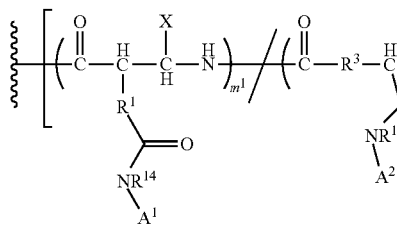 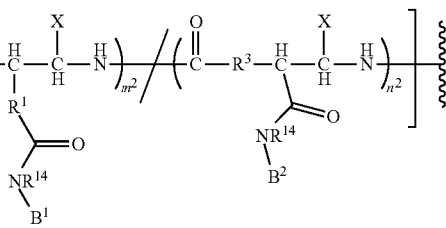

wherein,
each of $m^1$ and $n^1$ is an integer from 0 to 1000;
each of $m^2$ and $n^2$ is an integer from 0 to 1000, provided that the sum of $m^2+n^2$ is greater than 5;
the symbol "/" indicates that the units separated thereby are linked randomly or in any order;
each instance of $R^1$ and $R^3$ independently is a methylene or ethylene group;
each instance of $R^{14}$ is independently hydrogen or a $C_1$-$C_{12}$ alkyl group, alkenyl group, cycloalkyl group, or cycloalkenyl group;
each instance of X is independently a $C_1$-$C_{12}$ alkyl group, cycloalkyl group, alkenyl group, cycloalkenyl group, aryl group, heteroalkyl group, or heterocyclic group;
$A^1$ and $A^2$ are each independently a group of formula —$(CH_2)_{p1}$—[$NR^2$—$(CH_2)_{q1}$—]$_{r1}NR^2_2$;

—$(CH_2)_{p2}$—N[—$(CH_2)_{q2}$—$NR^2_2$]$_2$;

—$(CH_2)_{p3}$—N{[—$(CH_2)_{q3}$—$NR^2_2$][—$(CH_2)_{q4}$—$NR^2$—]$_{r2}R^2$}; or

—$(CH_2)_{p4}$—N{—$(CH_2)_{q5}$—N[—$(CH_2)_{q6}$—$NR^2_2$]$_2$}$_2$,

—$(CH_2)_{p4}$—N{—$(CH_2)_{q5}$—N[—$(CH_2)_{q6}$—$NR^2$—$CH_2$—CHOH—$R^5$]$_2$}$_2$;

—$(CH_2)_{p1}$—[$NR^2$—$(CH_2)_{q1}$—]$_{r1}NR^2$—$(CH_2)_2$—$R^5$;

—$(CH_2)_{p2}$—N[—$(CH_2)_{q2}$—$NR^2$—$(CH_2)_2$—$R^5$]$_2$;

—$(CH_2)_{p3}$—N{[—$(CH_2)_{q3}$—$NR^2_2$][—$(CH_2)_{q4}$—$NR^2$—]$_{r2}(CH_2)_2$—$R^5$}; or

—$(CH_2)_{p4}$—N{—$(CH_2)_{q5}$—N[—$(CH_2)_{q6}$—$NR^2$—$(CH_2)_2$—$R^5$]$_2$}$_2$, wherein p1 to p4, q1 to q6, and r1 and r2 are each independently an integer of 1 to 5; each instance of $R^2$ is independently hydrogen or a $C_1$-$C_{12}$ alkyl group, alkenyl group, cycloalkyl group, or cycloalkenyl group; each instance of $R^4$ is independently —C(O)O—, —C(O)NH—, or —S(O)(O)—; and each instance of $R^5$ is independently an alkyl group, cycloalkyl group, alkenyl group, cycloalkenyl group, aryl group, heteroalkyl group, or heterocyclic group optionally comprising from 2 to 8 tertiary amines or a substituent comprising a tissue-specific or cell-specific targeting moiety.

Accordingly, the invention also provides a polymer having the structure of Formula 4A:

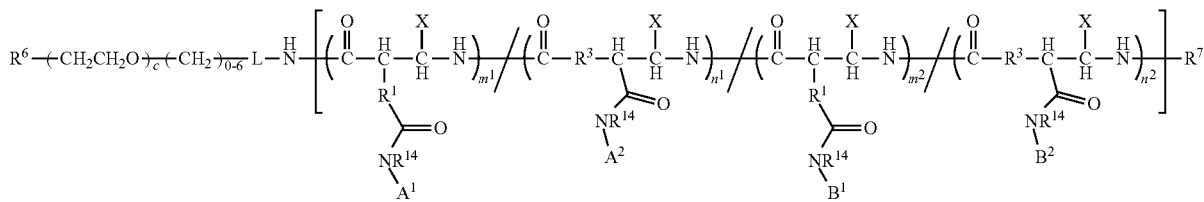

$B^1$ and $B^2$ are each independently

—$(CH_2)_{p1}$—[$NR^2$—$(CH_2)_{q1}$—]$_{r1}NR^2$—$(CH_2)_2$—$R^4$—$R^5$;

—$(CH_2)_{p2}$—N[—$(CH_2)_{q2}$—$NR^2$—$(CH_2)_2$—$R^4$—$R^5$]$_2$;

—$(CH_2)_{p3}$—N{[—$(CH_2)_{q3}$—$NR^2_2$][—$(CH_2)_{q4}$—$NR^2$—]$_{r2}(CH_2)_2$—$R^4$—$R^5$};

—$(CH_2)_{p4}$—N{—$(CH_2)_{q5}$—N[—$(CH_2)_{q6}$—$NR^2$—$(CH_2)_2$—$R^4$—$R^5$]$_2$}$_2$;

—$(CH_2)_{p1}$—[$NR^2$—$(CH_2)_{q1}$—]$_{r1}NR^2$—$CH_2$—CHOH—$R^5$;

—$(CH_2)_{p2}$—N[—$(CH_2)_{q2}$—$NR^2$—$CH_2$—CHOH—$R^5$]$_2$;

—$(CH_2)_{p3}$—N{[—$(CH_2)_{q3}$—$NR^2_2$][—$(CH_2)_{q4}$—$NR^2$—]$_{r2}$—$CH_2$—CHOH—$R^5$};

wherein,
c is an integer from 0 to 50;
L is optionally present and is a cleavable linker;
each of $m^1$ and $n^1$ is an integer from 0 to 1000;
each of $m^2$ and $n^2$ is an integer from 0 to 1000, provided that the sum of $m^2+n^2$ is greater than 5;
the symbol "/" indicates that the units separated thereby are linked randomly or in any order;
each instance of $R^1$ and $R^3$ independently is a methylene or ethylene group;
$R^6$ is hydrogen, an amino group, an aryl group, a heterocyclic group (e.g., aromatic or non-aromatic), a $C_1$-$C_{12}$ alkyl group, alkenyl group, cycloalkyl group, or cycloalkenyl group, a $C_1$-$C_{12}$ linear or branched alkyl group optionally substituted with one or more amines; or a tissue-specific or cell-specific targeting moiety;
$R^7$ is hydrogen, an aryl group, a heterocyclic group (e.g., aromatic or non-aromatic), a $C_1$-$C_{12}$ alkyl group, alkenyl group, cycloalkyl group, or cycloalkenyl group, or a $C_1$-$C_{12}$ linear or branched alkyl group optionally substituted with one or more substituents;

each instance of $R^{14}$ is independently hydrogen or a $C_1$-$C_{12}$ alkyl group, alkenyl group, cycloalkyl group, or cycloalkenyl group;

each instance of X is independently a $C_1$-$C_{12}$ alkyl group, cycloalkyl group, alkenyl group, cycloalkenyl group, aryl group, heteroalkyl group, or heterocyclic group;

$A^1$ and $A^2$ are each independently a group of formula

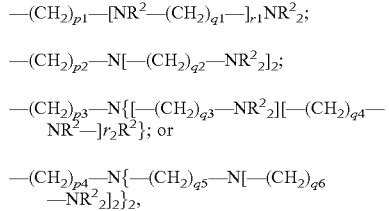

$B^1$ and $B^2$ are each independently

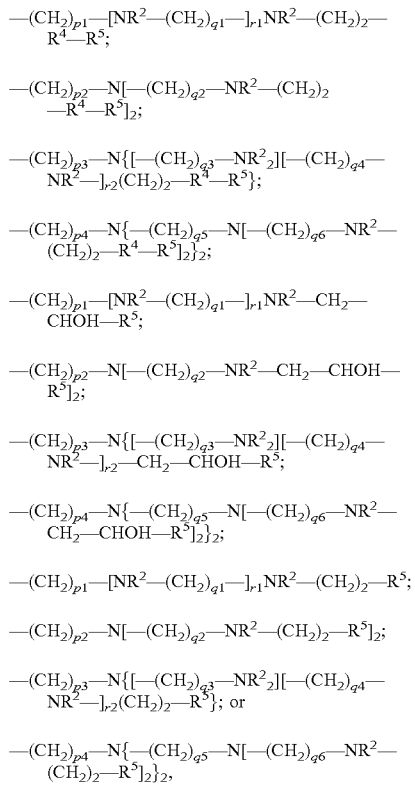

wherein p1 to p4, q1 to q6, and r1 and r2 are each independently an integer of 1 to 5; each instance of $R^2$ is independently hydrogen or a $C_1$-$C_{12}$ alkyl group, alkenyl group, cycloalkyl group, or cycloalkenyl group; each instance of $R^4$ is independently —C(O)O—, —C(O)NH—, or —S(O)(O)—; and each instance of $R^5$ is independently an alkyl group, cycloalkyl group, alkenyl group, cycloalkenyl group, aryl group, heteroalkyl group, or heterocyclic group optionally comprising from 2 to 8 tertiary amines or a substituent comprising a tissue-specific or cell-specific targeting moiety.

According to Formula 4 and 4A, each of $m^1$ and $n^1$ is an integer from 0 to 1000, such as 0-500, or 0-100. Furthermore, each of $m^2$ and $n^2$ is an integer from 0 to 1000, such as 0-500, or 0-100, provided that the sum of $m^2+n^2$ is greater than 5. In other words, the polymer comprises at least some monomeric units of comprising groups $B^1$ and/or $B^2$, herein referred to collectively as the "B monomers." In some embodiments, $m^1$ and $n^1$ are zero, such that the polymer comprises no $A^1$ or $A^2$ groups. In other embodiments, the polymer comprises some $A^1$ and/or $A^2$ groups and some $B^1$ and/or $B^2$ groups. In such embodiments, the ratio of $(m^1+n^1)/(m^2+n^2)$ is about 20 or less (e.g., about 10 or less, about 5 or less, about 2 or less, or even about 1 or less). Also, in some embodiments, the ratio of $(m^1+n^1)/(m^2+n^2)$ is about 0.2 or more, such as about 0.5 or more.

Thus, in the structure of Formula 3, 3A, 4, and 4A, the monomers (which can be referred to by their respective side chains $A^1$, $A^2$, $B^1$, and $B^2$) can be arranged randomly or in any order. Thus, $m^1$, $n^1$, $m^2$, and $n^2$ merely denote the number of the respective monomers that appear in the chain overall, and not necessarily represent blocks of those monomers, although blocks or stretches of a given monomer might be present in some embodiments. For instance, the structure of Formula 1 can comprise the monomers in the order -$A^1$-$A^2$-$B^1$-$B^2$-, -$A^2$-$A^1$-$B^2$-$B^1$-, -$A^1$-$B^1$-$A^2$-$B^2$—, etc. In some embodiments, the polyaspartamide backbone will be arranged in an alpha/beta configuration, such that the "1" and "2" monomers will alternate (e.g., -$A^1$-$A^2$-$B^1$-$B^2$-, -$A^2$-$A^1$-$B^2$-$B^1$-, -$A^1$-$B^2$-$B^1$-$A^2$-, -$A^2$-$B^1$-$B^2$-$A^1$-, -$B^1$-$A^2$-$B^1$-$A^2$-, etc.). However, the "A" and "B" sidechains (e.g., $A^1$/$A^2$ and $B^1$/$B^2$) can be dispersed randomly throughout the polymer backbone.

By way of further illustration, the polymer could instead be described as Formula 4.1:

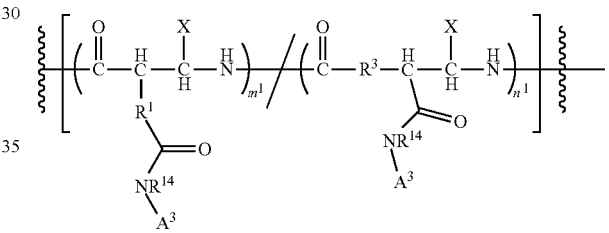

or, where the backbone is in an alpha, beta configuration, as Formula 4.2:

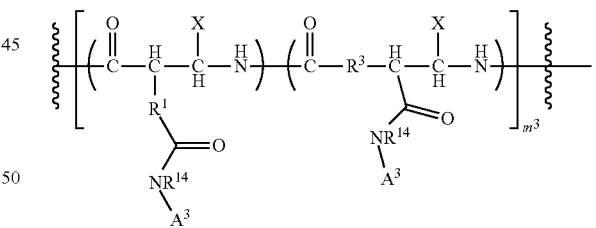

wherein,
each of $m^1$ and $n^1$ is an integer from 0 to 1000;
$m^3$ is an integer from 5-2000 (e.g., 5-1000, 5-500, 5-100, 25-2000, 25-500, 25-100, 50-2000, 50-1000, 50-500, or 50-100);
the symbol "/" indicates that the units separated thereby are linked randomly or in any order;
each instance of $R^1$ and $R^3$ independently is a methylene or ethylene group; each instance of $R^{14}$ is independently hydrogen or a $C_1$-$C_{12}$ alkyl group, alkenyl group, cycloalkyl group, or cycloalkenyl group;
each instance of X is independently a $C_1$-$C_{12}$ alkyl group, cycloalkyl group, alkenyl group, cycloalkenyl group, aryl group, heteroalkyl group, or heterocyclic group;

each $A^3$ independently is a group of formula

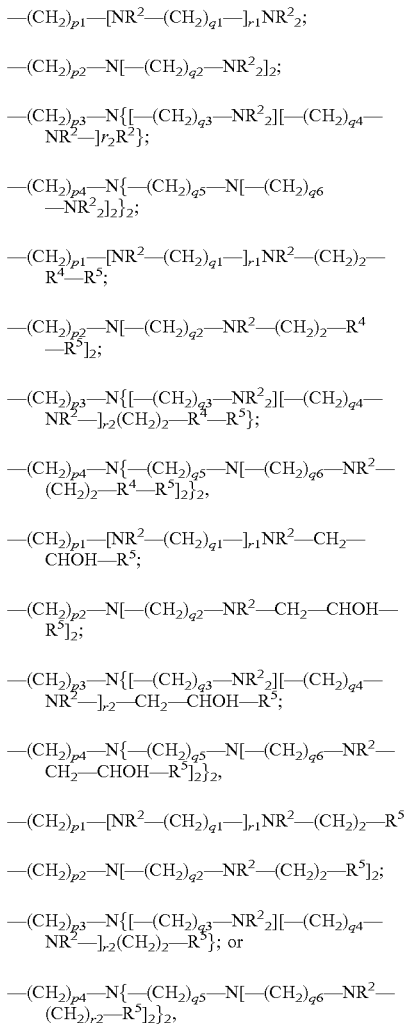

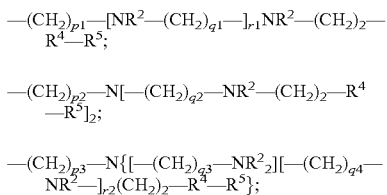

wherein p1 to p4, q1 to q6, and r1 and r2 are each independently an integer of 1 to 5; each instance of $R^2$ is independently hydrogen or a $C_1$-$C_{12}$ alkyl group, alkenyl group, cycloalkyl group, or cycloalkenyl group; each instance of $R^4$ is independently —C(O)O—, —C(O)NH—, or —S(O)(O)—; and each instance of $R^5$ is independently an alkyl group, cycloalkyl group, alkenyl group, cycloalkenyl group, aryl group, heteroalkyl group, or heterocyclic group optionally comprising from 2 to 8 tertiary amines or a substituent comprising a tissue-specific or cell-specific targeting moiety;

provided that at least about 5% (such as at least about 10%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or even 100%) of the $A^3$ groups are selected from

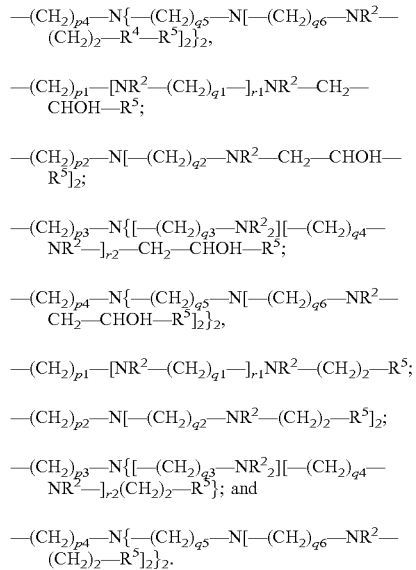

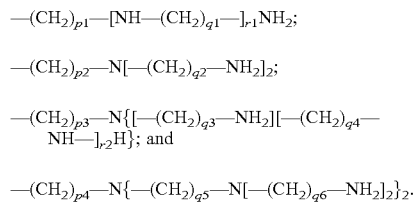

In still other embodiments, the polymer has some or even a majority of $A^3$ groups (at least about 5%, at least about 10%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%) that are selected from —(CH$_2$)$_{p1}$—[NH—(CH$_2$)$_{q1}$—]$_{r1}$NH$_2$;

—(CH$_2$)$_{p2}$—N[—(CH$_2$)$_{q2}$—NH$_2$]$_2$;

—(CH$_2$)$_{p3}$—N{[—(CH$_2$)$_{q3}$—NH$_2$][—(CH$_2$)$_{q4}$—NH—]$_{r2}$H}; and —(CH$_2$)$_{p4}$—N{—(CH$_2$)$_{q5}$—N[—(CH$_2$)$_{q6}$—NH$_2$]$_2$}$_2$.

In the polymer structures, $R^{3a}$ and $R^{3b}$ are each independently a methylene or ethylene group. In some embodiments, $R^{3a}$ is an ethylene group and $R^{3b}$ is a methylene group; or $R^{3a}$ is a methylene group and $R^{3b}$ is an ethylene group. In certain embodiments, $R^{3a}$ and $R^{3b}$ are each an ethylene group. In preferred embodiments, $R^{3a}$ and $R^{3b}$ are each a methylene group.

Groups $A^1$ and $A^2$ are independently selected and, therefore, can be the same or different from one another. Similarly, groups $B^1$ and $B^2$ are independently selected and can be the same or different from one another. Furthermore, each instance of $A^3$ can be the same or different from other $A^3$ groups.

In groups $A^1$, $A^2$, $A^3$, $B^1$, and $B^2$, integers p1 to p4 (i.e., p1, p2, p3, and p4), q1 to q6 (i.e., q1, q2, q3, q4, q5, and q6), and r1 and r2 are each independently an integer of 1 to 5 (e.g., 1, 2, 3, 4, or 5). In some embodiments, p1 to p4 (i.e., p1, p2, p3, and p4), q1 to q6 (i.e., q1, q2, q3, q4, q5, and q6), and/or r1 and r2 are each independently an integer of 1 to 3 (e.g., 1, 2, or 3). In certain embodiments, p1 to p4 (i.e., p1, p2, p3, and p4) and/or q1 to q6 (i.e., q1, q2, q3, q4, q5, and q6) are each 2. In some embodiments, p1 to p4 (i.e., p1, p2, p3, and p4) and/or q1 to q6 (i.e., q1, q2, q3, q4, q5, and q6) are each 2, and r1 and r2 are each 1.

In some embodiments of Formula 3, Formula 3A, Formula 4, or Formula 4A, each of $A^1$ and $A^2$ is a group of formula —(CH$_2$)$_{p1}$—[NH—(CH$_2$)$_{q1}$—]$_{r1}$NH$_2$, such as a group —(CH$_2$)$_2$—NH—(CH$_2$)$_2$—NH$_2$. In addition, or alternatively, each of $B^1$ and $B^2$ is a group of formula —$(CH_2)_{p1}$—[NH—$(CH_2)_{q1}$—]$_{r1}$NH—$(CH_2)_2$—$R^4$—$R^5$, such as a group —$(CH_2)_2$—NH—$(CH_2)_2$—NH—$(CH_2)_2$—$R^4$—$R^5$, or a group —$(CH_2)_2$—NH—$(CH_2)_2$—NH—$(CH_2)_2$—C(O)—O—$R^5$.

In some embodiments of Formula 4.1 or 4.2, $A^3$ is a group of the formula —$(CH_2)_{p1}$—[NH—$(CH_2)_{q1}$—]$_{r1}$NH$_2$, such as a group —$(CH_2)_2$—NH—$(CH_2)_2$—NH$_2$; or a group of formula —$(CH_2)_{p1}$—[NH—$(CH_2)_{q1}$—]$_{r1}$NH—$(CH_2)_2$—$R^4$—$R^5$, such as a group —$(CH_2)_2$—NH—$(CH_2)_2$—NH—$(CH_2)_2$—$R^4$—$R^5$, or a group —$(CH_2)_2$—NH—$(CH_2)_2$—NH—$(CH_2)_2$—C(O)—O—$R^5$; provided that at least about 5% (such as at least about 10%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or even 100%) of the $A^3$ groups are —$(CH_2)_{p1}$—[NH—$(CH_2)_{q1}$—]$_{r1}$NH—$(CH_2)_2$—$R^4$—$R^5$, such as a group —$(CH_2)_2$—NH—$(CH_2)_2$—NH—$(CH_2)_2$—$R^4$—$R^5$, or a group —$(CH_2)_2$—NH—$(CH_2)_2$—NH—$(CH_2)_2$—C(O)—O—$R^5$. Additionally, in some embodiments, the polymer has some or even a majority of $A^3$ groups (at least about 5%, at least about 10%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%) that are —$(CH_2)_{p1}$—[NH—$(CH_2)_{q1}$—]$_{r1}$NH—$(CH_2)_2$—$R^4$—$R^5$, such as a group —$(CH_2)_2$—NH—$(CH_2)_2$—NH—$(CH_2)_2$—$R^4$—$R^5$, or a group —$(CH_2)_2$—NH—$(CH_2)_2$—NH—$(CH_2)_2$—C(O)—O—$R^5$.

The polymer can be any suitable polymer, provided the polymer comprises the foregoing polymer structure. In some embodiments, the polymer is a block copolymer comprising a polymer block having the structure of Formula 3, 3A, 4, 4.1, 4.2, or 4A and one or more other polymer blocks (e.g., an ethylene oxide subunit, or a propylene oxide subunit). In other embodiments, the structure of Formula 3, 3A, 4, 4.1, 4.2, or 4A is the only polymeric unit of the polymer. In certain embodiments, the polymer further comprises a substituent comprising a tissue-specific or cell-specific targeting moiety.

In some embodiments, the polymer has structure of Formula 3B:

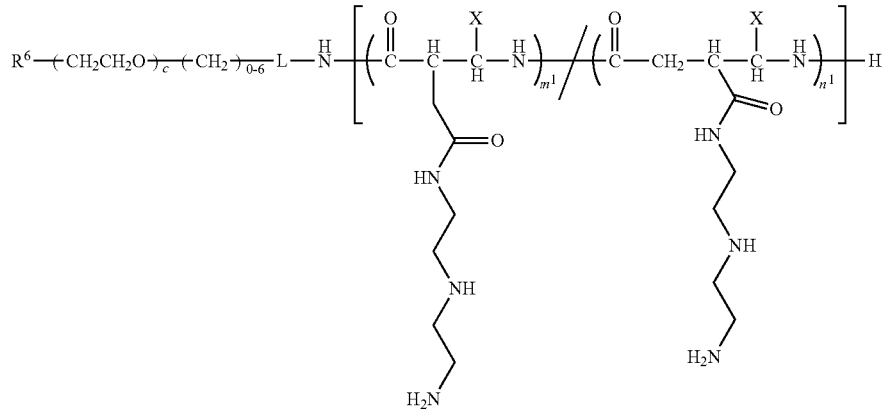

wherein,
c is an integer from 0 to 50;
L is optionally present and is a cleavable linker;
each of $m^1$ and $n^1$ is an integer from 0 to 1000; provided that the sum of $m^1+n^1$ is greater than 5;
the symbol "/" indicates that the units separated thereby are linked randomly or in any order;
$R^6$ is hydrogen, an amino group, an aryl group, a heterocyclic group (e.g., aromatic or non-aromatic), a $C_1$-$C_{12}$ alkyl group, alkenyl group, cycloalkyl group, or cycloalkenyl group, a $C_1$-$C_{12}$ linear or branched alkyl group optionally substituted with one or more amines; or a tissue-specific or cell-specific targeting moiety; and
each instance of X is independently a $C_1$-$C_{12}$ alkyl group, cycloalkyl group, alkenyl group, cycloalkenyl group, aryl group, heteroalkyl group, or heterocyclic group, or Formula 4B:

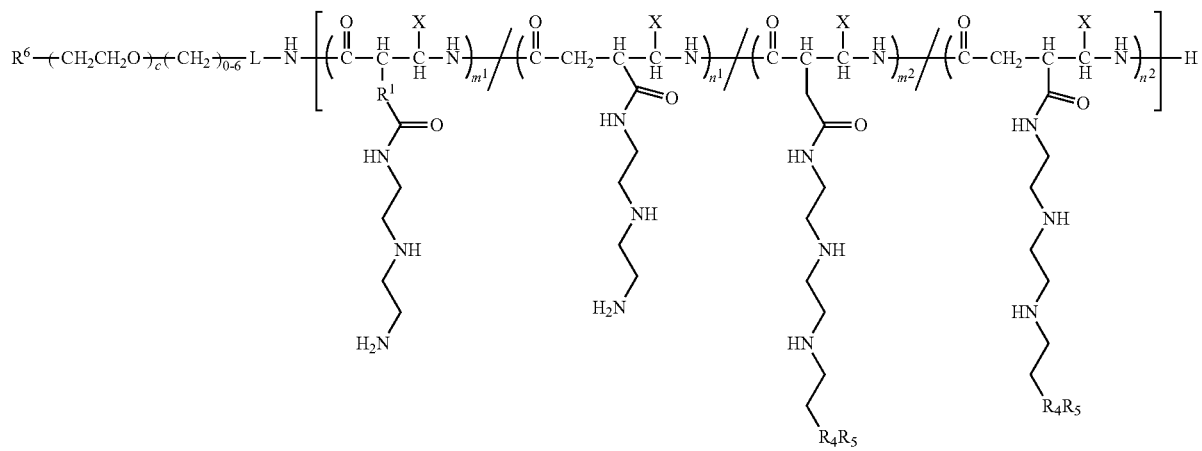

wherein, c is an integer from 0 to 50;

L is optionally present and is a cleavable linker;

each of $m^1$ and $n^1$ is an integer from 0 to 1000;

each of $m^2$ and $n^2$ is an integer from 0 to 1000, provided that the sum of $m^2+n^2$ is greater than 5;

the symbol "/" indicates that the units separated thereby are linked randomly or in any order;

$R^6$ is hydrogen, an amino group, an aryl group, a heterocyclic group (e.g., aromatic or non-aromatic), a $C_1$-$C_{12}$ alkyl group, alkenyl group, cycloalkyl group, or cycloalkenyl group, a $C_1$-$C_{12}$ linear or branched alkyl group optionally substituted with one or more amines; or a tissue-specific or cell-specific targeting moiety;

each instance of X is independently a $C_1$-$C_{12}$ alkyl group, cycloalkyl group, alkenyl group, cycloalkenyl group, aryl group, heteroalkyl group, or heterocyclic group;

each instance of $R^4$ is independently —C(O)O—, —C(O)NH—, or —S(O)(O)—; and each instance of $R^5$ is independently an alkyl group, cycloalkyl group, alkenyl group, cycloalkenyl group, aryl group, heteroalkyl group, or heterocyclic group optionally comprising from 2 to 8 tertiary amines or a substituent comprising a tissue-specific or cell-specific targeting moiety.

In certain embodiments, the polymer has structure of Formula 3C:

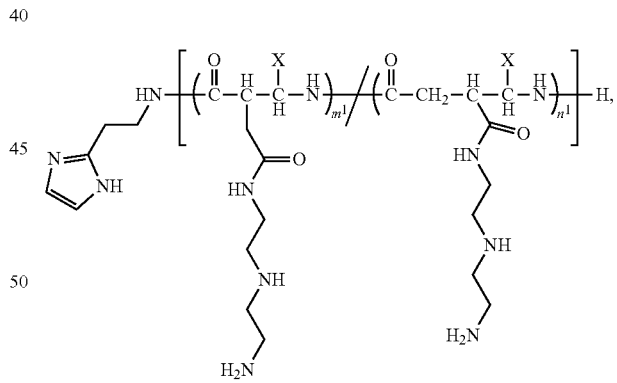

wherein each of $m^1$ and $n^1$ is an integer from 0 to 1000; provided that the sum of $m^1+n^1$ is greater than 5, the symbol "/" indicates that the units separated thereby are linked randomly or in any order; and each instance of X is independently a $C_1$-$C_{12}$ alkyl group, cycloalkyl group, alkenyl group, cycloalkenyl group, aryl group, heteroalkyl group, or heterocyclic group, or Formula 4C:

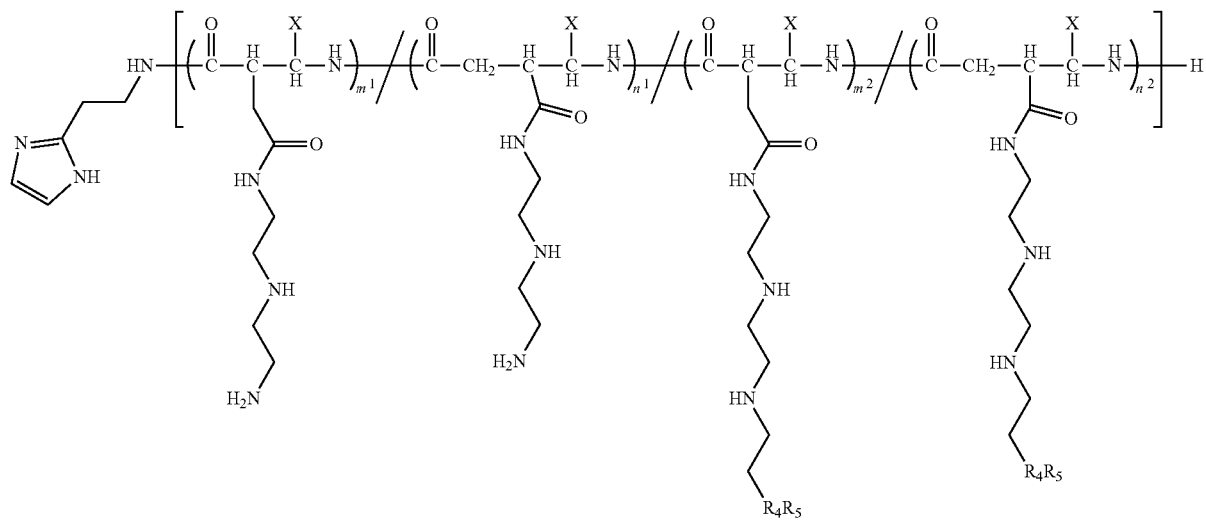

wherein,
- each of $m^1$ and $n^1$ is an integer from 0 to 1000;
- each of $m^2$ and $n^2$ is an integer from 0 to 1000, provided that the sum of $m^2+n^2$ is greater than 5;
- the symbol "/" indicates that the units separated thereby are linked randomly or in any order;
- each instance of X is independently a $C_1$-$C_{12}$ alkyl group, cycloalkyl group, alkenyl group, cycloalkenyl group, aryl group, heteroalkyl group, or heterocyclic group;
- each instance of $R^4$ is independently —C(O)O—, —C(O)NH—, or —S(O)(O)—; and
- each instance of $R^5$ is independently an alkyl group, cycloalkyl group, alkenyl group, cycloalkenyl group, aryl group, heteroalkyl group, or heterocyclic group optionally comprising from 2 to 8 tertiary amines or a substituent comprising a tissue-specific or cell-specific targeting moiety.

In any of the foregoing polymers, each instance of X is independently a $C_1$-$C_{12}$ (e.g., $C_1$-$C_{12}$, $C_3$-$C_{12}$, $C_1$-$C_8$, or $C_3$-$C_8$) alkyl group, cycloalkyl group, alkenyl group, cycloalkenyl group, aryl group, heteroalkyl group, or heterocyclic group, any of which can be straight chain or branched. In some embodiments, each instance of X is the same. Examples of X groups include, for instance, a C4, C5, C6, C7, C8, C9, or C10 alkyl or a 4-, 5-, 6-, 7-, 8-, 9-, 10-, 11-, or 12-member heteroalkyl group comprising any suitable number of heteroatoms (e.g., 1, 2, or 3 nitrogen, sulfur, or oxygen atoms).

Any of the forgoing polymers can comprise a tissue-specific or cell-specific targeting moiety at a position indicated in the described formulas, or the polymers can be otherwise modified to include a tissue-specific or cell-specific targeting moiety. The tissue-specific or cell-specific targeting moiety can be any small molecule, protein (e.g., antibody or antigen), amino acid sequence, sugar, oligonucleotide, metal-based nanoparticle, or combination thereof, capable of recognizing (e.g., specifically binding) a given target tissue or cell (e.g., specifically binding a particular ligand, receptor, or other protein or molecule that allows the targeting moiety to discriminate between the target tissue or cell and other non-target tissues or cells). In some embodiments, the tissue-specific or cell-specific targeting moiety is a receptor for a ligand. In some embodiments, the tissue-specific or cell-specific targeting moiety is a ligand for a receptor.

The tissue-specific or cell-specific targeting moiety can be used to target any desired tissue or cell type. In some embodiments, the tissue-specific or cell-specific targeting moiety localizes the polymer to tissues of the peripheral nervous system, the central nervous system, liver, muscle (e.g., cardiac muscle), lung, bone (e.g., hematopoietic cells), or the eye of the subject. In certain embodiments, the tissue-specific or cell-specific targeting moiety localizes the polymer to tumor cells. For example, the tissue-specific or cell-specific targeting moiety can be a sugar that binds to a receptor on a specific tissue or cell.

In some embodiments, the tissue-specific or cell-specific targeting moiety is:

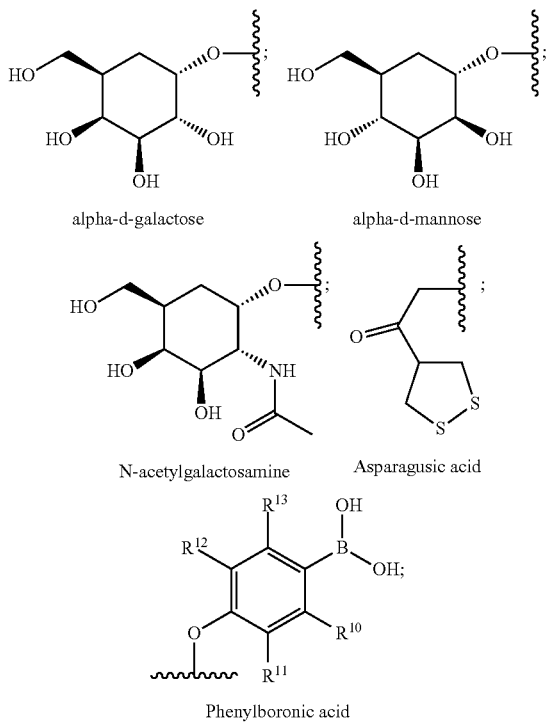

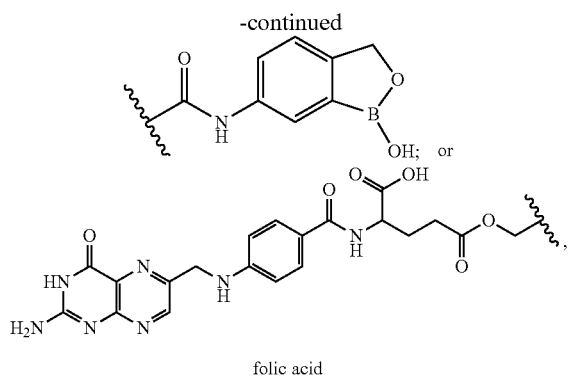

folic acid wherein each of $R^{10}$, $R^{11}$, $R^{12}$, and $R^{13}$ is independently hydrogen, halogen, $C_1$-$C_4$ alkyl, or $C_1$-$C_4$ alkoxy, optionally substituted with one or more amino groups. The specified tissue-specific or cell-specific targeting moieties can be chosen to localize the polymer to a tissue described herein. For example, alpha-d-mannose can be used to localize the polymer to the peripheral nervous system, the central nervous system, or immune cells, alpha-d-galactose and N-acetylglucosamine can be used to localize the polymer to liver hepatocytes, and folic acid can be used to localize the polymer to tumor cells.

The polymer can exist as any suitable structure type. For example, the polymer can exist as an alternating polymer, random polymer, block polymer, graft polymer, linear polymer, branched polymer, cyclic polymer, or a combination thereof. In certain embodiments, the polymer is a random polymer, block polymer, graft polymer, or a combination thereof.

Typically, the polymer is cationic (i.e., positively charged at pH 7 and 23° C.). As used herein, "cationic" polymers refer to polymers having an overall net positive charge, whether the polymer comprises only cationic monomer units or a combination of cationic monomer units and non-ionic or anionic monomer units.

In certain embodiments, the polymer has a weight average molecular weight of from about 10 kDa to about 2,000 kDa. The polymer can have a weight average molecular weight of about 2,000 kDa or less, for example, about 1,800 kDa or less, about 1,600 kDa or less, about 1,400 kDa or less, about 1,200 kDa or less, about 1,000 kDa or less, about 900 kDa, or less, about 800 kDa, or less, about 700 kDa or less, about 600 kDa or less, about 500 kDa or less, about 100 kDa or less, or about 50 kDa or less. Alternatively, or in addition, the polymer can have a weight average molecular weight of about 10 kDa or more, for example, about 50 kDa or more, about 100 kDa or more, about 200 kDa or more, about 300 kDa or more, or about 400 kDa or more. Thus, the polymer can have a weight average molecular weight bounded by any two of the aforementioned endpoints. For example, the polymer can have a weight average molecular weight of from about 10 kDa to about 50 kDa, from about, from about 10 kDa to about 100 kDa, from about 10 kDa to about 500 kDa, from about 50 kDa to about 500 kDa, from about 100 kDa to about 500 kDa, from about 200 kDa to about 500 kDa, from about 300 kDa to about 500 kDa, from about 400 kDa to about 500 kDa, from about 400 kDa to about 600 kDa, from about 400 kDa to about 700 kDa, from about 400 kDa to about 800 kDa, from about 400 kDa to about 900 kDa, from about 400 kDa to about 1,000 kDa, from about 400 kDa to about 1,200 kDa, from about 400 kDa to about 1,400 kDa, from about 400 kDa to about 1,600 kDa, from about 400 kDa to about 1,800 kDa, from about 400 kDa to about 2,000 kDa, from about 200 kDa to about 2,000 kDa, from about 500 kDa to about 2,000 kDa, or from about 800 kDa to about 2,000 kDa.

The weight average molecular weight can be determined by any suitable technique. Generally, the weight average molecular weight is determined using size exclusion chromatography equipped with a column, selected from TSKgel Guard, GMPW, GMPW, G1000PW, and a Waters 2414 (Waters Corporation, Milford, Massachusetts) refractive index detector. Moreover, the weight average molecular weight is determined from calibration with polyethylene oxide/polyethylene glycol standards ranging from 150-875,000 Daltons.

Methods of Preparation

The invention also provides a method of preparing a polymer described herein.

In some embodiments, the method comprises preparing a polymer comprising a structure of Formula 1 from a compound of Formula A:

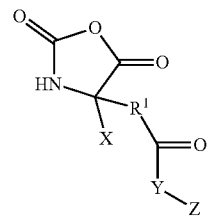

wherein,
$R^1$ is a methylene or ethylene group;
X is a $C_1$-$C_{12}$ alkyl group, cycloalkyl group, alkenyl group, cycloalkenyl group, aryl group, heteroalkyl group, or heterocyclic group;
Y is —$NR^{14}$— or —O—, wherein $R^{14}$ is hydrogen or a $C_1$-$C_{12}$ alkyl group, alkenyl group, cycloalkyl group, or cycloalkenyl group;
Z is $A^1$, or an alkyl group, cycloalkyl group, alkenyl group, cycloalkenyl group, aryl group, arylalkyl group, heteroalkyl group, or heterocyclic group optionally comprising from 2 to 8 tertiary amines or a substituent comprising a tissue-specific or cell-specific targeting moiety;
$A^1$ is a group of formula

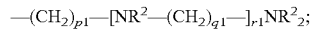

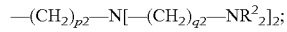

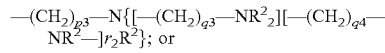

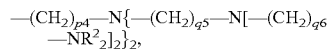

wherein p1 to p4, q1 to q6, and r1 and r2 are each independently an integer of 1 to 5; and each instance of $R^2$ is independently hydrogen or a $C_1$-$C_{12}$ alkyl group, alkenyl group, cycloalkyl group, or cycloalkenyl group.

Generally, the method comprising forming a polymer comprising a structure of Formula 1 from a compound of Formula A includes a ring-opening polymerization of the compound Formula A. The ring-opening polymerization of the compound of Formula A can be initiated by any suitable method (e.g., temperature, light, catalyst, compound, etc.).

In some embodiments, the ring-opening polymerization of the compound of Formula A is initiated with an amine-containing compound.

In certain embodiments, the ring-opening polymerization of the compound of Formula A is initiated with an amine-containing compound of the formula:

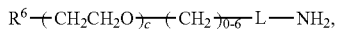

wherein,
c is an integer from 0 to 50;
L is optionally present and is a cleavable linker; and
$R^6$ is hydrogen, an amino group, an aryl group, a heterocyclic group (e.g., aromatic or non-aromatic), a $C_1$-$C_{12}$ alkyl group, alkenyl group, cycloalkyl group, or cycloalkenyl group, a $C_1$-$C_{12}$ linear or branched alkyl group optionally substituted with one or more amines; or a tissue-specific or cell-specific targeting moiety. In preferred embodiments, the amine-containing compound is

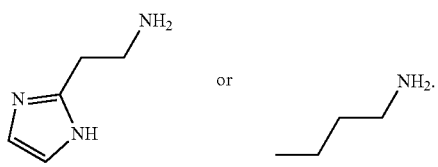

In some embodiments, in the compound of Formula A, Y is —O—, and Z is an alkyl group, cycloalkyl group, alkenyl group, cycloalkenyl group, aryl group, arylalkyl group, heteroalkyl group, or heterocyclic group optionally comprising from 2 to 8 tertiary amines. In some embodiments, Z is an arylalkyl group, such as a benzyl. The method of producing a polymer of Formula 1, then, further comprises, after ring opening polymerization, treating the resulting intermediate polymer with a compound of the formula $NHR^{14}$-$A^1$, wherein $A^1$ is as defined with respect to Formula 1. The compound of the formula $NHR^{14}$-$A^1$ is optionally diethyleneamine triamine.

Accordingly, said method can be used to prepare a polymer, or a polymer comprising a structure of Formula 1, 1A, 1B, 1C, 2, 2.1, 2A, 2B, or 2C, as well as any and all embodiments thereof as described with respect to the polymers of the invention, from a compound of Formula A.

In some embodiments, the method comprising preparing a polymer comprising a structure of Formula 3 from a compound of Formula B:

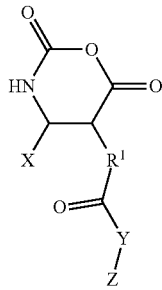

wherein,
$R^1$ is a methylene or ethylene group;
X is a $C_1$-$C_{12}$ alkyl group, cycloalkyl group, alkenyl group, cycloalkenyl group, aryl group, heteroalkyl group, or heterocyclic group;
Y is —$NR^{14}$— or —O—, wherein $R^{14}$ is hydrogen or a $C_1$-$C_{12}$ alkyl group, alkenyl group, cycloalkyl group, or cycloalkenyl group;
Z is $A^1$, or an alkyl group, cycloalkyl group, alkenyl group, cycloalkenyl group, aryl group, arylalkyl group, heteroalkyl group, or heterocyclic group optionally comprising from 2 to 8 tertiary amines or a substituent comprising a tissue-specific or cell-specific targeting moiety;
$A^1$ is a group of formula

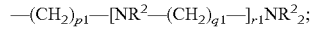

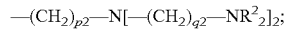

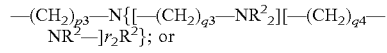

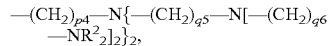

wherein p1 to p4, q1 to q6, and r1 and r2 are each independently an integer of 1 to 5; and each instance of $R^2$ is independently hydrogen or a $C_1$-$C_{12}$ alkyl group, alkenyl group, cycloalkyl group, or cycloalkenyl group.

Generally, the method comprising forming a polymer comprising a structure of Formula 3 from a compound of Formula B includes a ring-opening polymerization of the compound Formula B. The ring-opening polymerization of the compound of Formula B can be initiated by any suitable method (e.g., temperature, light, catalyst, compound, etc.). In some embodiments, the ring-opening polymerization of the compound of Formula B is initiated with an amine-containing compound.

In certain embodiments, the ring-opening polymerization of the compound of Formula B is initiated with an amine-containing compound of the formula:

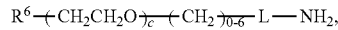

wherein,
c is an integer from 0 to 50;
L is optionally present and is a cleavable linker; and
$R^6$ is hydrogen, an amino group, an aryl group, a heterocyclic group (e.g., aromatic or non-aromatic), a $C_1$-$C_{12}$ alkyl group, alkenyl group, cycloalkyl group, or cycloalkenyl group, a $C_1$-$C_{12}$ linear or branched alkyl group optionally substituted with one or more amines; or a tissue-specific or cell-specific targeting moiety. In preferred embodiments, the amine-containing compound is

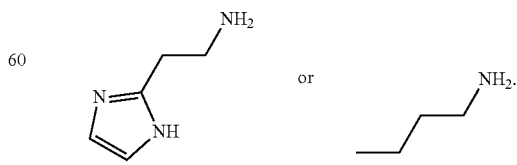

In some embodiments, in the compound of Formula B, Y is —O—, and Z is an alkyl group, cycloalkyl group, alkenyl group, cycloalkenyl group, aryl group, arylalkyl group, heteroalkyl group, or heterocyclic group optionally comprising from 2 to 8 tertiary amines. In some embodiments, Z is an arylalkyl group, such as a benzyl. The method of producing a polymer of Formula 1, then, further comprises, after ring opening polymerization, treating the resulting intermediate polymer with a compound of the formula $NHR^{14}$-$A^1$, wherein $A^1$ is as defined with respect to Formula 1. The compound of the formula $NHR^{14}$-$A^1$ is optionally diethyleneamine triamine.

Accordingly, said method can be used to prepare a polymer, or a polymer comprising a structure of Formula 3, 3A, 3B, 3C, 4, 4.1, 4.2, 4A, 4B, or 4C, as well as any and all embodiments thereof as described with respect to the polymers of the invention, from a compound of Formula B.

The polymers, or polymers comprising a structure of Formulas 1, 1A, 1B, 1C, 3, 3A, 3B, and 3C can be further modified to form polymers, or polymers comprising a structure of Formulas 2 (e.g., a polymer of Formula 2.1), 2A, 2B, 2C, 4 (e.g., a polymer of Formula 4.1 or 4.2), 4A, 4B, and 4C, respectively.

In some embodiments, the method comprises preparing a polymer comprising a structure of Formula 2 (e.g., a polymer of Formula 2.1) from a polymer comprising a structure of Formula 1 by modifying at least a portion of groups designated $A^1$ (or group $A^3$ of the polymer of Formula 2.1) to produce groups designated $B^1$ (or group $A^3$ of the polymer of Formula 2.1). The polymer comprising a structure of Formula 2 produced by the method can be any polymer of Formula 2, including Formulas 2, 2.1, 2A, 2B, and 2C, as well as any and all embodiments thereof as described with respect to the polymer of the invention. Accordingly, in certain embodiments, the method comprises preparing a polymer comprising a structure of Formula 2A from a polymer comprising a structure of Formula 1A by modifying at least a portion of groups designated $A^1$ to produce groups designated $B^1$.

In some embodiments, the method comprises preparing a polymer comprising a structure of Formula 4 (e.g., a polymer of Formula 4.1 or 4.2) from a polymer comprising a structure of Formula 3 by modifying at least a portion of groups designated $A^1$ and/or $A^2$ (or group $A^3$ of the polymer of Formula 4.1 or 4.2) to produce groups designated $B^1$ and/or $B^2$ (or group $A^3$ of the polymer of Formula 4.1 or 4.2). The polymer comprising a structure of Formula 4 produced by the method can be any polymer of Formula 4, including Formulas 4, 4.1, 4.2, 4A, 4B, and 4C, as well as any and all embodiments thereof as described with respect to the polymer of the invention. Accordingly, in certain embodiments, the method comprises preparing a polymer comprising a structure of Formula 4A from a polymer comprising a structure of Formula 3A by modifying at least a portion of groups designated $A^1$ and/or $A^2$ to produce groups designated $B^1$ and/or $B^2$.

The methods of modifying polymers, or polymers comprising a structure of Formulas 1, 1A, 1B, 1C, 3, 3A, 3B, and 3C to produce polymers of Formulas 2 (e.g., a polymer of Formula 2.1), 2A, 2B, 2C, 4 (e.g., a polymer of Formula 4.1 or 4.2), 4A, 4B, and 4C, respectively, comprise modifying at least a portion of groups designated $A^1$ and/or $A^2$ to produce groups designated $B^1$ and/or $B^2$. As described herein, $A^1$ and/or $A^2$ are each independently a group of formula

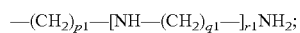

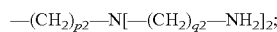

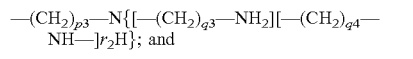

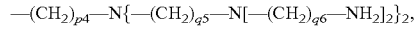

wherein p1 to p4, q1 to q6, and r1 and r2 are each independently an integer of 1 to 5; and
$B^1$ and/or $B^2$ are each independently

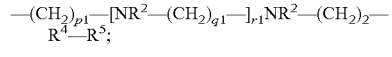

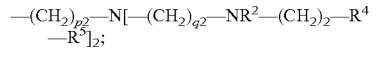

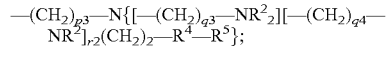

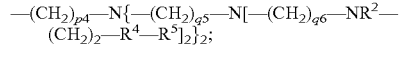

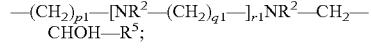

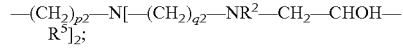

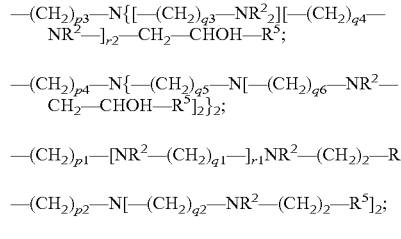

wherein p1 to p4, q1 to q6, and r1 and r2 are each independently an integer of 1 to 5; each instance of $R^2$ is independently hydrogen or a $C_1$-$C_{12}$ alkyl group, alkenyl group, cycloalkyl group, or cycloalkenyl group; each instance of $R^4$ is independently —C(O)O—, —C(O)NH—, or —S(O)(O)—; and each instance of $R^5$ is independently an alkyl group, cycloalkyl group, alkenyl group, cycloalkenyl group, aryl group, heteroalkyl group, or heterocyclic group optionally comprising from 2 to 8 tertiary amines or a substituent comprising a tissue-specific or cell-specific targeting moiety.

The groups designated $A^1$ and/or $A^2$ (or group $A^3$ of the polymer of Formula 2.1, 4.1, or 4.2) can be modified by any suitable means to produce groups designated $B^1$ and/or $B^2$ (or group $A^3$ of the polymer of Formula 2.1, 4.1, or 4.2). For example, the groups designated $A^1$ and/or $A^2$ (or group $A^3$ of the polymer of Formula 2.1, 4.1, or 4.2) can be modified by a Michael addition reaction, an epoxide opening, or a displacement reaction. In preferred embodiments, the groups designated $A^1$ and/or $A^2$ (or group $A^3$ of the polymer of Formula 2.1, 4.1, or 4.2) are modified by a Michael addition reaction.

In one embodiment, groups $A^1$ and/or $A^2$ (or group $A^3$ of the polymer of Formula 2.1, 4.1, or 4.2) of the polymer are modified by a Michael addition reaction between the polymer and an α,β-unsaturated carbonyl compound. As used herein, the term "Michael addition" refers to a nucleophilic addition of a nucleophile of the polymer (e.g., a carbanion, an oxygen anion, a nitrogen anion, an oxygen atom, a nitrogen atom, or a combination thereof) to an α,β-unsaturated carbonyl compound. Accordingly, the Michael addition reaction is between the polymer and an α,β-unsaturated carbonyl compound. In some embodiments, the nucleophile of the polymer is a nitrogen anion, a nitrogen atom, or a combination thereof.

The α,β-unsaturated carbonyl compound can be any α,β-unsaturated carbonyl compound capable of accepting a Michael addition from a nucleophile. In some embodiments, the α,β-unsaturated carbonyl compound is an acrylate, an acrylamide, a vinyl sulfone, or a combination thereof. Accordingly, the Michael addition reaction can be between the polymer and an acrylate, an acrylamide, a vinyl sulfone, or a combination thereof. Thus, in some embodiments, the method comprises contacting the polymer and an acrylate; contacting the polymer and an acrylamide; or contacting the polymer and a vinyl sulfone. In preferred embodiments, the method comprises contacting the polymer and an acrylate.

In embodiments where the groups designated $A^1$ and/or $A^2$ (or group $A^3$ of the polymer of Formula 2.1, 4.1, or 4.2) are modified by a Michael addition reaction, they produce groups designated $B^1$ and/or $B^2$ (or group $A^3$ of the polymer of Formula 4.1 or 4.2) of the formula:

—(CH$_2$)$_{p1}$—[NR$^2$—(CH$_2$)$_{q1}$—]$_{r1}$NR$^2$—(CH$_2$)$_2$—
R$^4$—R$^5$;

—(CH$_2$)$_{p2}$—N[—(CH$_2$)$_{q2}$—NR$^2$—(CH$_2$)$_2$
—R$^4$—R$^5$]$_2$;

—(CH$_2$)$_{p3}$—N{[—(CH$_2$)$_{q3}$—NR$^2$]$_2$][—(CH$_2$)$_{q4}$—
NR$^2$—]$_{r2}$(CH$_2$)$_2$—R$^4$—R$^5$};

—(CH$_2$)$_{p4}$—N{—(CH$_2$)$_{q5}$—N[—(CH$_2$)$_{q6}$—NR$^2$—
(CH$_2$)$_2$—R$^4$—R$^5$]$_2$}$_2$, wherein p1 to p4, q1 to q6, and r1 and r2 are each independently an integer of 1 to 5; each instance of $R^2$ is independently hydrogen or a $C_1$-$C_{12}$ alkyl group, alkenyl group, cycloalkyl group, or cycloalkenyl group; each instance of $R^4$ is independently —C(O)O—, —C(O)NH—, or —S(O)(O)—; and each instance of $R^5$ is independently an alkyl group, cycloalkyl group, alkenyl group, cycloalkenyl group, aryl group, heteroalkyl group, or heterocyclic group optionally comprising from 2 to 8 tertiary amines or a substituent comprising a tissue-specific or cell-specific targeting moiety.

Examples of acrylates, acrylamides, and vinyl sulfones suitable for use include an acrylate of the formula:

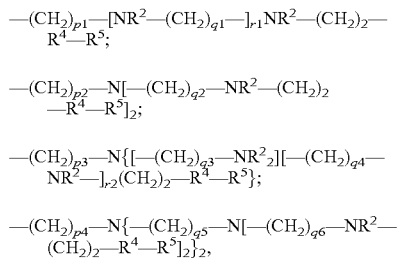

wherein $R^5$ is as described with respect to any of Formulas 1, 1A, 2, 2A, 3, 3A, 3B, 3C, 4, 4.1, 4.2, 4A, 4B, and 4C.

In some embodiments, the Michael addition reaction is facilitated by an acid and/or base. The acid and/or base can be any suitable acid and/or base with any suitable pKa. The acid and/or base can be an organic acid (e.g., p-toluenesulfonic acid), organic base (e.g., triethylamine), inorganic acid (e.g., titanium tetrachloride), inorganic base (e.g., potassium carbonate), or a combination thereof.

In some embodiments, the Michael addition reaction is facilitated by an acid. The acid can be a Brønsted acid or a Lewis acid. In embodiments where the acid is a Brønsted acid, the acid can be a weak acid (i.e., a pKa of from about 4 to about 7) or a strong acid (i.e., a pKa of from about −2 to about 4). Typically, the acid is a weak acid. In certain embodiments, the acid is a Lewis acid. For example, the acid can be bis(trifluoromethanesulfon)imide or p-toluenesulfonic acid.

In some embodiments, the Michael addition reaction is facilitated by a base. The base can be a weak base (i.e., a pKa of from about 7 to about 12) or a strong base (i.e., a pKa of from about 12 to about 50). Typically, the base is a weak base. For example, the base can be triethylamine, diisopropylethylamine, pyridine, N-methyl morpholine, or N,N-dimethyl-piperazine, or derivatives thereof.

In some embodiments, the Michael addition reaction is performed in a solvent. The solvent can be any suitable solvent, or mixture of solvents, capable of solubilizing the polymer and the α,β-unsaturated carbonyl compound to be reacted. For example, the solvent can include water, protic organic solvents, and/or aprotic organic solvents. An exemplary list of solvents includes water, dichloromethane, diethyl ether, dimethyl sulfoxide, acetonitrile, methanol, and ethanol.

In one embodiment, groups $A^1$ and/or $A^2$ (or group $A^3$ of the polymer of Formula 2.1, 4.1, or 4.2) of the polymer are modified by an epoxide opening reaction between the polymer and an epoxide compound. As used herein, the term "epoxide opening" refers to a nucleophilic addition of a nucleophile of the polymer (e.g., a carbanion, an oxygen anion, a nitrogen anion, an oxygen atom, a nitrogen atom, or a combination thereof) to an epoxide compound, thereby opening the epoxide. Accordingly, the epoxide opening reaction is between the polymer and an epoxide compound. In some embodiments, the nucleophile of the polymer is a nitrogen anion, a nitrogen atom, or a combination thereof.

In embodiments where the groups designated $A^1$ and/or $A^2$ (or group $A^3$ of the polymer of Formula 2.1, 4.1, or 4.2) are modified by an epoxide opening reaction, they produce groups designated $B^1$ and/or $B^2$ (or group $A^3$ of the polymer of Formula 4.1 or 4.2) of the formula:

—(CH$_2$)$_{p1}$—[NR$^2$—(CH$_2$)$_{q1}$—]$_{r1}$NR$^2$—CH$_2$—
CHOH—R$^5$;

—(CH$_2$)$_{p2}$—N[—(CH$_2$)$_{q2}$—NR$^2$—CH$_2$—CHOH—
R$^5$]$_2$;

—(CH$_2$)$_{p3}$—N{[—(CH$_2$)$_{q3}$—NR$^2$]$_2$][—(CH$_2$)$_{q4}$—
NR$^2$—]$_{r2}$—CH$_2$—CHOH—R$^5$;

—(CH$_2$)$_{p4}$—N{—(CH$_2$)$_{q5}$—N[—(CH$_2$)$_{q6}$—NR$^2$—
CH$_2$—CHOH—R$^5$]$_2$}$_2$, wherein p1 to p4, q1 to q6, and r1 and r2 are each independently an integer of 1 to 5; each instance of $R^2$ is independently hydrogen or a $C_1$-$C_{12}$ alkyl group, alkenyl group, cycloalkyl group, or cycloalkenyl group; and each instance of $R^5$ is independently an alkyl group, cycloalkyl group, alkenyl group, cycloalkenyl group, aryl group, heteroalkyl group, or heterocyclic group optionally comprising from 2 to 8 tertiary amines or a substituent comprising a tissue-specific or cell-specific targeting moiety.

Examples of epoxides suitable for use include epoxides of the formula:

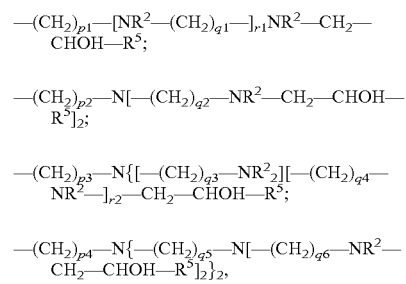

wherein $R^5$ is as described with respect to any of Formulas 1, 1A, 2, 2A, 3, 3A, 3B, 3C, 4, 4.1, 4.2, 4A, 4B, and 4C.

In some embodiments, the epoxide opening reaction is facilitated by an acid and/or base. The acid and/or base can be any suitable acid and/or base with any suitable pKa. The acid and/or base can be an organic acid (e.g., p-toluenesulfonic acid), organic base (e.g., triethylamine), inorganic acid (e.g., titanium tetrachloride), inorganic base (e.g., potassium carbonate), or a combination thereof.

In some embodiments, the epoxide opening reaction is facilitated by an acid. The acid can be a Brønsted acid or a Lewis acid. In embodiments where the acid is a Brønsted acid, the acid can be a weak acid (i.e., a pKa of from about 4 to about 7) or a strong acid (i.e., a pKa of from about −2 to about 4). Typically, the acid is a weak acid. In certain embodiments, the acid is a Lewis acid. For example, the acid can be bis(trifluoromethanesulfon)imide or p-toluenesulfonic acid.

In some embodiments, the epoxide opening reaction is facilitated by a base. The base can be a weak base (i.e., a pKa of from about 7 to about 12) or a strong base (i.e., a pKa of from about 12 to about 50). Typically, the base is a weak base. For example, the base can be triethylamine, diisopropylethylamine, pyridine, N-methyl morpholine, or N,N-dimethyl-piperazine, or derivatives thereof.

In some embodiments, the epoxide opening reaction is performed in a solvent. The solvent can be any suitable solvent, or mixture of solvents, capable of solubilizing the polymer and the epoxide compound to be reacted. For example, the solvent can include water, protic organic solvents, and/or aprotic organic solvents. An exemplary list of solvents includes water, dichloromethane, diethyl ether, dimethyl sulfoxide, acetonitrile, methanol, and ethanol.

In one embodiment, groups $A^1$ and/or $A^2$ (or group $A^3$ of the polymer of Formula 2.1, 4.1, or 4.2) of the polymer are modified by a displacement reaction between the polymer and a compound comprising a leaving group (e.g., chloride atom, bromide atom, iodide atom, tosylate, triflate, mesylate, etc.). As used herein, the term "displacement" refers to a nucleophilic addition of a nucleophile of the polymer (e.g., a carbanion, an oxygen anion, a nitrogen anion, an oxygen atom, a nitrogen atom, or a combination thereof) to a compound comprising a leaving group. Accordingly, the displacement reaction is between the polymer and a compound comprising a leaving group. In some embodiments, the nucleophile of the polymer is a nitrogen anion, a nitrogen atom, or a combination thereof.

In embodiments where the groups designated $A^1$ and/or $A^2$ (or group $A^3$ of the polymer of Formula 2.1, 4.1, or 4.2) are modified by a displacement reaction, they produce groups designated $B^1$ and/or $B^2$ (or group $A^3$ of the polymer of Formula 4.1 or 4.2) of the formula:

—(CH$_2$)$_{p1}$—[NR$^2$—(CH$_2$)$_{q1}$—]$_{r1}$NR$^2$—(CH$_2$)$_2$—R$^5$;

—(CH$_2$)$_{p2}$—N[—(CH$_2$)$_{q2}$—NR$^2$—(CH$_2$)$_2$—R$^5$]$_2$;

—(CH$_2$)$_{p3}$—N{[—(CH$_2$)$_{q3}$—NR$^2$$_2$][—(CH$_2$)$_{q4}$—NR$^2$—]$_{r2}$(CH$_2$)$_2$—R$^5$}; or

—(CH$_2$)$_{p4}$—N{—(CH$_2$)$_{q5}$—N[—(CH$_2$)$_{q6}$—NR$^2$—(CH$_2$)$_2$—R$^5$]$_2$}$_2$, wherein p1 to p4, q1 to q6, and r1 and r2 are each independently an integer of 1 to 5; each instance of $R^2$ is independently hydrogen or a $C_1$-$C_{12}$ alkyl group, alkenyl group, cycloalkyl group, or cycloalkenyl group; and each instance of $R^5$ is independently an alkyl group, cycloalkyl group, alkenyl group, cycloalkenyl group, aryl group, heteroalkyl group, or heterocyclic group optionally comprising from 2 to 8 tertiary amines or a substituent comprising a tissue-specific or cell-specific targeting moiety.

Examples of compounds containing a leaving group suitable for use include compound of formula:

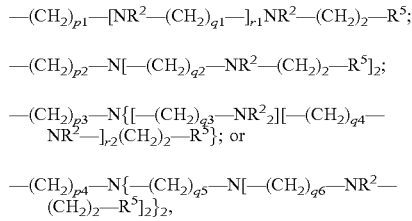

wherein LG is a leaving group (e.g., chloride atom, bromide atom, iodide atom, tosylate, triflate, mesylate, etc.) and $R^5$ is as described with respect to any of Formulas 1, 1A, 2, 2A, 3, 3A, 3B, 3C, 4, 4.1, 4.2, 4A, 4B, and 4C.

In some embodiments, the displacement reaction is facilitated by an acid and/or base. The acid and/or base can be any suitable acid and/or base with any suitable pKa. The acid and/or base can be an organic acid (e.g., p-toluenesulfonic acid), organic base (e.g., triethylamine), inorganic acid (e.g., titanium tetrachloride), inorganic base (e.g., potassium carbonate), or a combination thereof.

In some embodiments, the displacement reaction is facilitated by an acid. The acid can be a Brønsted acid or a Lewis acid. In embodiments where the acid is a Brønsted acid, the acid can be a weak acid (i.e., a pKa of from about 4 to about 7) or a strong acid (i.e., a pKa of from about −2 to about 4). Typically, the acid is a weak acid. In certain embodiments, the acid is a Lewis acid. For example, the acid can be bis(trifluoromethanesulfon)imide or p-toluenesulfonic acid.

In some embodiments, the displacement reaction is facilitated by a base. The base can be a weak base (i.e., a pKa of from about 7 to about 12) or a strong base (i.e., a pKa of from about 12 to about 50). Typically, the base is a weak base. For example, the base can be triethylamine, diisopropylethylamine, pyridine, N-methyl morpholine, or N,N-dimethyl-piperazine, or derivatives thereof.

In some embodiments, the displacement reaction is performed in a solvent. The solvent can be any suitable solvent, or mixture of solvents, capable of solubilizing the polymer and the compound comprising a leaving group to be reacted. For example, the solvent can include water, protic organic solvents, and/or aprotic organic solvents. An exemplary list of solvents includes water, dichloromethane, diethyl ether, dimethyl sulfoxide, acetonitrile, methanol, and ethanol.

In some embodiments, the method further comprises isolating the polymer, or polymer comprising the structure of Formula 1, 1A, 2, 2A, 3, 3A, 3B, 3C, 4, 4.1, 4.2, 4A, 4B, or 4C. The polymer, or polymer comprising the structure of Formula 1, 1A, 2, 2A, 3, 3A, 3B, 3C, 4, 4.1, 4.2, 4A, 4B, or 4C can be isolated by any suitable means. For example, the polymer, or polymer comprising the structure of Formula 1, 1A, 2, 2A, 3, 3A, 3B, 3C, 4, 4.1, 4.2, 4A, 4B, or 4C can be isolated by extraction, crystallization, recrystallization, column chromatography, filtration, or any combination thereof.

Compositions

The polymers provided herein can be used for any purpose. However, it is believed the polymers are particularly useful for delivering nucleic acids and/or polypeptides (e.g., proteins) to cells. Thus, provided herein is a composition comprising a polymer as described herein and a nucleic acid and/or polypeptide (e.g., proteins).

In some embodiments, the composition comprises a nucleic acid. Any nucleic acid can be used. An exemplary list of nucleic acids includes guide and/or donor nucleic acids of CRISPR systems, siRNA, microRNA, interfering RNA or RNAi, dsRNA, mRNA, DNA vector, ribozymes, antisense polynucleotides, and DNA expression cassettes encoding siRNA, microRNA, dsRNA, ribozymes or antisense nucleic acids. SiRNA comprises a double stranded structure typically containing 15-50 base pairs and preferably 19-25 base pairs and having a nucleotide sequence identical or nearly identical to an expressed target gene or RNA within the cell. An siRNA may be composed of two annealed polynucleotides or a single polynucleotide that forms a hairpin structure. MicroRNAs (miRNAs) are small noncoding polynucleotides, about 22 nucleotides long, that direct destruction or translational repression of their mRNA targets. Antisense polynucleotides comprise sequence that is complimentary to a gene or mRNA. Antisense polynucleotides include, but are not limited to: morpholinos, 2'-O-methyl polynucleotides, DNA, RNA and the like. The polynucleotide-based expression inhibitor may be polymerized in vitro, recombinant, contain chimeric sequences, or derivatives of these groups. The polynucleotide-based expression inhibitor may contain ribonucleotides, deoxyribonucleotides, synthetic nucleotides, or any suitable combination such that the target RNA and/or gene is inhibited.

The composition also can comprise any protein for delivery, in addition to or instead of a nucleic acid. The polypeptide can be any suitable polypeptide. For example, the polypeptide can be a zinc finger nuclease, a transcription activator-like effector nuclease ("TALEN"), a recombinase, a deaminase, an endonuclease, or a combination thereof. In some embodiments, the polypeptide is an RNA-guided endonuclease (e.g., a Cas9 polypeptide, a Cpf1 polypeptide, or variants thereof) or a DNA recombinase (e.g., a Cre polypeptide).

It is believed the polymers provided herein are particularly useful for delivering one or more components of a CRISPR system. Thus, in some embodiments, the composition comprises a guide RNA, an RNA-guided endonuclease or nucleic acid encoding same, and/or a donor nucleic acid. The composition can comprise one, two, or all three components together with the polymer described herein. Furthermore, the composition can comprise a plurality of guide RNAs, RNA-guided endonucleases or nucleic acids encoding same, and/or donor nucleic acids. For instance, multiple different guide RNAs for different target sites could be included, optionally with multiple different donor nucleic acids and even multiple different RNA guided endonucleases or nucleic acids encoding same.

Furthermore, the components of the CRISPR system can be combined with one another (when multiple components are present) and the polymer in any particular manner or order. In some embodiments, the guide RNA is complexed with an RNA endonuclease prior to combining with the polymer. In addition, or instead, the guide RNA can be linked (covalently or non-covalently) to a donor nucleic acid prior to combining with the polymer.

The compositions are not limited with respect to any particular CRISPR system (i.e., any particular guide RNA, RNA-guided endonuclease, or donor nucleic acid), many of which are known. Nevertheless, for the sake of further illustration, the components of some such systems are described below.

Donor Nucleic Acid

The donor nucleic acid (or "donor sequence" or "donor polynucleotide" or "donor DNA") is a nucleic acid sequence to be inserted at the cleavage site induced by an RNA-directed endonuclease (e.g., a Cas9 polypeptide or a Cpf1 polypeptide). The donor polynucleotide will contain sufficient homology to a target genomic sequence at the cleavage site, e.g. 70%, 80%, 85%, 90%, 95%, or 100% homology with the nucleotide sequences flanking the cleavage site, e.g. within about 50 bases or less of the cleavage site, e.g. within about 30 bases, within about 15 bases, within about 10 bases, within about 5 bases, or immediately flanking the cleavage site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) will support homology-directed repair. Donor sequences can be of any length, e.g. 10 nucleotides or more, 50 nucleotides or more, 100 nucleotides or more, 250 nucleotides or more, 500 nucleotides or more, 1000 nucleotides or more, 5000 nucleotides or more, etc.

The donor sequence is typically not identical to the genomic sequence that it replaces. Rather, the donor sequence may contain one or more single base changes, insertions, deletions, inversions or rearrangements with respect to the genomic sequence, so long as sufficient homology is present to support homology-directed repair. In some embodiments, the donor sequence comprises a non-homologous sequence flanked by two regions of homology, such that homology-directed repair between the target DNA region and the two flanking sequences results in insertion of the non-homologous sequence at the target region. Donor sequences may also comprise a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor sequence may comprise certain sequence differences as compared to the genomic sequence, e.g. restriction sites, nucleotide polymorphisms, selectable markers (e.g., drug resistance genes, fluorescent proteins, enzymes etc.), etc., which may be used to assess for successful insertion of the donor sequence at the cleavage site or in some embodiments may be used for other purposes (e.g., to signify expression at the targeted genomic locus). In some embodiments, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence.

The donor sequence may be provided to the cell as single-stranded DNA, single-stranded RNA, double-stranded DNA, or double-stranded RNA. It may be introduced into a cell in linear or circular form. If introduced in linear form, the ends of the donor sequence may be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) Proc. Natl. Acad Sci USA 84:4959-4963; Nehls et al. (1996) Science 272:886-889. Amplification procedures such as rolling circle amplification can also be advantageously employed, as exemplified herein. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

As an alternative to protecting the termini of a linear donor sequence, additional lengths of sequence may be included outside of the regions of homology that can be degraded without impacting recombination. A donor sequence can be introduced into a cell as part of a vector molecule having additional sequences such as, for example, replication origins, promoters and genes encoding antibiotic resistance. Moreover, donor sequences can be introduced as naked nucleic acid, as nucleic acid complexed with an agent such as a liposome or polymer, or can be delivered by viruses (e.g., adenovirus, AAV), as described herein for nucleic acids encoding a Cas9 guide RNA and/or a Cas9 fusion polypeptide and/or donor polynucleotide.

Guide Nucleic Acid

In some embodiments, the composition comprises guide nucleic acid. Guide nucleic acids suitable for inclusion in a composition of the present disclosure include single-molecule guide RNAs ("single-guide RNA"/"sgRNA") and dual-molecule guide nucleic acids ("dual-guide RNA"/ "dgRNA").

A guide nucleic acid (e.g., guide RNA) suitable for inclusion in a complex of the present disclosure directs the activities of an RNA-guided endonuclease (e.g., a Cas9 or Cpf1 polypeptide) to a specific target sequence within a target nucleic acid. A guide nucleic acid (e.g., guide RNA) comprises: a first segment (also referred to herein as a "nucleic acid targeting segment", or simply a "targeting segment"); and a second segment (also referred to herein as a "protein-binding segment"). The terms "first" and "second" do not imply the order in which the segments occur in the guide RNA. The order of the elements relative to one another depends upon the particular RNA-guided polypeptide to be used. For instance, guide RNA for Cas9 typically has the protein-binding segment located 3' of the targeting segment, whereas guide RNA for Cpf1 typically has the protein-binding segment located 5' of the targeting segment.

The guide RNA may be introduced into a cell in linear or circular form. If introduced in linear form, the ends of the guide RNA may be protected (e.g., from exonucleolytic degradation) by methods known to those of skill in the art. Amplification procedures such as rolling circle amplification can also be advantageously employed, as exemplified herein.

First Segment: Targeting Segment

The first segment of a guide nucleic acid (e.g., guide RNA) includes a nucleotide sequence that is complementary to a sequence (a target site) in a target nucleic acid. In other words, the targeting segment of a guide nucleic acid (e.g., guide RNA) can interact with a target nucleic acid (e.g., an RNA, a DNA, a double-stranded DNA) in a sequence-specific manner via hybridization (i.e., base pairing). As such, the nucleotide sequence of the targeting segment may vary and can determine the location within the target nucleic acid that the guide nucleic acid (e.g., guide RNA) and the target nucleic acid will interact. The targeting segment of a guide nucleic acid (e.g., guide RNA) can be modified (e.g., by genetic engineering) to hybridize to any desired sequence (target site) within a target nucleic acid.

The targeting segment can have a length of from 12 nucleotides to 100 nucleotides. The nucleotide sequence (the targeting sequence, also referred to as a guide sequence) of the targeting segment that is complementary to a nucleotide sequence (target site) of the target nucleic acid can have a length of 12 nt or more. For example, the targeting sequence of the targeting segment that is complementary to a target site of the target nucleic acid can have a length of 12 nt or more, 15 nt or more, 17 nt or more, 18 nt or more, 19 nt or more, 20 nt or more, 25 nt or more, 30 nt or more, 35 nt or more or 40 nt.

The percent complementarity between the targeting sequence (i.e., guide sequence) of the targeting segment and the target site of the target nucleic acid can be 60% or more (e.g., 65% or more, 70% or more, 75% or more, 80% or more, 85% or more, 90% or more, 95% or more, 97% or more, 98% or more, 99% or more, or 100%). In some embodiments, the percent complementarity between the targeting sequence of the targeting segment and the target site of the target nucleic acid is 100% over the seven contiguous 5'-most nucleotides of the target site of the target nucleic acid. In some embodiments, the percent complementarity between the targeting sequence of the targeting segment and the target site of the target nucleic acid is 60% or more over 20 contiguous nucleotides. In some embodiments, the percent complementarity between the targeting sequence of the targeting segment and the target site of the target nucleic acid is 100% over the seventeen, eighteen, nineteen or twenty contiguous 5'-most nucleotides of the target site of the target nucleic acid and as low as 0% or more over the remainder. In such a case, the targeting sequence can be considered to be 17, 18, 19 or 20 nucleotides in length, respectively.

Second Segment: Protein-Binding Segment

The protein-binding segment of a guide nucleic acid (e.g., guide RNA) interacts with (binds) an RNA-guided endonuclease. The guide nucleic acid (e.g., guide RNA) guides the bound endonuclease to a specific nucleotide sequence within target nucleic acid (the target site) via the above mentioned targeting segment/targeting sequence/guide sequence. The protein-binding segment of a guide nucleic acid (e.g., guide RNA) comprises two stretches of nucleotides that are complementary to one another. The complementary nucleotides of the protein-binding segment hybridize to form a double stranded RNA duplex (dsRNA).

Single and Dual Guide Nucleic Acids

A dual guide nucleic acid (e.g., guide RNA) comprises two separate nucleic acid molecules. Each of the two molecules of a subject dual guide nucleic acid (e.g., guide RNA) comprises a stretch of nucleotides that are complementary to one another such that the complementary nucleotides of the two molecules hybridize to form the double stranded RNA duplex of the protein-binding segment.

In some embodiments, the duplex-forming segment of the activator is 60%, 65%, 70%, 75%, 80%, 85%, 90%, 95%, 98%, 99% or more identical or 100% identical to one of the activator (tracrRNA) molecules set forth in International Patent Application Nos. PCT/US2016/052690 and PCT/US2017/062617, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

In some embodiments, the duplex-forming segment of the targeter is 60%, 65%, 70%, 75%, 80%, 85%, 90%, 95%, 98%, 99% or more identical or 100% identical to one of the targeter (crRNA) sequences set forth in International Patent Application Nos. PCT/US2016/052690 and PCT/US2017/062617, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

A dual guide nucleic acid (e.g., guide RNA) can be designed to allow for controlled (i.e., conditional) binding of a targeter with an activator. Because a dual guide nucleic acid (e.g., guide RNA) is not functional unless both the activator and the targeter are bound in a functional complex with Cas9, a dual guide nucleic acid (e.g., guide RNA) can be inducible (e.g., drug inducible) by rendering the binding between the activator and the targeter to be inducible. As one non-limiting example, RNA aptamers can be used to regulate (i.e., control) the binding of the activator with the targeter. Accordingly, the activator and/or the targeter can include an RNA aptamer sequence.

Aptamers (e.g., RNA aptamers) are known in the art and are generally a synthetic version of a riboswitch. The terms "RNA aptamer" and "riboswitch" are used interchangeably herein to encompass both synthetic and natural nucleic acid sequences that provide for inducible regulation of the structure (and therefore the availability of specific sequences) of the nucleic acid molecule (e.g., RNA, DNA/RNA hybrid, etc.) of which they are part. RNA aptamers usually comprise a sequence that folds into a particular structure (e.g., a hairpin), which specifically binds a particular drug (e.g., a small molecule). Binding of the drug causes a structural change in the folding of the RNA, which changes a feature of the nucleic acid of which the aptamer is a part. As non-limiting examples: (i) an activator with an aptamer may not be able to bind to the cognate targeter unless the aptamer is bound by the appropriate drug; (ii) a targeter with an aptamer may not be able to bind to the cognate activator unless the aptamer is bound by the appropriate drug; and (iii) a targeter and an activator, each comprising a different aptamer that binds a different drug, may not be able to bind to each other unless both drugs are present. As illustrated by these examples, a dual guide nucleic acid (e.g., guide RNA) can be designed to be inducible.

Examples of aptamers and riboswitches can be found, for example, in: Nakamura et al., Genes Cells. 2012 May; 17(5):344-64; Vavalle et al., Future Cardiol. 2012 May; 8(3):371-82; Citartan et al., Biosens Bioelectron. 2012 Apr. 15; 34(1):1-11; and Liberman et al., Wiley Interdiscip Rev RNA. 2012 May-June; 3(3):369-84; all of which are herein incorporated by reference in their entirety.

Non-limiting examples of nucleotide sequences that can be included in a dual guide nucleic acid (e.g., guide RNA) included in International Patent Application Nos. PCT/US2016/052690 and PCT/US2017/062617, or complements thereof that can hybridize to form a protein binding segment.

A subject single guide nucleic acid (e.g., guide RNA) comprises two stretches of nucleotides (much like a "targeter" and an "activator" of a dual guide nucleic acid) that are complementary to one another, hybridize to form the double stranded RNA duplex (dsRNA duplex) of the protein-binding segment (thus resulting in a stem-loop structure), and are covalently linked by intervening nucleotides ("linkers" or "linker nucleotides"). Thus, a subject single guide nucleic acid (e.g., a single guide RNA) can comprise a targeter and an activator, each having a duplex-forming segment, where the duplex-forming segments of the targeter and the activator hybridize with one another to form a dsRNA duplex. The targeter and the activator can be covalently linked via the 3' end of the targeter and the 5' end of the activator. Alternatively, targeter and the activator can be covalently linked via the 5' end of the targeter and the 3' end of the activator.

The linker of a single guide nucleic acid can have a length of from 3 nucleotides to 100 nucleotides. In some embodiments, the linker of a single guide nucleic acid (e.g., guide RNA) is 4 nt.

An exemplary single guide nucleic acid (e.g., guide RNA) comprises two complementary stretches of nucleotides that hybridize to form a dsRNA duplex. In some embodiments, one of the two complementary stretches of nucleotides of the single guide nucleic acid (e.g., guide RNA) (or the DNA encoding the stretch) is 60%, 65%, 70%, 75%, 80%, 85%, 90%, 95%, 98%, 99% or more identical or 100% identical to one of the activator (tracrRNA) molecules set forth in International Patent Application Nos. PCT/US2016/052690 and PCT/US2017/062617, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

In some embodiments, one of the two complementary stretches of nucleotides of the single guide nucleic acid (e.g., guide RNA) (or the DNA encoding the stretch) is 60%, 65%, 70%, 75%, 80%, 85%, 90%, 95%, 98%, 99% or more identical or 100% identical to one of the targeter (crRNA) sequences set forth in International Patent Application Nos. PCT/US2016/052690 and PCT/US2017/062617, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

In some embodiments, one of the two complementary stretches of nucleotides of the single guide nucleic acid (e.g., guide RNA) (or the DNA encoding the stretch) is 60%, 65%, 70%, 75%, 80%, 85%, 90%, 95%, 98%, 99% or more identical or 100% identical to one of the targeter (crRNA) sequences or activator (tracrRNA) sequences set forth in International Patent Application Nos. PCT/US2016/052690 and PCT/US2017/062617, or a complement thereof, over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides).

Appropriate cognate pairs of targeters and activators can be routinely determined by taking into account the species name and base-pairing (for the dsRNA duplex of the protein-binding domain) Any activator/targeter pair can be used as part of dual guide nucleic acid (e.g., guide RNA) or as part of a single guide nucleic acid (e.g., guide RNA).

In some embodiments, an activator (e.g., a trRNA, trRNA-like molecule, etc.) of a dual guide nucleic acid (e.g., guide RNA) (e.g., a dual guide RNA) or a single guide nucleic acid (e.g., guide RNA) (e.g., a single guide RNA) includes a stretch of nucleotides with 60%, 65%, 70%, 75%, 80%, 85%, 90%, 95%, 98%, 99% or more, or 100% sequence identity with an activator (tracrRNA) molecule set forth in International Patent Application Nos. PCT/US2016/052690 and PCT/US2017/062617, or a complement thereof.

In some embodiments, an activator (e.g., a trRNA, trRNA-like molecule, etc.) of a dual guide nucleic acid (e.g., a dual guide RNA) or a single guide nucleic acid (e.g., a single guide RNA) includes 30 or more nucleotides (nt) (e.g., 40 or more, 50 or more, 60 or more, 70 or more, 75 or more nt). In some embodiments, an activator (e.g., a trRNA, trRNA-like molecule, etc.) of a dual guide nucleic acid (e.g., a dual guide RNA) or a single guide nucleic acid (e.g., a single guide RNA) has a length in a range of from 30 to 200 nucleotides (nt).

The protein-binding segment can have a length of from 10 nucleotides to 100 nucleotides.

Also with regard to both a subject single guide nucleic acid (e.g., single guide RNA) and to a subject dual guide nucleic acid (e.g., dual guide RNA), the dsRNA duplex of the protein-binding segment can have a length from 6 base pairs (bp) to 50 bp. The percent complementarity between the nucleotide sequences that hybridize to form the dsRNA duplex of the protein-binding segment can be 60% or more. For example, the percent complementarity between the nucleotide sequences that hybridize to form the dsRNA duplex of the protein-binding segment can be 65% or more, 70% or more, 75% or more, 80% or more, 85% or more, 90% or more, 95% or more, 98% or more, or 99% or more (e.g., in some embodiments, there are some nucleotides that do not hybridize and therefore create a bulge within the dsRNA duplex. In some embodiments, the percent complementarity between the nucleotide sequences that hybridize to form the dsRNA duplex of the protein-binding segment is 100%.

Hybrid Guide Nucleic Acids

In some embodiments, a guide nucleic acid is two RNA molecules (dual guide RNA). In some embodiments, a guide nucleic acid is one RNA molecule (single guide RNA). In some embodiments, a guide nucleic acid is a DNA/RNA hybrid molecule. In such embodiments, the protein-binding segment of the guide nucleic acid is RNA and forms an RNA duplex. Thus, the duplex-forming segments of the activator and the targeter is RNA. However, the targeting segment of a guide nucleic acid can be DNA. Thus, if a DNA/RNA hybrid guide nucleic acid is a dual guide nucleic acid, the "targeter" molecule and be a hybrid molecule (e.g., the targeting segment can be DNA and the duplex-forming segment can be RNA). In such embodiments, the duplex-forming segment of the "activator" molecule can be RNA (e.g., in order to form an RNA-duplex with the duplex-forming segment of the targeter molecule), while nucleotides of the "activator" molecule that are outside of the duplex-forming segment can be DNA (in which case the activator molecule is a hybrid DNA/RNA molecule) or can be RNA (in which case the activator molecule is RNA). If a DNA/RNA hybrid guide nucleic acid is a single guide nucleic acid, then the targeting segment can be DNA, the duplex-forming segments (which make up the protein-binding segment of the single guide nucleic acid) can be RNA, and nucleotides outside of the targeting and duplex-forming segments can be RNA or DNA.

A DNA/RNA hybrid guide nucleic can be useful in some embodiments, for example, when a target nucleic acid is an RNA. Cas9 normally associates with a guide RNA that hybridizes with a target DNA, thus forming a DNA-RNA duplex at the target site. Therefore, when the target nucleic acid is an RNA, it is sometimes advantageous to recapitulate a DNA-RNA duplex at the target site by using a targeting segment (of the guide nucleic acid) that is DNA instead of RNA. However, because the protein-binding segment of a guide nucleic acid is an RNA-duplex, the targeter molecule is DNA in the targeting segment and RNA in the duplex-forming segment. Hybrid guide nucleic acids can bias Cas9 binding to single stranded target nucleic acids relative to double stranded target nucleic acids.

Exemplary Guide Nucleic Acids

Any guide nucleic acid can be used. Many different types of guide nucleic acids are known in the art. The guide nucleic selected will be appropriately paired to the particular CRISPR system being used (e.g., the particular RNA guided endonuclease being used). Thus, the guide nucleic acid can be, for instance, a guide nucleic acid corresponding to any RNA guided endonuclease described herein or known in the art. Guide nucleic acids and RNA guided endonucleases are described, for example, in International Patent Application Nos. PCT/US2016/052690 and PCT/US2017/062617

In some embodiments, a suitable guide nucleic acid includes two separate RNA polynucleotide molecules. In some embodiments, the first of the two separate RNA polynucleotide molecules (the activator) comprises a nucleotide sequence having 60% or more (e.g., 65% or more, 70% or more, 75% or more, 80% or more, 85% or more, 90% or more, 95% or more, 98% or more, 99% or more, or 100%) nucleotide sequence identity over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides) to any one of the nucleotide sequences set forth in International Patent Application Nos. PCT/US2016/052690 and PCT/US2017/062617, or a complement thereof. In some embodiments, the second of the two separate RNA polynucleotide molecules (the targeter) comprises a nucleotide sequence having 60% or more (e.g., 65% or more, 70% or more, 75% or more, 80% or more, 85% or more, 90% or more, 95% or more, 98% or more, 99% or more, or 100%) nucleotide sequence identity over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides) to any one of the nucleotide sequences set forth in International Patent Application Nos. PCT/US2016/052690 and PCT/US2017/062617, or a complement thereof.

In some embodiments, a suitable guide nucleic acid is a single RNA polynucleotide and comprises first and second nucleotide sequence having 60% or more (e.g., 65% or more, 70% or more, 75% or more, 80% or more, 85% or more, 90% or more, 95% or more, 98% or more, 99% or more, or 100%) nucleotide sequence identity over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides) to any one of the nucleotide sequences set forth in International Patent Application Nos. PCT/US2016/052690 and PCT/US2017/062617, or complements thereof.

In some embodiments, the guide RNA is a Cpf1 and/or Cas9 guide RNA. A Cpf1 and/or Cas9 guide RNA can have a total length of from 30 nucleotides (nt) to 100 nt, e.g., from 30 nt to 40 nt, from 40 nt to 45 nt, from 45 nt to 50 nt, from 50 nt to 60 nt, from 60 nt to 70 nt, from 70 nt to 80 nt, from 80 nt to 90 nt, or from 90 nt to 100 nt. In some embodiments, a Cpf1 and/or Cas9 guide RNA has a total length of 35 nt, 36 nt, 37 nt, 38 nt, 39 nt, 40 nt, 41 nt, 42 nt, 43 nt, 44 nt, 45 nt, 46 nt, 47 nt, 48 nt, 49 nt, or 50 nt. A Cpf1 and/or Cas9 guide RNA can include a target nucleic acid-binding segment and a duplex-forming segment.

The target nucleic acid-binding segment of a Cpf1 and/or Cas9 guide RNA can have a length of from 15 nt to 30 nt, e.g., 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, or 30 nt. In some embodiments, the target nucleic acid-binding segment has a length of 23 nt. In some embodiments, the target nucleic acid-binding segment has a length of 24 nt. In some embodiments, the target nucleic acid-binding segment has a length of 25 nt.

The target nucleic acid-binding segment of a Cpf1 and/or Cas9 guide RNA can have 100% complementarity with a corresponding length of target nucleic acid sequence. The targeting segment can have less than 100% complementarity with a corresponding length of target nucleic acid sequence. For example, the target nucleic acid binding segment of a Cpf1 and/or Cas9 guide RNA can have 1, 2, 3, 4, or 5 nucleotides that are not complementary to the target nucleic acid sequence. For example, in some embodiments, where a target nucleic acid-binding segment has a length of 25 nucleotides, and the target nucleic acid sequence has a length of 25 nucleotides, in some embodiments, the target nucleic acid-binding segment has 100% complementarity to the target nucleic acid sequence. As another example, in some embodiments, where a target nucleic acid-binding segment has a length of 25 nucleotides, and the target nucleic acid sequence has a length of 25 nucleotides, in some embodiments, the target nucleic acid-binding segment has 1 non-complementary nucleotide and 24 complementary nucleotides with the target nucleic acid sequence.

The duplex-forming segment of a Cpf1 and/or Cas9 guide RNA can have a length of from 15 nt to 25 nt, e.g., 15 nt, 16 nt, 17 nt, 18 nt, 19 nt, 20 nt, 21 nt, 22 nt, 23 nt, 24 nt, or 25 nt.

In some embodiments, the duplex-forming segment of a Cpf1 guide RNA can comprise the nucleotide sequence 5'-AAUUUCUACUGUUGUAGAU-3'.

Additional Elements

In some embodiments, a guide nucleic acid (e.g., guide RNA) includes an additional segment or segments (in some embodiments at the 5' end, in some embodiments the 3' end, in some embodiments at either the 5' or 3' end, in some embodiments embedded within the sequence (i.e., not at the 5' and/or 3' end), in some embodiments at both the 5' end and the 3' end, in some embodiments embedded and at the 5' end and/or the 3' end, etc.). For example, a suitable additional segment can include a 5' cap (e.g., a 7-methylguanylate cap ($m^7G$)); a 3' polyadenylated tail (i.e., a 3' poly(A) tail); a ribozyme sequence (e.g. to allow for self-cleavage of a guide nucleic acid or component of a guide nucleic acid, e.g., a targeter, an activator, etc.); a riboswitch sequence (e.g., to allow for regulated stability and/or regulated accessibility by proteins and protein complexes); a sequence that forms a dsRNA duplex (i.e., a hairpin)); a sequence that targets an RNA to a subcellular location (e.g., nucleus, mitochondria, chloroplasts, and the like); a modification or sequence that provides for tracking (e.g., a label such as a fluorescent molecule (i.e., fluorescent dye), a sequence or other moiety that facilitates fluorescent detection; a sequence or other modification that provides a binding site for proteins (e.g., proteins that act on DNA, including transcriptional activators, transcriptional repressors, DNA methyltransferases, DNA demethylases, histone acetyltransferases, histone deacetylases, proteins that bind RNA (e.g., RNA aptamers), labeled proteins, fluorescently labeled proteins, and the like); a modification or sequence that provides for increased, decreased, and/or controllable stability; and combinations thereof RNA-Guided Endonuclease In addition to, or instead of, a guide nucleic acid, the composition can comprise an RNA-guided endonuclease protein or nucleic acid (e.g., mRNA or vector) encoding same. Any RNA-guided endonuclease can be used. The selection of the RNA guided endonuclease used will depend, at least in part, to the intended end-use of the CRISPR system employed.

In some embodiments, the polypeptide is a Cas 9 polypeptide. Suitable Cas9 polypeptides for inclusion in a composition of the present disclosure include a naturally-occurring Cas9 polypeptide (e.g., naturally occurs in bacterial and/or archaeal cells), or a non-naturally-occurring Cas9 polypeptide (e.g., the Cas9 polypeptide is a variant Cas9 polypeptide, a chimeric polypeptide as discussed below, and the like), as described below. In some embodiments, one skilled in the art can appreciate that the Cas9 polypeptide disclosed herein can be any variant derived or isolated from any source. In other embodiments, the Cas9 peptide of the present disclosure can include one or more of the mutations described in the literature, including but not limited to the functional mutations described in: Fonfara et al. Nucleic Acids Res. 2014 February; 42(4):2577-90; Nishimasu H. et al. Cell. 2014 Feb. 27; 156(5):935-49; Jinek M. et al. Science. 2012 337:816-21; and Jinek M. et al. Science. 2014 Mar. 14; 343(6176); see also U.S. patent application Ser. No. 13/842,859, filed Mar. 15, 2013, which is hereby incorporated by reference; further, see U.S. Pat. Nos. 8,697,359; 8,771,945; 8,795,965; 8,865,406; 8,871,445; 8,889,356; 8,895,308; 8,906,616; 8,932,814; 8,945,839; 8,993,233; and 8,999,641, which are all hereby incorporated by reference. Thus, in some embodiments, the systems and methods disclosed herein can be used with the wild type Cas9 protein having double-stranded nuclease activity, Cas9 mutants that act as single stranded nickases, or other mutants with modified nuclease activity. As such, a Cas9 polypeptide that is suitable for inclusion in a composition of the present disclosure can be an enzymatically active Cas9 polypeptide, e.g., can make single- or double-stranded breaks in a target nucleic acid, or alternatively can have reduced enzymatic activity compared to a wild-type Cas9 polypeptide.

Naturally occurring Cas9 polypeptides bind a guide nucleic acid, are thereby directed to a specific sequence within a target nucleic acid (a target site), and cleave the target nucleic acid (e.g., cleave dsDNA to generate a double strand break, cleave ssDNA, cleave ssRNA, etc.). A subject Cas9 polypeptide comprises two portions, an RNA-binding portion and an activity portion. The RNA-binding portion interacts with a subject guide nucleic acid, and an activity portion exhibits site-directed enzymatic activity (e.g., nuclease activity, activity for DNA and/or RNA methylation, activity for DNA and/or RNA cleavage, activity for histone acetylation, activity for histone methylation, activity for RNA modification, activity for RNA-binding, activity for RNA splicing etc. In some embodiments the activity portion exhibits reduced nuclease activity relative to the corresponding portion of a wild type Cas9 polypeptide. In some embodiments, the activity portion is enzymatically inactive.

Assays to determine whether a protein has an RNA-binding portion that interacts with a subject guide nucleic acid can be any convenient binding assay that tests for binding between a protein and a nucleic acid. Exemplary binding assays include binding assays (e.g., gel shift assays) that involve adding a guide nucleic acid and a Cas9 polypeptide to a target nucleic acid.

Assays to determine whether a protein has an activity portion (e.g., to determine if the polypeptide has nuclease activity that cleave a target nucleic acid) can be any convenient nucleic acid cleavage assay that tests for nucleic acid cleavage. Exemplary cleavage assays that include adding a guide nucleic acid and a Cas9 polypeptide to a target nucleic acid.

In some embodiments, a suitable Cas9 polypeptide for inclusion in a composition of the present disclosure has enzymatic activity that modifies target nucleic acid (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In other embodiments, a suitable Cas9 polypeptide for inclusion in a composition of the present disclosure has enzymatic activity that modifies a polypeptide (e.g., a histone) associated with target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Many Cas9 orthologues from a wide variety of species have been identified and in some embodiments, the proteins share only a few identical amino acids. All identified Cas9 orthologues have the same domain architecture with a central HNH endonuclease domain and a split RuvC/RNaseH domain. Cas9 proteins share 4 key motifs with a conserved architecture. Motifs 1, 2, and 4 are RuvC like motifs while motif 3 is an HNH-motif.

In some embodiments, a suitable Cas9 polypeptide comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to the Cas9 amino acid sequence depicted in FIG. 1 (SEQ ID NO:1); or alternatively to motifs 1-4 of the Cas9 amino acid sequence depicted in Table 1 below (motifs 1-4 of SEQ ID NO:1 are SEQ ID NOs:3-6, respectively, as depicted in Table 1 below); or alternatively to amino acids 7-166 or 731-1003 of the Cas9 amino acid sequence depicted in FIG. 1 (SEQ ID NO:1)

In some embodiments, a Cas9 polypeptide comprises an amino acid sequence having 75% or more, 80% or more, 85% or more, 90% or more, 95% or more, or 98%, amino acid sequence identity to the amino acid sequence depicted in FIG. 1 and set forth in SEQ ID NO:1; and comprises amino acid substitutions of N497, R661, Q695, and Q926 relative to the amino acid sequence set forth in SEQ ID NO:1; or comprises an amino acid substitution of K855 relative to the amino acid sequence set forth in SEQ ID NO:1; or comprises amino acid substitutions of K810, K1003, and R1060 relative to the amino acid sequence set forth in SEQ ID NO:1; or comprises amino acid substitutions of K848, K1003, and R1060 relative to the amino acid sequence set forth in SEQ ID NO:1.

As used herein, the term "Cas9 polypeptide" encompasses the term "variant Cas9 polypeptide"; and the term "variant Cas9 polypeptide" encompasses the term "chimeric Cas9 polypeptide."

Variant Cas9 Polypeptides

A suitable Cas9 polypeptides for inclusion in a composition of the present disclosure includes a variant Cas9 polypeptide. A variant Cas9 polypeptide has an amino acid sequence that is different by one amino acid (e.g., has a deletion, insertion, substitution, fusion) (i.e., different by at least one amino acid) when compared to the amino acid sequence of a wild type Cas9 polypeptide (e.g., a naturally occurring Cas9 polypeptide, as described above). In some instances, the variant Cas9 polypeptide has an amino acid change (e.g., deletion, insertion, or substitution) that reduces the nuclease activity of the Cas9 polypeptide. For example, in some instances, the variant Cas9 polypeptide has less than 50%, less than 40%, less than 30%, less than 20%, less than 10%, less than 5%, or less than 1% of the nuclease activity of the corresponding wild-type Cas9 polypeptide. In some embodiments, the variant Cas9 polypeptide has no substantial nuclease activity. When a Cas9 polypeptide is a variant Cas9 polypeptide that has no substantial nuclease activity, it can be referred to as "dCas9."

In some embodiments, a variant Cas9 polypeptide has reduced nuclease activity. For example, a variant Cas9 polypeptide suitable for use in a binding method of the present disclosure exhibits less than about 20%, less than about 15%, less than about 10%, less than about 5%, less than about 1%, or less than about 0.1%, of the endonuclease activity of a wild-type Cas9 polypeptide, e.g., a wild-type Cas9 polypeptide comprising an amino acid sequence as depicted in FIG. 1 (SEQ ID NO: 1).

In some embodiments, a variant Cas9 polypeptide can cleave the complementary strand of a target nucleic acid but has reduced ability to cleave the non-complementary strand of a double stranded target nucleic acid. For example, the variant Cas9 polypeptide can have a mutation (amino acid substitution) that reduces the function of the RuvC domain (e.g., "domain 1" of FIG. 1). As a non-limiting example, in some embodiments, a variant Cas9 polypeptide has a D10A mutation (e.g., aspartate to alanine at an amino acid position corresponding to position 10 of SEQ ID NO:1) and can therefore cleave the complementary strand of a double stranded target nucleic acid but has reduced ability to cleave the non-complementary strand of a double stranded target nucleic acid (thus resulting in a single strand break (SSB) instead of a double strand break (DSB) when the variant Cas9 polypeptide cleaves a double stranded target nucleic acid) (see, for example, Jinek et al., Science. 2012 Aug. 17; 337(6096):816-21).

In some embodiments, a variant Cas9 polypeptide can cleave the non-complementary strand of a double stranded target nucleic acid but has reduced ability to cleave the complementary strand of the target nucleic acid. For example, the variant Cas9 polypeptide can have a mutation (amino acid substitution) that reduces the function of the HNH domain (RuvC/HNH/RuvC domain motifs, "domain 2" of FIG. 1). As a non-limiting example, in some embodiments, the variant Cas9 polypeptide can have an H840A mutation (e.g., histidine to alanine at an amino acid position corresponding to position 840 of SEQ ID NO:1) (FIG. 1) and can therefore cleave the non-complementary strand of the target nucleic acid but has reduced ability to cleave the complementary strand of the target nucleic acid (thus resulting in a SSB instead of a DSB when the variant Cas9 polypeptide cleaves a double stranded target nucleic acid). Such a Cas9 polypeptide has a reduced ability to cleave a target nucleic acid (e.g., a single stranded target nucleic acid) but retains the ability to bind a target nucleic acid (e.g., a single-stranded or a double-stranded target nucleic acid).

In some embodiments, a variant Cas9 polypeptide has a reduced ability to cleave both the complementary and the non-complementary strands of a double stranded target nucleic acid. As a non-limiting example, in some embodiments, the variant Cas9 polypeptide harbors both the D10A and the H840A mutations (e.g., mutations in both the RuvC domain and the HNH domain) such that the polypeptide has a reduced ability to cleave both the complementary and the non-complementary strands of a double stranded target nucleic acid. Such a Cas9 polypeptide has a reduced ability to cleave a target nucleic acid (e.g., a single-stranded target nucleic acid or a double-stranded target nucleic acid) but retains the ability to bind a target nucleic acid (e.g., a single stranded target nucleic acid or a double-stranded target nucleic acid).

As another non-limiting example, in some embodiments, the variant Cas9 polypeptide harbors W476A and W1126A mutations such that the polypeptide has a reduced ability to cleave a target nucleic acid. Such a Cas9 polypeptide has a reduced ability to cleave a target nucleic acid but retains the ability to bind a target nucleic acid.

As another non-limiting example, in some embodiments, the variant Cas9 polypeptide harbors P475A, W476A, N477A, D1125A, W1126A, and D1127A mutations such that the polypeptide has a reduced ability to cleave a target nucleic acid. Such a Cas9 polypeptide has a reduced ability to cleave a target nucleic acid but retains the ability to bind a target nucleic acid.

As another non-limiting example, in some embodiments, the variant Cas9 polypeptide harbors H840A, W476A, and W1126A, mutations such that the polypeptide has a reduced ability to cleave a target nucleic acid. Such a Cas9 polypeptide has a reduced ability to cleave a target nucleic acid but retains the ability to bind a target nucleic acid.

As another non-limiting example, in some embodiments, the variant Cas9 polypeptide harbors H840A, D10A, W476A, and W1126A, mutations such that the polypeptide has a reduced ability to cleave a target nucleic acid. Such a Cas9 polypeptide has a reduced ability to cleave a target nucleic acid but retains the ability to bind a target nucleic acid.

As another non-limiting example, in some embodiments, the variant Cas9 polypeptide harbors, H840A, P475A, W476A, N477A, D1125A, W1126A, and D1127A mutations such that the polypeptide has a reduced ability to cleave a target nucleic acid. Such a Cas9 polypeptide has a reduced ability to cleave a target nucleic acid but retains the ability to bind a target nucleic acid.

As another non-limiting example, in some embodiments, the variant Cas9 polypeptide harbors D10A, H840A, P475A, W476A, N477A, D1125A, W1126A, and D1127A mutations such that the polypeptide has a reduced ability to cleave a target nucleic acid. Such a Cas9 polypeptide has a reduced ability to cleave a target nucleic acid but retains the ability to bind a target nucleic acid.

Other residues can be mutated to achieve the above effects (i.e. inactivate one or the other nuclease portions). As non-limiting examples, residues D10, G12, G17, E762, H840, N854, N863, H982, H983, A984, D986, and/or A987 can be altered (i.e., substituted) (see Table 1 for more information regarding the conservation of Cas9 amino acid residues). Also, mutations other than alanine substitutions are suitable.

In some embodiments, a variant Cas9 polypeptide that has reduced catalytic activity (e.g., when a Cas9 protein has a D10, G12, G17, E762, H840, N854, N863, H982, H983, A984, D986, and/or a A987 mutation, e.g., D10A, G12A, G17A, E762A, H840A, N854A, N863A, H982A, H983A, A984A, and/or D986A), the variant Cas9 polypeptide can still bind to target nucleic acid in a site-specific manner (because it is still guided to a target nucleic acid sequence by a guide nucleic acid) as long as it retains the ability to interact with the guide nucleic acid.

TABLE 1

Table 1 lists 4 motifs that are present in Cas9 sequences from various species The amino acids listed here are from the Cas9 from *S. pyogenes* (SEQ ID NO: 1).

| Motif | Motif | Amino acids (residue #s) | Highly conserved |
|---|---|---|---|
| 1 | RuvC | IGLDIGTNSVGWAVI (7-21) (SEQ ID NO: 3) | D10, G12, G17 |
| 2 | RuvC | IVIEMARE (759-766) (SEQ ID NO: 4) | E762 |
| 3 | HNH-motif | DVDHIVPQSFLKDDSIDNKVLTRSDKN (837-863) (SEQ ID NO: 5) | H840, N854, N863 |
| 4 | RuvC | HHAHDAYL (982-989) (SEQ ID NO: 6) | H982, H983, A984, D986, A987 |

In addition to the above, a variant Cas9 protein can have the same parameters for sequence identity as described above for Cas9 polypeptides. Thus, in some embodiments, a suitable variant Cas9 polypeptide comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity of the Cas9 amino acid sequence depicted in FIG. 1 (SEQ ID NO:1), or alternatively to motifs 1-4 (motifs 1-4 of SEQ ID NO:1 are SEQ ID NOs:3-6, respectively, as depicted in Table 1); or alternatively to amino acids 7-166 or 731-1003 of the Cas9 amino acid sequence depicted in FIG. 1 (SEQ ID NO:1. Any Cas9 protein as defined above can be used as a Cas9 polypeptide, or as part of a chimeric Cas9 polypeptide, in a composition of the present disclosure, including those specifically referenced in International Patent Application Nos. PCT/US2016/052690 and PCT/US2017/062617.

In some embodiments, a suitable variant Cas9 polypeptide comprises an amino acid sequence having 60% or more, 70% or more, 75% or more, 80% or more, 85% or more, 90% or more, 95% or more, 99% or more, or 100% amino acid sequence identity to the Cas9 amino acid sequence depicted in FIG. 1 (SEQ ID NO:1). Any Cas9 protein as defined above can be used as a variant Cas9 polypeptide or as part of a chimeric variant Cas9 polypeptide in a composition of the present disclosure, including those specifically referenced in International Patent Application Nos. PCT/US2016/052690 and PCT/US2017/062617.

Chimeric Polypeptides (Fusion Polypeptides)

In some embodiments, a variant Cas9 polypeptide is a chimeric Cas9 polypeptide (also referred to herein as a fusion polypeptide, e.g., a "Cas9 fusion polypeptide"). A Cas9 fusion polypeptide can bind and/or modify a target nucleic acid (e.g., cleave, methylate, demethylate, etc.) and/or a polypeptide associated with target nucleic acid (e.g., methylation, acetylation, etc., of, for example, a histone tail).

A Cas9 fusion polypeptide is a variant Cas9 polypeptide by virtue of differing in sequence from a wild type Cas9 polypeptide (e.g., a naturally occurring Cas9 polypeptide). A Cas9 fusion polypeptide is a Cas9 polypeptide (e.g., a wild type Cas9 polypeptide, a variant Cas9 polypeptide, a variant Cas9 polypeptide with reduced nuclease activity (as described above), and the like) fused to a covalently linked heterologous polypeptide (also referred to as a "fusion partner"). In some embodiments, a Cas9 fusion polypeptide is a variant Cas9 polypeptide with reduced nuclease activity (e.g., dCas9) fused to a covalently linked heterologous polypeptide. In some embodiments, the heterologous polypeptide exhibits (and therefore provides for) an activity (e.g., an enzymatic activity) that will also be exhibited by the Cas9 fusion polypeptide (e.g., methyltransferase activity, acetyltransferase activity, kinase activity, ubiquitinating activity, etc.). In some such embodiments, a method of binding, e.g., where the Cas9 polypeptide is a variant Cas9 polypeptide having a fusion partner (i.e., having a heterologous polypeptide) with an activity (e.g., an enzymatic activity) that modifies the target nucleic acid, the method can also be considered to be a method of modifying the target nucleic acid. In some embodiments, a method of binding a target nucleic acid (e.g., a single stranded target nucleic acid) can result in modification of the target nucleic acid. Thus, in some embodiments, a method of binding a target nucleic acid (e.g., a single stranded target nucleic acid) can be a method of modifying the target nucleic acid.

In some embodiments, the heterologous sequence provides for subcellular localization, i.e., the heterologous sequence is a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an endoplasmic reticulum (ER) retention signal, and the like). In some embodiments, a variant Cas9 does not include a NLS so that the protein is not targeted to the nucleus (which can be advantageous, e.g., when the target nucleic acid is an RNA that is present in the cytosol). In some embodiments, the heterologous sequence can provide a tag (i.e., the heterologous sequence is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like). In some embodiments, the heterologous sequence can provide for increased or decreased stability (i.e., the heterologous sequence is a stability control peptide, e.g., a degron, which in some embodiments is controllable (e.g., a temperature sensitive or drug controllable degron sequence, see below). In some embodiments, the heterologous sequence can provide for increased or decreased transcription from the target nucleic acid (i.e., the heterologous sequence is a transcription modulation sequence, e.g., a transcription factor/activator or a fragment thereof, a protein or fragment thereof that recruits a transcription factor/activator, a transcription repressor or a fragment thereof, a protein or fragment thereof that recruits a transcription repressor, a small molecule/drug-responsive transcription regulator, etc.). In some embodiments, the heterologous sequence can provide a binding domain (i.e., the heterologous sequence is a protein binding sequence, e.g., to provide the ability of a Cas9 fusion polypeptide to bind to another protein of interest, e.g., a DNA or histone modifying protein, a transcription factor or transcription repressor, a recruiting protein, an RNA modification enzyme, an RNA-binding protein, a translation initiation factor, an RNA splicing factor, etc.). A heterologous nucleic acid sequence may be linked to another nucleic acid sequence (e.g., by genetic engineering) to generate a chimeric nucleotide sequence encoding a chimeric polypeptide.

A subject Cas9 fusion polypeptide (Cas9 fusion protein) can have multiple (1 or more, 2 or more, 3 or more, etc.) fusion partners in any combination of the above. As an illustrative example, a Cas9 fusion protein can have a heterologous sequence that provides an activity (e.g., for transcription modulation, target modification, modification of a protein associated with a target nucleic acid, etc.) and can also have a subcellular localization sequence. In some embodiments, such a Cas9 fusion protein might also have a tag for ease of tracking and/or purification (e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like). As another illustrative example, a Cas9 protein can have one or more NLSs (e.g., two or more, three or more, four or more, five or more, 1, 2, 3, 4, or 5 NLSs). In some embodiments a fusion partner (or multiple fusion partners) (e.g., an NLS, a tag, a fusion partner providing an activity, etc.) is located at or near the C-terminus of Cas9. In some embodiments a fusion partner (or multiple fusion partners) (e.g., an NLS, a tag, a fusion partner providing an activity, etc.) is located at the N-terminus of Cas9. In some embodiments a Cas9 has a fusion partner (or multiple fusion partners)(e.g., an NLS, a tag, a fusion partner providing an activity, etc.) at both the N-terminus and C-terminus.

Suitable fusion partners that provide for increased or decreased stability include, but are not limited to degron sequences. Degrons are readily understood by one of ordinary skill in the art to be amino acid sequences that control the stability of the protein of which they are part. For example, the stability of a protein comprising a degron sequence is controlled in part by the degron sequence. In some embodiments, a suitable degron is constitutive such that the degron exerts its influence on protein stability independent of experimental control (i.e., the degron is not drug inducible, temperature inducible, etc.) In some embodiments, the degron provides the variant Cas9 polypeptide with controllable stability such that the variant Cas9 polypeptide can be turned "on" (i.e., stable) or "off" (i.e., unstable, degraded) depending on the desired conditions. For example, if the degron is a temperature sensitive degron, the variant Cas9 polypeptide may be functional (i.e., "on", stable) below a threshold temperature (e.g., 42° C., 41° C., 40° C., 39° C., 38° C., 37° C., 36° C., 35° C., 34° C., 33° C., 32° C., 31° C., 30° C., etc.) but non-functional (i.e., "off", degraded) above the threshold temperature. As another example, if the degron is a drug inducible degron, the presence or absence of drug can switch the protein from an "off" (i.e., unstable) state to an "on" (i.e., stable) state or vice versa. An exemplary drug inducible degron is derived from the FKBP12 protein. The stability of the degron is controlled by the presence or absence of a small molecule that binds to the degron.

Examples of suitable degrons include, but are not limited to those degrons controlled by Shield-1, DHFR, auxins, and/or temperature. Non-limiting examples of suitable degrons are known in the art (e.g., Dohmen et al., Science, 1994. 263(5151): p. 1273-1276: Heat-inducible degron: a method for constructing temperature-sensitive mutants; Schoeber et al., Am J Physiol Renal Physiol. 2009 January;

296(1):F204-11: Conditional fast expression and function of multimeric TRPV5 channels using Shield-1; Chu et al., Bioorg Med Chem Lett. 2008 Nov. 15; 18(22):5941-4: Recent progress with FKBP-derived destabilizing domains; Kanemaki, Pflugers Arch. 2012 Dec. 28: Frontiers of protein expression control with conditional degrons; Yang et al., Mol Cell. 2012 Nov. 30; 48(4):487-8: Titivated for destruction: the methyl degron; Barbour et al., Biosci Rep. 2013 Jan. 18; 33(1): Characterization of the bipartite degron that regulates ubiquitin-independent degradation of thymidylate synthase; and Greussing et al., J Vis Exp. 2012 Nov. 10; (69): Monitoring of ubiquitin-proteasome activity in living cells using a Degron (dgn)-destabilized green fluorescent protein (GFP)-based reporter protein; all of which are hereby incorporated in their entirety by reference).

Exemplary degron sequences have been well-characterized and tested in both cells and animals. Thus, fusing Cas9 (e.g., wild type Cas9; variant Cas9; variant Cas9 with reduced nuclease activity, e.g., dCas9; and the like) to a degron sequence produces a "tunable" and "inducible" Cas9 polypeptide. Any of the fusion partners described herein can be used in any desirable combination. As one non-limiting example to illustrate this point, a Cas9 fusion protein (i.e., a chimeric Cas9 polypeptide) can comprise a YFP sequence for detection, a degron sequence for stability, and transcription activator sequence to increase transcription of the target nucleic acid. A suitable reporter protein for use as a fusion partner for a Cas9 polypeptide (e.g., wild type Cas9, variant Cas9, variant Cas9 with reduced nuclease function, etc.), includes, but is not limited to, the following exemplary proteins (or functional fragment thereof): his3, β-galactosidase, a fluorescent protein (e.g., GFP, RFP, YFP, cherry, tomato, etc., and various derivatives thereof), luciferase, β-glucuronidase, and alkaline phosphatase. Furthermore, the number of fusion partners that can be used in a Cas9 fusion protein is unlimited. In some embodiments, a Cas9 fusion protein comprises one or more (e.g. two or more, three or more, four or more, or five or more) heterologous sequences.

Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity, any of which can be directed at modifying nucleic acid directly (e.g., methylation of DNA or RNA) or at modifying a nucleic acid-associated polypeptide (e.g., a histone, a DNA binding protein, and RNA binding protein, and the like). Further suitable fusion partners include, but are not limited to boundary elements (e.g., CTCF), proteins and fragments thereof that provide periphery recruitment (e.g., Lamin A, Lamin B, etc.), and protein docking elements (e.g., FKBP/FRB, Pil1/Aby1, etc.).

Examples of various additional suitable fusion partners (or fragments thereof) for a subject variant Cas9 polypeptide include, but are not limited to those described in the PCT patent applications: WO2010/075303, WO2012/068627, and WO2013/155555 which are hereby incorporated by reference in their entirety.

Suitable fusion partners include, but are not limited to, a polypeptide that provides an activity that indirectly increases transcription by acting directly on the target nucleic acid or on a polypeptide (e.g., a histone, a DNA-binding protein, an RNA-binding protein, an RNA editing protein, etc.) associated with the target nucleic acid. Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity.

Additional suitable fusion partners include, but are not limited to, a polypeptide that directly provides for increased transcription and/or translation of a target nucleic acid (e.g., a transcription activator or a fragment thereof, a protein or fragment thereof that recruits a transcription activator, a small molecule/drug-responsive transcription and/or translation regulator, a translation-regulating protein, etc.).

Non-limiting examples of fusion partners to accomplish increased or decreased transcription include transcription activator and transcription repressor domains (e.g., the Kruppel associated box (KRAB or SKD); the Mad mSIN3 interaction domain (SID); the ERF repressor domain (ERD), etc.). In some such embodiments, a Cas9 fusion protein is targeted by the guide nucleic acid to a specific location (i.e., sequence) in the target nucleic acid and exerts locus-specific regulation such as blocking RNA polymerase binding to a promoter (which selectively inhibits transcription activator function), and/or modifying the local chromatin status (e.g., when a fusion sequence is used that modifies the target nucleic acid or modifies a polypeptide associated with the target nucleic acid). In some embodiments, the changes are transient (e.g., transcription repression or activation). In some embodiments, the changes are inheritable (e.g., when epigenetic modifications are made to the target nucleic acid or to proteins associated with the target nucleic acid, e.g., nucleosomal histones).

Non-limiting examples of fusion partners for use when targeting ssRNA target nucleic acids include (but are not limited to): splicing factors (e.g., RS domains); protein translation components (e.g., translation initiation, elongation, and/or release factors; e.g., eIF4G); RNA methylases; RNA editing enzymes (e.g., RNA deaminases, e.g., adenosine deaminase acting on RNA (ADAR), including A to I and/or C to U editing enzymes); heliembodiments; RNA-binding proteins; and the like. It is understood that a fusion partner can include the entire protein or in some embodiments can include a fragment of the protein (e.g., a functional domain).

In some embodiments, the heterologous sequence can be fused to the C-terminus of the Cas9 polypeptide. In some embodiments, the heterologous sequence can be fused to the N-terminus of the Cas9 polypeptide. In some embodiments, the heterologous sequence can be fused to an internal portion (i.e., a portion other than the N- or C-terminus) of the Cas9 polypeptide.

In addition the fusion partner of a chimeric Cas9 polypeptide can be any domain capable of interacting with ssRNA (which, for the purposes of this disclosure, includes intramolecular and/or intermolecular secondary structures, e.g., double-stranded RNA duplexes such as hairpins, stem-loops, etc.), whether transiently or irreversibly, directly or indirectly, including but not limited to an effector domain selected from the group comprising; Endonucleases (for example RNase I, the CRR22 DYW domain, Dicer, and PIN (PilT N-terminus) domains from proteins such as SMG5 and SMG6); proteins and protein domains responsible for stimulating RNA cleavage (for example CPSF, CstF, CFIm and CFIIm); Exonucleases (for example XRN-1 or Exonuclease T); Deadenylases (for example HNT3); proteins and protein domains responsible for nonsense mediated RNA decay (for example UPF1, UPF2, UPF3, UPF3b, RNP Si, Y14, DEK, REF2, and SRm160); proteins and protein domains responsible for stabilizing RNA (for example PABP); proteins and protein domains responsible for repressing translation (for example Ago2 and Ago4); proteins and protein domains responsible for stimulating translation (for example Staufen); proteins and protein domains responsible for (e.g., capable of) modulating translation (e.g., translation factors such as initiation factors, elongation factors, release factors, etc., e.g., eIF4G); proteins and protein domains responsible for polyadenylation of RNA (for example PAP1, GLD-2, and Star-PAP); proteins and protein domains responsible for polyuridinylation of RNA (for example CI D1 and terminal uridylate transferase); proteins and protein domains responsible for RNA localization (for example from IMP1, ZBP1, She2p, She3p, and Bicaudal-D); proteins and protein domains responsible for nuclear retention of RNA (for example Rrp6); proteins and protein domains responsible for nuclear export of RNA (for example TAP, NXF1, THO, TREX, REF, and Aly); proteins and protein domains responsible for repression of RNA splicing (for example PTB, Sam68, and hnRNP A1); proteins and protein domains responsible for stimulation of RNA splicing (for example Serine/Arginine-rich (SR) domains); proteins and protein domains responsible for reducing the efficiency of transcription (for example FUS (TLS)); and proteins and protein domains responsible for stimulating transcription (for example CDK7 and HIV Tat). Alternatively, the effector domain may be selected from the group comprising Endonucleases; proteins and protein domains capable of stimulating RNA cleavage; Exonucleases; Deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of modulating translation (e.g., translation factors such as initiation factors, elongation factors, release factors, etc., e.g., eIF4G); proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription. Another suitable fusion partner is a PUF RNA-binding domain, which is described in more detail in WO2012068627.

Some RNA splicing factors that can be used (in whole or as fragments thereof) as fusion partners for a Cas9 polypeptide have modular organization, with separate sequence-specific RNA binding modules and splicing effector domains. For example, members of the Serine/Arginine-rich (SR) protein family contain N-terminal RNA recognition motifs (RRMs) that bind to exonic splicing enhancers (ESEs) in pre-mRNAs and C-terminal RS domains that promote exon inclusion. As another example, the hnRNP protein hnRNP A1 binds to exonic splicing silencers (ESSs) through its RRM domains and inhibits exon inclusion through a C-terminal Glycine-rich domain. Some splicing factors can regulate alternative use of splice site (ss) by binding to regulatory sequences between the two alternative sites. For example, ASF/SF2 can recognize ESEs and promote the use of intron proximal sites, whereas hnRNP A1 can bind to ESSs and shift splicing towards the use of intron distal sites. One application for such factors is to generate ESFs that modulate alternative splicing of endogenous genes, particularly disease associated genes. For example, Bcl-x pre-mRNA produces two splicing isoforms with two alternative 5' splice sites to encode proteins of opposite functions. The long splicing isoform Bcl-xL is a potent apoptosis inhibitor expressed in long-lived postmitotic cells and is up-regulated in many cancer cells, protecting cells against apoptotic signals. The short isoform Bcl-xS is a pro-apoptotic isoform and expressed at high levels in cells with a high turnover rate (e.g., developing lymphocytes). The ratio of the two Bcl-x splicing isoforms is regulated by multiple cd-elements that are located in either the core exon region or the exon extension region (i.e., between the two alternative 5' splice sites). For more examples, see WO2010075303.

In some embodiments, a Cas9 polypeptide (e.g., a wild type Cas9, a variant Cas9, a variant Cas9 with reduced nuclease activity, etc.) can be linked to a fusion partner via a peptide spacer.

In some embodiments, a Cas9 polypeptide comprises a "Protein Transduction Domain" or PTD (also known as a CPP—cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD attached to another molecule facilitates entry of the molecule into the nucleus (e.g., in some embodiments, a PTD includes a nuclear localization signal (NLS)). In some embodiments, a Cas9 polypeptide comprises two or more NLSs, e.g., two or more NLSs in tandem. In some embodiments, a PTD is covalently linked to the amino terminus of a Cas9 polypeptide. In some embodiments, a PTD is covalently linked to the carboxyl terminus of a Cas9 polypeptide. In some embodiments, a PTD is covalently linked to the amino terminus and to the carboxyl terminus of a Cas9 polypeptide. In some embodiments, a PTD is covalently linked to a nucleic acid (e.g., a guide nucleic acid, a polynucleotide encoding a guide nucleic acid, a polynucleotide encoding a Cas9 polypeptide, etc.). Exemplary PTDs include but are not limited to a minimal undecapeptide protein transduction domain (corresponding to residues 47-57 of HIV-1 TAT comprising YGRKKRRQRRR; SEQ ID NO:7); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an Drosophila Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR (SEQ ID NO:8); Transportan GWTLNSAGYLLGKINLKALAALAKKIL (SEQ ID NO:9); KALAWEAKLAKALAKALAKHLAKA-LAKALKCEA (SEQ ID NO:10); and RQIKIWFQNRRMKWKK (SEQ ID NO:11). Exemplary PTDs include but are not limited to, YGRKKRRQRRR (SEQ ID NO:12), RKKRRQRRR (SEQ ID NO:13); an arginine homopolymer of from 3 arginine residues to 50 arginine residues; Exemplary PTD domain amino acid sequences include, but are not limited to, any of the following: YGRKKRRQRRR (SEQ ID NO:14); RKKRRQRR (SEQ ID NO:15); YARAAARQARA (SEQ ID NO:16); THRLPRRRRRR (SEQ ID NO:17); and GGRRARRRRRR (SEQ ID NO:18). In some embodiments, the PTD is an activatable CPP (ACPP) (Aguilera et al. (2009) Integr Biol (Camb) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

In some embodiments, the composition can comprise a Cpf1 RNA-guided endonuclease, an example of which is provided in FIG. 2, 11, or 12. Another name for the Cpf1 RNA-guided endonuclease is Cas12a. The Cpf1 CRISPR systems of the present disclosure comprise i) a single endonuclease protein, and ii) a crRNA, wherein a portion of the 3' end of crRNA contains the guide sequence complementary to a target nucleic acid. In this system, the Cpf1 nuclease is directly recruited to the target DNA by the crRNA. In some embodiments, guide sequences for Cpf1 must be at least 12 nt, 13 nt, 14 nt, 15 nt, or 16 nt in order to achieve detectable DNA cleavage, and a minimum of 14 nt, 15 nt, 16 nt, 17 nt, or 18 nt to achieve efficient DNA cleavage.

The Cpf1 systems of the present disclosure differ from Cas9 in a variety of ways. First, unlike Cas9, Cpf1 does not require a separate tracrRNA for cleavage. In some embodiments, Cpf1 crRNAs can be as short as about 42-44 bases long—of which 23-25 nt is guide sequence and 19 nt is the constitutive direct repeat sequence. In contrast, the combined Cas9 tracrRNA and crRNA synthetic sequences can be about 100 bases long.

Second, Cpf1 prefers a "TTN" PAM motif that is located 5' upstream of its target. This is in contrast to the "NGG" PAM motifs located on the 3' of the target DNA for Cas9 systems. In some embodiments, the uracil base immediately preceding the guide sequence cannot be substituted (Zetsche, B. et al. 2015. "Cpf1 Is a Single RNA-Guided Endonuclease of a Class 2 CRISPR-Cas System" Cell 163, 759-771, which is hereby incorporated by reference in its entirety for all purposes).

Third, the cut sites for Cpf1 are staggered by about 3-5 bases, which create "sticky ends" (Kim et al., 2016. "Genome-wide analysis reveals specificities of Cpf1 endonucleases in human cells" published online Jun. 6, 2016). These sticky ends with 3-5 bp overhangs are thought to facilitate NHEJ-mediated-ligation, and improve gene editing of DNA fragments with matching ends. The cut sites are in the 3' end of the target DNA, distal to the 5' end where the PAM is. The cut positions usually follow the 18th base on the non-hybridized strand and the corresponding 23rd base on the complementary strand hybridized to the crRNA.

Fourth, in Cpf1 complexes, the "seed" region is located within the first 5 nt of the guide sequence. Cpf1 crRNA seed regions are highly sensitive to mutations, and even single base substitutions in this region can drastically reduce cleavage activity (see Zetsche B. et al. 2015 "Cpf1 Is a Single RNA-Guided Endonuclease of a Class 2 CRISPR-Cas System" Cell 163, 759-771). Critically, unlike the Cas9 CRISPR target, the cleavage sites and the seed region of Cpf1 systems do not overlap. Additional guidance on designing Cpf1 crRNA targeting oligos is available on (Zetsche B. et al. 2015. "Cpf1 Is a Single RNA-Guided Endonuclease of a Class 2 CRISPR-Cas System" Cell 163, 759-771).

Persons skilled in the art will appreciate that the Cpf1 disclosed herein can be any variant derived or isolated from any source, many of which are known in the art. For example, in some embodiments, the Cpf1 peptide of the present disclosure can include FnCPF1 (e.g., SEQ ID NO: 2) set forth in FIG. 2, AsCpf1 (e.g., FIG. 16), LbCpf1 (e.g., FIG. 17) or any other of the many known Cpf1 proteins from various other microorganism species, or synthetic variants thereof.

In some embodiments, the composition comprises a Cpf1 polypeptide. In some embodiments, the Cpf1 polypeptide is enzymatically active, e.g., the Cpf1 polypeptide, when bound to a guide RNA, cleaves a target nucleic acid. In some embodiments, the Cpf1 polypeptide exhibits reduced enzymatic activity relative to a wild-type Cpf1 polypeptide (e.g., relative to a Cpf1 polypeptide comprising the amino acid sequence depicted in FIG. 2, 11, or 12), and retains DNA binding activity.

In some embodiments, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the amino acid sequence depicted in FIG. 2, 11, or 12. In some embodiments, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the amino acid sequence depicted in FIG. 2, 11, or 12.

In some embodiments, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of a Cpf1 polypeptide of the amino acid sequence depicted in FIG. 2, 11, or 12. In some embodiments, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of a Cpf1 polypeptide of the amino acid sequence depicted in FIG. 2, 11, or 12. In some embodiments, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of a Cpf1 polypeptide of the amino acid sequence depicted in FIG. 2, 11, or 12.

In some embodiments, the Cpf1 polypeptide exhibits reduced enzymatic activity relative to a wild-type Cpf1 polypeptide (e.g., relative to a Cpf1 polypeptide comprising the amino acid sequence depicted in FIG. 2, 11, or 12), and retains DNA binding activity. In some embodiments, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the amino acid sequence depicted in FIG. 2, 11, or 12; and comprises an amino acid substitution (e.g., a D→A substitution) at an amino acid residue corresponding to amino acid 917 of the amino acid sequence depicted in FIG. 2, 11, or 12. In some embodiments, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the amino acid sequence depicted in FIG. 2, 11, or 12; and comprises an amino acid substitution (e.g., an E→A substitution) at an amino acid residue corresponding to amino acid 1006 of the amino acid sequence depicted in FIG. 2, 11, or 12. In some embodiments, a Cpf1 polypeptide comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the amino acid sequence depicted in FIG. 2, 11, or 12; and comprises an amino acid substitution (e.g., a D→A substitution) at an amino acid residue corresponding to amino acid 1255 of the amino acid sequence depicted in FIG. 2, 11, or 12.

In some embodiments, the Cpf1 polypeptide is a fusion polypeptide, e.g., where a Cpf1 fusion polypeptide comprises: a) a Cpf1 polypeptide; and b) a heterologous fusion partner. In some embodiments, the heterologous fusion partner is fused to the N-terminus of the Cpf1 polypeptide. In some embodiments, the heterologous fusion partner is fused to the C-terminus of the Cpf1 polypeptide. In some embodiments, the heterologous fusion partner is fused to both the N-terminus and the C-terminus of the Cpf1 polypeptide. In some embodiments, the heterologous fusion partner is inserted internally within the Cpf1 polypeptide.

Suitable heterologous fusion partners include NLS, epitope tags, fluorescent polypeptides, and the like.

Linked Guide RNA and Donor Nucleic Acid

In one aspect, the invention provides a complex comprising a CRISPR system comprising an RNA-guided endonuclease (e.g. a Cas9 or Cpf1 polypeptide), a guide RNA and a donor polynucleotide, wherein the guide RNA and the donor polynucleotide are linked. As exemplified herein, the guide RNA and donor polynucleotide can be either covalently or non-covalently linked. In one embodiment, the guide RNA and donor polynucleotide are chemically ligated. In another embodiment, the guide RNA and donor polynucleotide are enzymatically ligated. In one embodiment, the guide RNA and donor polynucleotide hybridize to each other. In another embodiment, the guide RNA and donor polynucleotide both hybridize to a bridge sequence. Any number of such hybridization schemes are possible.

Deaminase

In some embodiments, the complex or composition further comprises a deaminase (e.g., an adenine base editor). As used herein, the term "deaminase" or "deaminase domain" refers to an enzyme that catalyzes the removal of an amine group from a molecule, or deamination. In some embodiments, the deaminase is a cytidine deaminase, catalyzing the hydrolytic deamination of cytidine or deoxy cytidine to uridine or deoxyuridine, respectively. In some embodiments, the deaminase is a cytosine deaminase, catalyzing the hydrolytic deamination of cytosine to uracil (e.g., in RNA) or thymine e.g., in DNA).

In some embodiments, the deaminase is an adenosine deaminase, which catalyzes the hydrolytic deamination of adenine or adenosine. In some embodiments, the deaminase or deaminase domain is an adenosine deaminase, catalyzing the hydrolytic deamination of adenosine or deoxyadenosine to inosine or deoxyinosine, respectively. In some embodiments, the adenosine deaminase catalyzes the hydrolytic deamination of adenine or adenosine in deoxyribonucleic acid (DNA). The adenosine deaminases (e.g. engineered adenosine deaminases, evolved adenosine deaminases) provided herein may be from any organism, such as a bacterium. In some embodiments, the deaminase or deaminase domain is a variant of a naturally-occurring deaminase from an organism, such as a human, chimpanzee, gorilla, monkey, cow, dog, rat, or mouse.

In some embodiments, the deaminase or deaminase domain does not occur in nature. For example, in some embodiments, the deaminase or deaminase domain is at least 50%, at least 55%, at least 60%, at least 65%, at least 70%, at least 75% at least 80%, at least 85%, at least 90% at least 95%, at least 96%, at least 97%, at least 98%, at least 99%, or at least 99.5% identical to a naturally-occurring deaminase. In some embodiments, the adenosine deaminase is from a bacterium, such as, *E. coli, S. aureus, S. typhi, S. putrefaciens, H. influenzae,* or *C. crescentus*. In some embodiments, the adenosine deaminase is a TadA deaminase. In some embodiments, the TadA deaminase is an *E. coli* TadA deaminase (ecTadA). In some embodiments, the TadA deaminase is a truncated *E. coli* TadA deaminase. For example, the truncated ecTadA may be missing one or more N-terminal amino acids relative to a full-length ecTadA. In some embodiments, the truncated ecTad A may be missing 1, 2, 3, 4, 5, 6, 7, 8, 9, 10, 11, 12, 13, 14, 15, 16, 17, 18, 19, or 20 N-terminal amino acid residues relative to the full length ecTadA. In some embodiments, the truncated ecTadA may be missing 1, 2, 3, 4, 5, 6, 7, 8, 9, 10, 11, 12, 13, 14, 15, 16, 17, 18, 19, or 20 C-terminal amino acid residues relative to the full length ecTadA. In some embodiments, the ecTadA deaminase does not comprise an N-terminal methionine. In some embodiments, the deaminase is APOBEC1 or a variant thereof.

The deaminase can be used in conjugation with any of the other CRISPR elements described herein (i.e., as a composition), or the deaminase can be fused to any of the other (CRISPR elements (e.g., Cas9 or (Cpf1) described herein (i.e., as a complex). In certain embodiments, the deaminase is fused to Cas9. Cpf1, or a variant thereof.

Other Components

The composition can further comprise any other components typically used in nucleic acid or protein delivery formulations. For instance, the composition can further comprise lipids, lipoproteins (e.g., cholesterol and derivatives), phospholipids, polymers or other components of liposomal or micellar delivery vehicles. The composition also can comprise solvent or carrier suitable for administration to cells or hosts, such as a mammal or human.

In some embodiments, the composition comprises a second polymer that comprises polyethylene oxide (PEG). For example, the composition can comprise PEG-pAsp(DET), PEG-pAsp, derivatives of PEG-pAsp(DET), derivatives of PEG-pAsp, or a combination thereof. Without wishing to be bound by any particular theory, it is believed that these PEGylated polymers can control the size of nanoparticles and their interaction with serum proteins and target cells.

The polyethylene oxide polymer can be combined with the other components in any manner and any order.

In some embodiments, the composition further comprises one or more surfactants. The surfactant can be anon-ionic surfactant and/or a zwitterionic surfactant. A list of exemplary surfactants includes, but is not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-6301NP-40); phospholipids such as phosphatidylcholine (lecithin); polyoxyethylene fatty ethers derived from lauryl, cetyl, stearyl and oleyl alcohols (known as Brij surfactants), such as triethyleneglycol monolauryl ether (Brij 30); polyoxyethylene-9-lauryl ether, and sorbitan esters (commonly known as the Spans), such as sorbitan trioleate (Span 85) and sorbitan monolaurate. In some embodiments, the surfactant is an anticoagulant (e.g., heparin or the like). In some embodiments, the composition further comprises one or more pharmaceutically acceptable carriers and/or excipients.

In some instances, a component (e.g., a nucleic acid component (e.g., a guide nucleic acid, etc.); a protein component (e.g., a Cas9 or Cpf1 polypeptide, a variant Cas9 or Cpf1 polypeptide); and the like) includes a label moiety. The terms "label", "detectable label", or "label moiety" as used herein refer to any moiety that provides for signal detection and may vary widely depending on the particular nature of the assay. Label moieties of interest include both directly detectable labels (direct labels)(e.g., a fluorescent label) and indirectly detectable labels (indirect labels)(e.g., a binding pair member). A fluorescent label can be any fluorescent label (e.g., a fluorescent dye (e.g., fluorescein, Texas red, rhodamine, ALEXAFLUOR® labels, and the like), a fluorescent protein (e.g., green fluorescent protein (GFP), enhanced GFP (EGFP), yellow fluorescent protein (YFP), red fluorescent protein (RFP), cyan fluorescent protein (CFP), cherry, tomato, tangerine, and any fluorescent derivative thereof), etc.). Suitable detectable (directly or indirectly) label moieties for use in the methods include any moiety that is detectable by spectroscopic, photochemical, biochemical, immunochemical, electrical, optical, chemical, or other means. For example, suitable indirect labels include biotin (a binding pair member), which can be bound by streptavidin (which can itself be directly or indirectly labeled). Labels can also include: a radiolabel (a direct label)(e.g., $^3$H, $^{125}$I, $^{35}$, $^{14}$C, or $^{32}$P); an enzyme (an indirect label)(e.g., peroxidase, alkaline phosphatase, galactosidase, luciferase, glucose oxidase, and the like); a fluorescent protein (a direct label)(e.g., green fluorescent protein, red fluorescent protein, yellow fluorescent protein, and any convenient derivatives thereof); a metal label (a direct label); a colorimetric label; a binding pair member; and the like. By "partner of a binding pair" or "binding pair member" is meant one of a first and a second moiety, wherein the first and the second moiety have a specific binding affinity for each other. Suitable binding pairs include, but are not limited to: antigen/antibodies (for example, digoxigenin/anti-digoxigenin, dinitrophenyl (DNP)/anti-DNP, dansyl-X-anti-dansyl, fluorescein/anti-fluorescein, lucifer yellow/anti-lucifer yellow, and rhodamine anti-rhodamine), biotin/avidin (or biotin/streptavidin) and calmodulin binding protein (CBP)/calmodulin. Any binding pair member can be suitable for use as an indirectly detectable label moiety.

Any given component, or combination of components can be unlabeled, or can be detectably labeled with a label moiety. In some embodiments, when two or more components are labeled, they can be labeled with label moieties that are distinguishable from one another.

Encapsulation and Nanoparticles

In some embodiments of the composition, the polymer combines with the nucleic acid and/or polypeptide and partially or completely encapsulates the nucleic acid and/or polypeptide. The composition can, in some formulations, provide a nanoparticle comprising the polymer and nucleic acid and/or polypeptide.

In some embodiments, the composition can comprise a core nanoparticle in addition to the polymer described herein and the nucleic acid or polypeptide. Any suitable nanoparticle can be used, including metal (e.g., gold) nanoparticles or polymer nanoparticles.

The polymer described herein and the nucleic acid (e.g., guide RNA, donor polynucleotide, or both) or polypeptide can be conjugated directly or indirectly to a nanoparticle surface. For example, the polymer described herein and the nucleic acid (e.g., guide RNA, donor polynucleotide, or both) or polypeptide can be conjugated directly to the surface of a nanoparticle or indirectly through an intervening linker.

Any type of molecule can be used as a linker. For example, a linker can be an aliphatic chain including at least two carbon atoms (e.g., 3, 4, 5, 6, 7, 8, 9, 10 or more carbon atoms), and can be substituted with one or more functional groups including ketone, ether, ester, amide, alcohol, amine, urea, thiourea, sulfoxide, sulfone, sulfonamide, and disulfide functionalities. In embodiments where the nanoparticle includes gold, a linker can be any thiol-containing molecule. Reaction of a thiol group with the gold results in a covalent sulfide (—S—) bond. Linker design and synthesis are well known in the art.

In some embodiments, the nucleic acid conjugated to the nanoparticle is a linker nucleic acid that serves to non-covalently bind one or more elements described herein (e.g., a Cas9 polypeptide, and a guide RNA, a donor polynucleotide, and a Cpf1 polypeptide) to the nanoparticle-nucleic acid conjugate. For instance, the linker nucleic acid can have a sequence that hybridizes to the guide RNA or donor polynucleotide.

The nucleic acid conjugated to the nanoparticle (e.g., a colloidal metal (e.g., gold) nanoparticle; a nanoparticle comprising a biocompatible polymer) can have any suitable length. When the nucleic acid is a guide RNA or donor polynucleotide, the length will be as suitable for such molecules, as discussed herein and known in the art. If the nucleic acid is a linker nucleic acid, it can have any suitable length for a linker, for instance, a length of from 10 nucleotides (nt) to 1000 nt, e.g., from about 1 nt to about 25 nt, from about 25 nt to about 50 nt, from about 50 nt to about 100 nt, from about 100 nt to about 250 nt, from about 250 nt to about 500 nt, or from about 500 nt to about 1000 nt. In some instances, the nucleic acid conjugated to the nanoparticle (e.g., a colloidal metal (e.g., gold) nanoparticle; a nanoparticle comprising a biocompatible polymer) nanoparticle can have a length of greater than 1000 nt.

When the nucleic acid linked (e.g., covalently linked; non-covalently linked) to a nanoparticle comprises a nucleotide sequence that hybridizes to at least a portion of the guide RNA or donor polynucleotide present in a complex of the present disclosure, it has a region with sequence identity to a region of the complement of the guide RNA or donor polynucleotide sequence sufficient to facilitate hybridization. In some embodiments, a nucleic acid linked to a nanoparticle in a complex of the present disclosure has at least 50%, at least 60%, at least 70%, at least 80%, at least 90%, at least 95%, at least 98%, at least 99%, or 100%, nucleotide sequence identity to a complement of from 10 to 50 nucleotides (e.g., from 10 nucleotides (nt) to 15 nt, from 15 nt to 20 nt, from 20 nt to 25 nt, from 25 nt to 30 nt, from 30 nt to 40 nt, or from 40 nt to 50 nt) of a guide RNA or donor polynucleotide present in the complex.

In some embodiments, a nucleic acid linked (e.g., covalently linked; non-covalently linked) to a nanoparticle is a donor polynucleotide, or has the same or substantially the same nucleotide sequence as a donor polynucleotide. In some embodiments, a nucleic acid linked (e.g., covalently linked; non-covalently linked) to a nanoparticle comprises a nucleotide sequence that is complementary to a donor DNA template.

Method of Use

Also provided herein is a method of delivering a nucleic acid and/or polypeptide to a cell, wherein the cell can be in vitro or in vivo. The method comprises administering a composition comprising the polymer and nucleic acid and/or polypeptide, as described herein, to the cell or to a subject containing the cell. The method can be used with respect to any type of cell or subject, but is particularly useful for mammalian cells (e.g., human cells). In some embodiments, the polymer comprises a targeting agent, such that nucleic acid and/or polypeptide is delivered predominantly or exclusively to target cells or tissues (e.g., cells or tissues of the peripheral nervous system, the central nervous system, the eye of the subject, liver, muscle, lung, bone (e.g., hematopoietic cells), or tumor cells or tissues).

When used with a composition comprising one or more components of a CRISPR system, the method may be employed to induce edit a target nucleic acid or gene. In some embodiments, a method of modifying a target nucleic acid comprises homology-directed repair (HDR). In some embodiments, use of a complex of the present disclosure to carry out HDR provides an efficiency of HDR of at least 1%, at least 2%, at least 3%, at least 4%, at least 5%, at least 10%, at least 15%, at least 20%, at least 25%, or more than 25%. In some embodiments, a method of modifying a target nucleic acid comprises non-homologous end joining (NHEJ). In some embodiments, use of a complex of the present disclosure to carry out HDR provides an efficiency of NHEJ of at least 1%, at least 2%, at least 3%, at least 4%, at least 5%, at least 10%, at least 15%, at least 20%, at least 25%, or more than 25%.

The following examples further illustrate the invention but, of course, should not be construed as in any way limiting its scope.

Example 1

This example provides guidance for the synthesis of Polymers A and B having a structure as described herein. The synthesis includes a ring-opening polymerization of a compound of Formula A. An exemplary procedure is as follows.

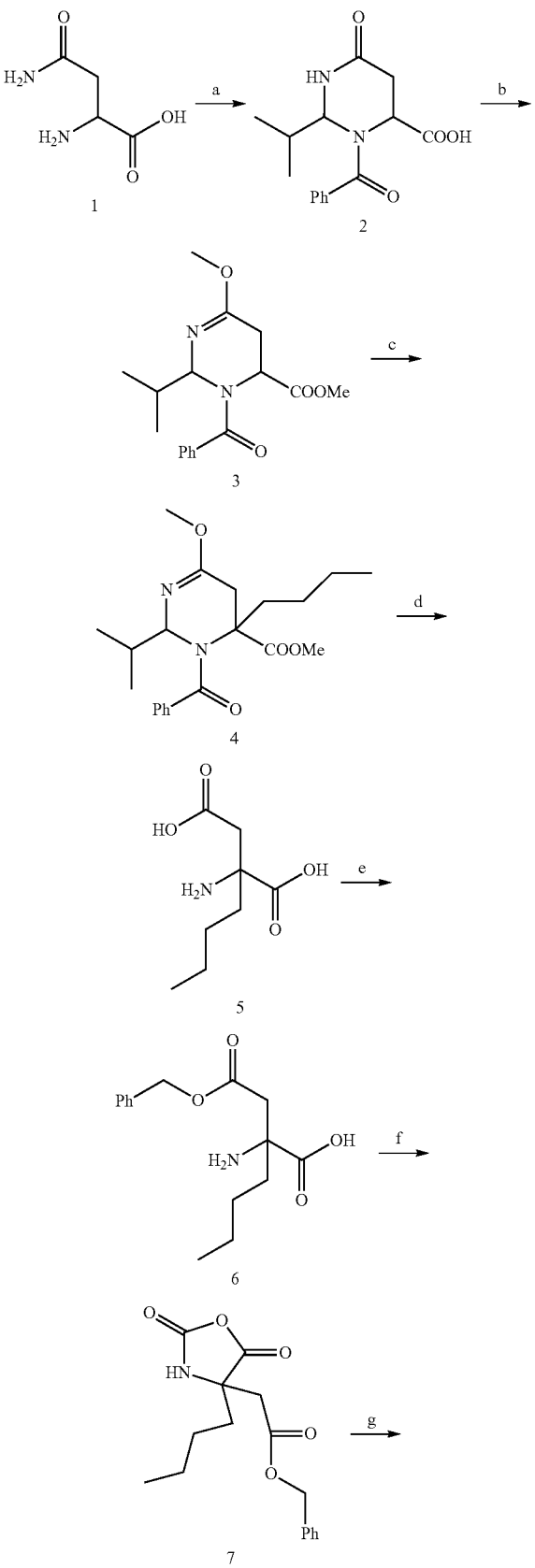

Scheme 1.

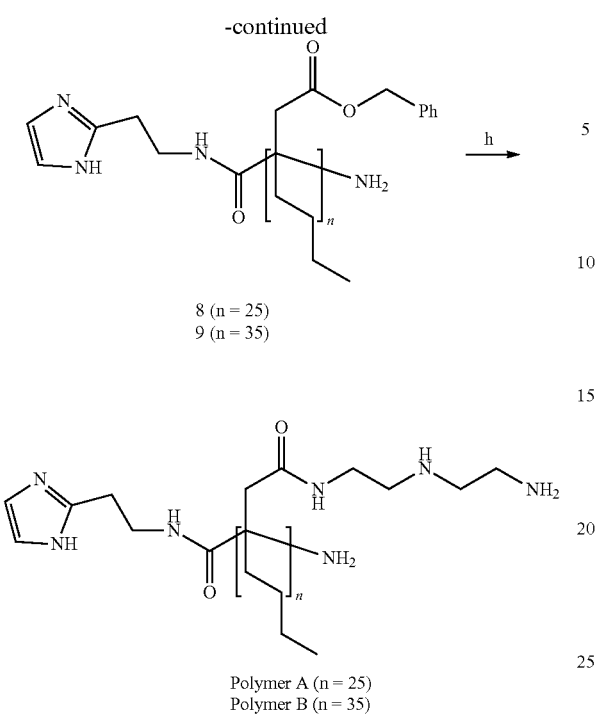

8 (n = 25)
9 (n = 35)

Polymer A (n = 25)
Polymer B (n = 35)

Synthesis of Polymer A and Polymer B: (a) i) KOH, Isobutyraldehyde, Methanol; ii) NaHCO$_3$, Benzoyl Chloride; (b) Ag$_2$O, CH$_3$I, THF, 6 days; (c) i) KHMDS, THF; ii) Iodobutane; d) HCl in methanol e) Benzyl alcohol, H$_2$SO$_4$; (f) Triphosgene, THF; (g) Imidazole amine, Toluene:THF (3:7), 48 hours; (h) DET, NMP, 24 hours.

In a glass vial, compound 7 (305 mg, 1 mmol) was dissolved into the mixture of toluene-THF (3:7). To this solution was added 3-aminopropylimidazole (1.25 mg, 0.01 mmol) and the resulting reaction mixture was stirred for 48 hours. The resulting polymer, 8 or 9, was precipitated into diethyl ether to yield a solid powder. $^1$HNMR (400 MHz, CDCl$_3$): δ 7.53 (m, 5H), 5.02 (dd, 2H), 2.82 (dd, 1H), 2.56 (dd, 1H), 1.37 (t, 2H), 1.23 (m, 4H), 0.82 (t, 3H). Polymer 8 (50 mg, 0.007 mmol) was suspended into N-methylpyrrolidone ("NMP") and the suspended solution was heated at 40° C. with stirring until the polymer dissolved in NMP. The solution was cooled to 0° C. and diethylenetriamine (1.78 gm, 17.36 mmol) was added drop-wise into the resulting solution. The resulting reaction mixture was stirred at room temperature for 24 hours to yield polymer A. Polymer A was purified by dialysis in 1M HCl for 12 hours and then water for 5 hours in a 5K MWCO dialysis bag. Polymer A was lyophilized to yield a solid powder. 1H NMR (400 MHz, D2O) d: 3.52 (t, 2H), 2.62-2.75 (m, 8H), 1.32-1.22 (m, 6H), 0.82 (t, 3H).

As demonstrated by Scheme 1, ring-opening polymerization of compound 7 results in propagation to form Polymers 8 and 9, which can be further modified to form Polymers A and B upon treatment with DET.

Example 2

This example provides guidance for the synthesis of additional Polymers C, D, and E having structures as described herein.

An exemplary procedure for the preparation of Polymer C is as follows:

Scheme 2.

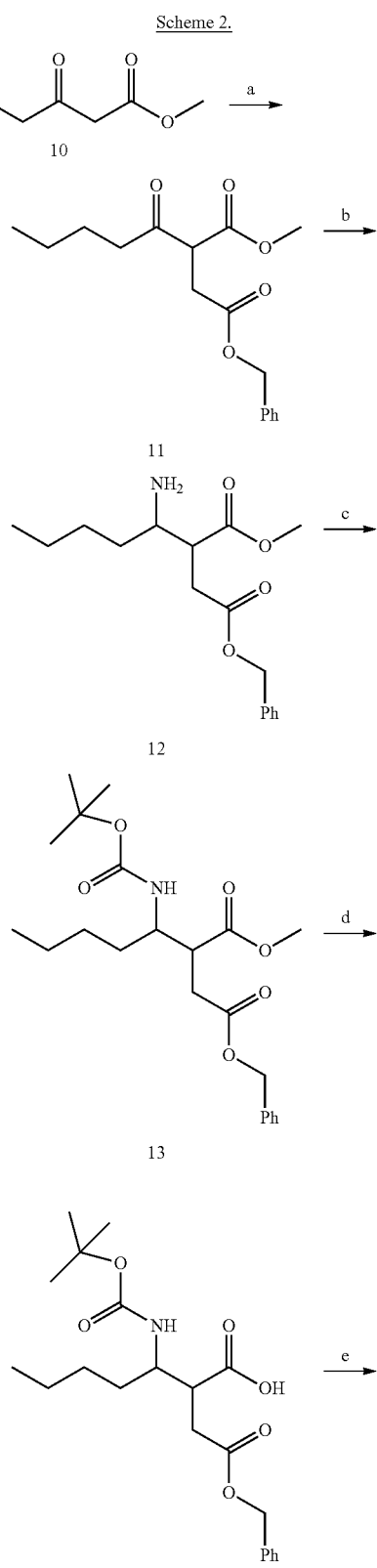

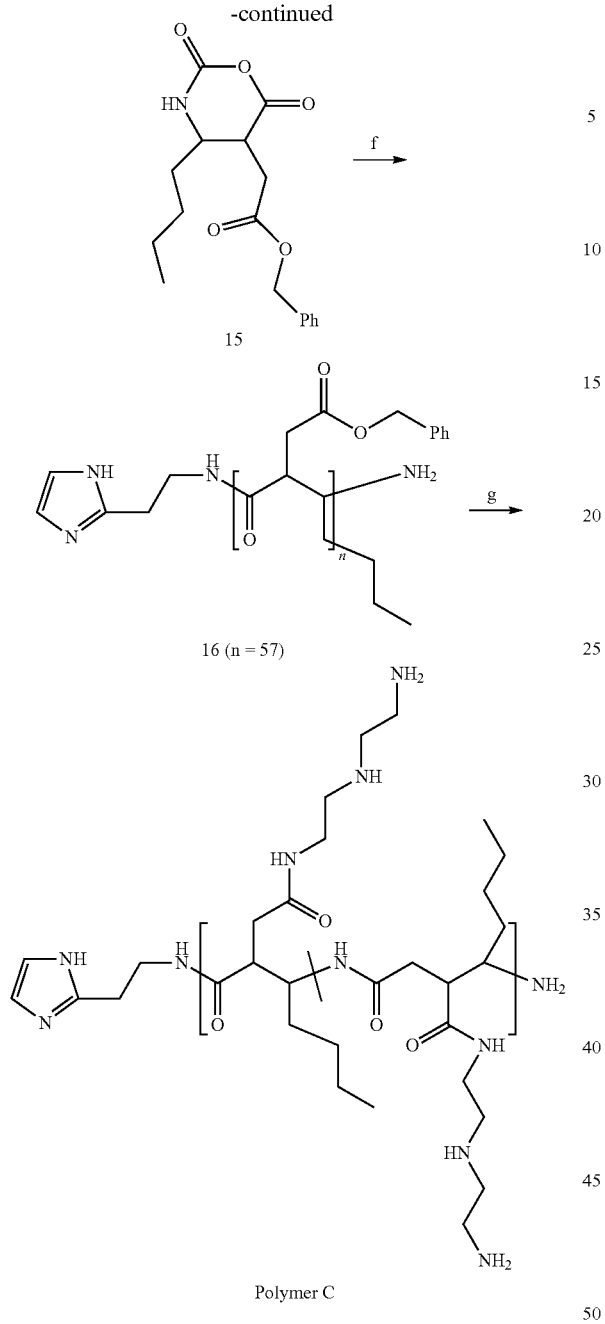

Polymer C

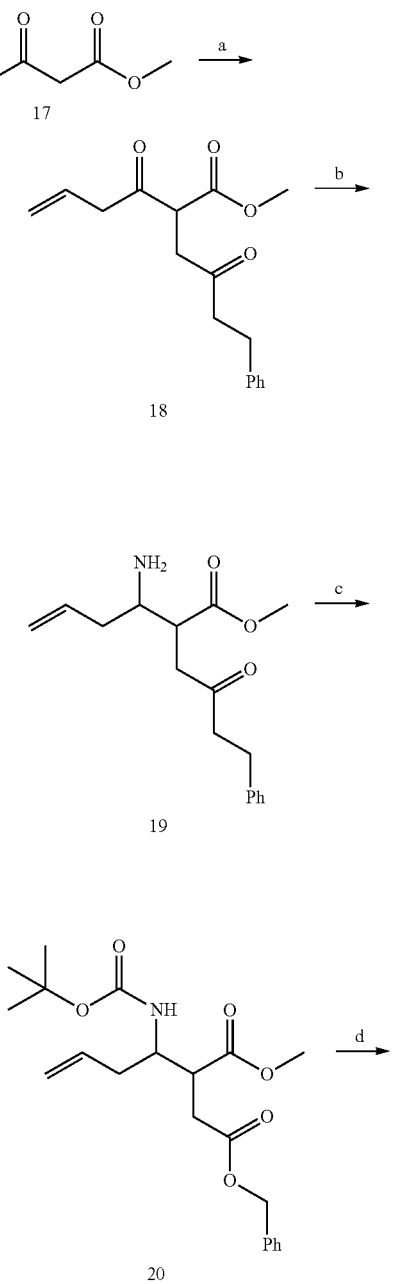

drop-wise to the solution. The resulting reaction mixture was stirred at rt for 24 hours to yield Polymer C. Polymer C was purified by dialysis in 1M HCl for 12 hours and then water for 5 hours in a 5K MWCO dialysis bag. Polymer C was lyophilized to yield a solid powder. 1H NMR (400 MHz, $D_2O$) d: 4.0-3.52 (m, 4H), 2.62-2.75 (m, 8H), 1.32-1.22 (m, 6H), 0.82 (t, 3H).

As demonstrated by Scheme 2, ring-opening polymerization of compound 15 results in propagation to form Polymer 16 with n=57, which can be further modified to form Polymer C upon treatment with DET.

Polymers D and E were prepared using the following procedure:

Synthesis of Polymer C: (a) i) THF, NaH; ii) Bromobenzylacetate; (b) ammonia in methanol, $NaBH_3CN$; (c) DCM, $(Boc)_2O$; (d) MeOH, 1M NaOH; (e) $POCl_3$, THF; (f) Imidazole amine, DCM, 48 hours; (g) DET, NMP, 6 hours.

In a glass vial, compound 15 (320 mg, 1 mmol) was dissolved into DCM. To this solution was added 3-aminopropylimidazole (1.25 mg, 0.01 mmol) and the resulting reaction mixture was stirred for 48 hours. Polymer 16 was precipitated into diethyl ether to yield a solid powder. $^1$HNMR (400 MHz, $CDCl_3$): δ 7.53 (m, 5H), 5.02 (dd, 2H), 4.05 (d, 1H), 3.42 (d, 1H) 2.82 (dd, 1H), 2.56 (dd, 1H), 1.37 (t, 2H), 1.23 (m, 4H), 0.82 (t, 3H). Polymer 16 (50 mg, 0.0027 mmol) was suspended into NMP and the suspended solution was heated at 40° C. with stirring until the polymer dissolved in NMP. The resulting solution was cooled to 0° C. and diethylenetriamine (1.62 gm, 15.65 mmol) was added

73
-continued

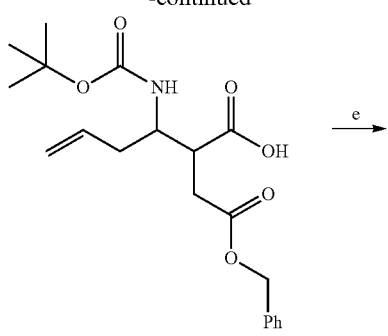
21

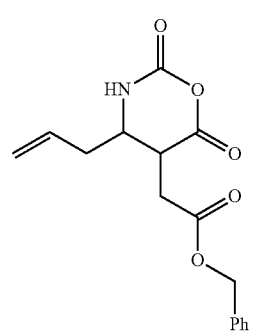
22

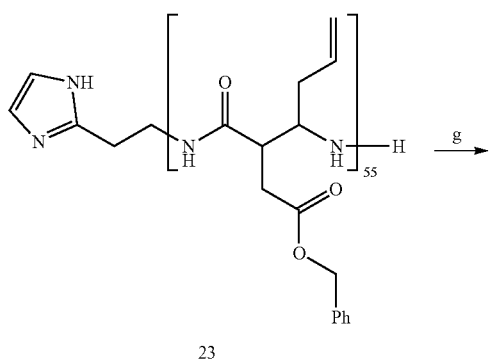
23

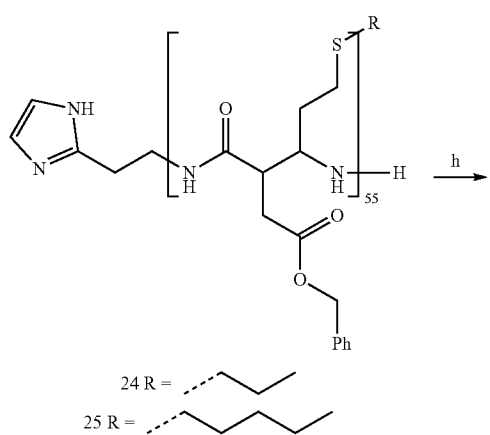

24 R = (propyl)
25 R = (pentyl)

74
-continued

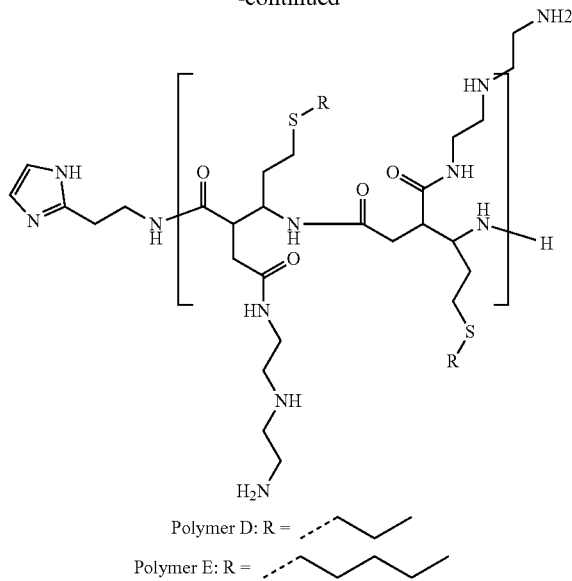

Polymer D: R = (propyl)
Polymer E: R = (pentyl)

Synthesis of Polymer D and E: (a) i) THF, NaH; ii) Bromo-benzylacetate; (b) Ammonia in Methanol, NaBH$_3$CN; (c) DCM, (BOC)$_2$O; (d) MeOH, 1M NaOH; (e) POCl$_3$, THF; (f) Imidazole amine, DCM, 48 hours; (g) AIBN, DMF, 70° C., 1-propanethiol (Synthesis of 24) and 1-pentanethiol (Synthesis of 25); (h) DET, NMP, 6 hours.

Synthesis of Polymer 23: In a dried round bottom flask was added 300 mg (0.989 mmol) of compound 22 and was dissolved into 10 mL of DCM. To this stirring solution was added histamine (1.83 mg, 0.016 mmol). The resulting solution was stirred at room temperature for 48 hours. Polymer 23 was precipitated into diethyl ether (4 mL of reaction mixture was added into 40 mL of diethyl ether). Polymer 23 was washed with ether and dried overnight under reduced pressure to yield Polymer 23 (210 mg, DP=55). 1H NMR (400 MHz, DMSO-d6): 7.33 (m, 5H), 5.82 (m, 1H), 5.13 (m, 1H), 5.02 (s, 2H), 4.88 (m, 1H), 2.92-2.83 (m, 4H), 2.29 (dd, 1H), 2.04 (dd, 1H).

Synthesis of Polymer 24: Polymer 23 (50 mg) was dissolved into DMF (6 mL) and to this solution was added 1-propanethiol (1.75 mL). The reaction mixture was heated up to 70 C and to this heated solution was added AIBN (8 mg). The resulting reaction mixture was stirred for 8 hours and then precipitated into 60 mL of diethyl ether. 1H NMR (400 MHz, DMSO-d6): 7.33 (m, 5H), 5.20 (s, 2H), 2.92-2.58 (m, 4H), 2.60 (m, 2H), 2.07-1.86 (m, 6H), 0.88 (t, 3H).

Synthesis of Polymer 25: Polymer 23 (50 mg) was dissolved into DMF (6 mL) and to this solution was added 1-pentanethiol (1.75 mL). The reaction mixture was heated up to 70 C and to this heated solution was added AIBN (8 mg). The resulting reaction mixture was stirred for 8 hours and then precipitated into 60 mL of diethyl ether. 1H NMR (400 MHz, DMSO-d6): 7.33 (m, 5H), 5.20 (s, 2H), 2.92-2.58 (m, 4H), 2.60 (m, 2H), 2.07-1.86 (m, 10H), 0.88 (t, 3H).

Synthesis of Polymer D: Polymer 24 (50 mg) was suspended into NMP and the suspended solution was heated at 40° C. with stirring until the polymer dissolved in NMP. The resulting solution was cooled to 0° C. and diethylenetriamine (1.62 gm, 15.65 mmol) was added drop-wise to the solution. The resulting reaction mixture was stirred at rt for 24 hours to yield Polymer D. Polymer D was purified by dialysis in 1M HCl for 12 hours and then water for 5 hours in a 5K MWCO dialysis bag. Polymer D was lyophilized to yield a solid powder. 1H NMR (400 MHz, D$_2$O) d: 4.0-3.52 (m, 4H), 2.75-2.62 (m, 8H), 2.07-1.78 (m, 6H), 0.82 (t, 3H).

Synthesis of Polymer E: Polymer 24 (50 mg) was suspended into NMP and the suspended solution was heated at 40° C. with stirring until the polymer dissolved in NMP. The resulting solution was cooled to 0° C. and diethylenetriamine (1.62 gm, 15.65 mmol) was added drop-wise to the solution. The resulting reaction mixture was stirred at rt for 24 hours to yield Polymer E. Polymer E was purified by dialysis in 1M HCl for 12 hours and then water for 5 hours in a 5K MWCO dialysis bag. Polymer E was lyophilized to yield a solid powder. 1H NMR (400 MHz, D$_2$O) d: 4.0-3.52 (m, 4H), 2.62-2.75 (m, 8H), 2.07-1.78 (m, 10H), 0.82 (t, 3H).

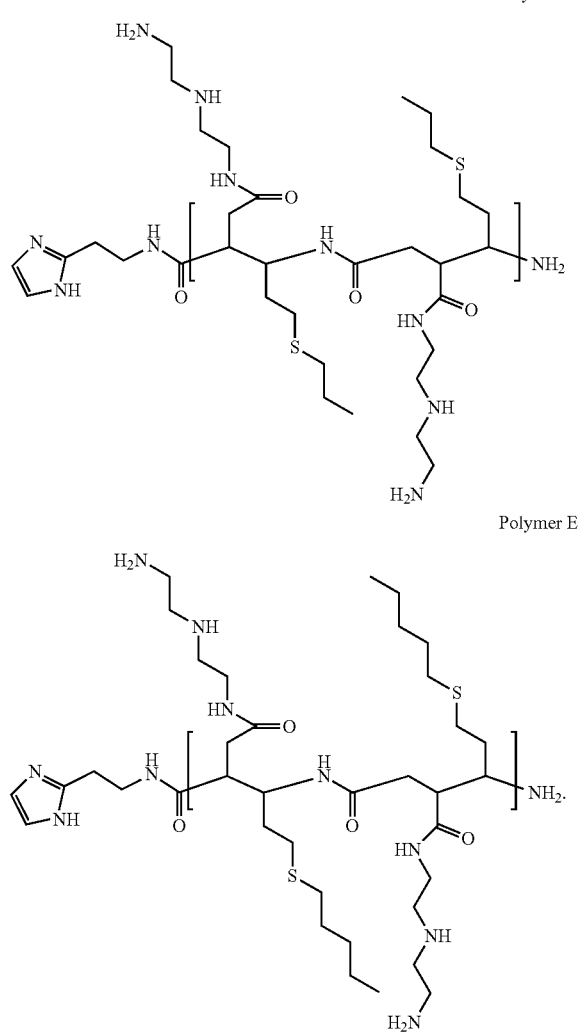

Example 3

This example demonstrates the ability of the polymers described herein to deliver Cre recombinase, which can change loxP sequences, into the cell.

Using traffic light reporter (TLR)-HEK 293T cells, which were generated with viral transduction of traffic light reporter in HEK 293T (see FIG. 3), the level of Cre recombinase delivered can be measured by red fluorescent protein ("RFP") expression. The traffic light reporter in HEK 293T contains a STOP cassette, and two loxP sequences that flank a GFP sequence, thereby preventing RFP transcription, and in turn expressing GFP in the absence of Cre. Cre recombinase removes the loxP sequences, and allows transcription of RFP.

Cre recombinase (1 ug) was mixed with (i) Polymer A, (ii) Polymer B, or (iii) Polymer C as prepared in Examples 1 and 2, or pAsp(DET) as a comparative, to produce nanoparticles. Polymers were added in dosages of 1.25 µg or 2.5 µg to screen an optimal dose that gives the highest efficiency and minimal toxicity. TLR-HEK293T cells were treated with the resulting nanoparticles, and the RFP+ population was quantified using flow cytometry 3 days after treatment. The results are set forth in FIG. 4.

Figure 4:
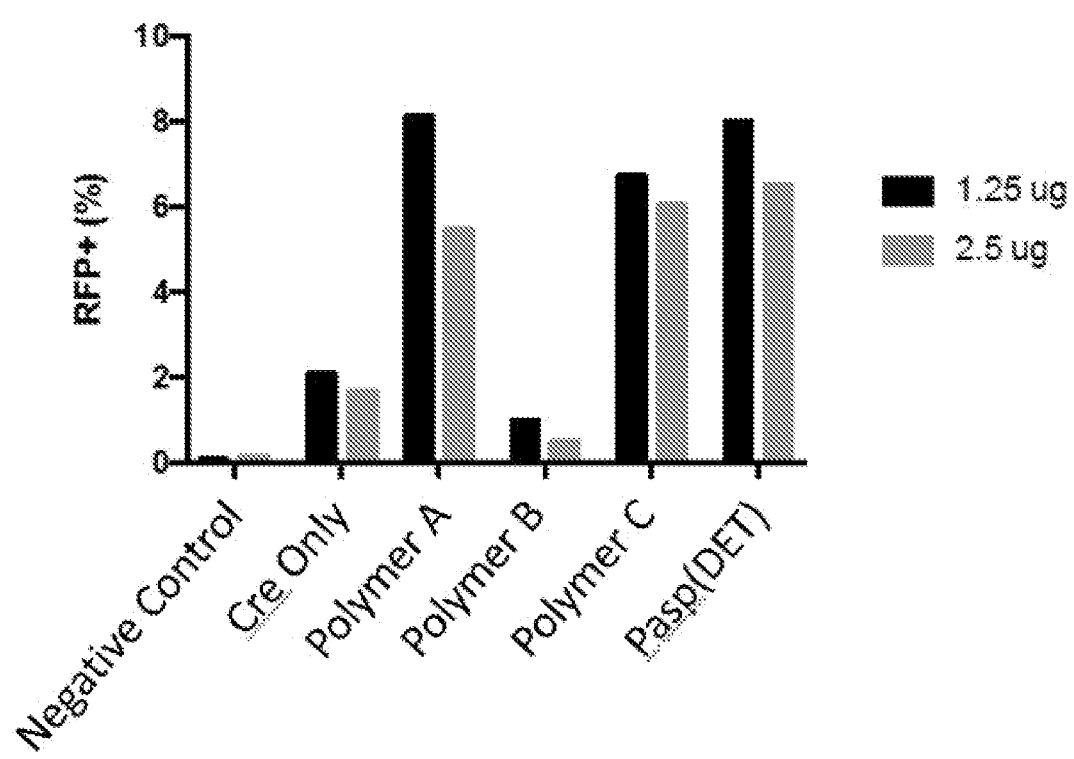
FIG. 4 shows the level of Cre recombinase delivery to TLR-HEK 293T as measured by the amount of RFP+ expression at different concentrations of polymer/Cre compositions.

FIG. 4 shows the level of Cre recombinase delivery to (TLR)-HEK 293T cells as measured by the amount of RFP+ expression. As shown in FIG. 4, Polymers A and C provided enhanced delivery over the sample containing Cre only. In addition, Polymers A and C produced levels of RFP+ expression consistent with the comparative, pAsp(DET), at polymer dosages of 1.25 µg and 2.5 µg.

Example 4

This example demonstrates the ability of the polymers described herein to deliver a Cas9 ribonucleoprotein ("Cas9 RNP") into the cell. The level of Cas9 RNP delivery was assessed using green fluorescent protein ("GFP") inducible HEK293T ("GFP-HEK") cells.

15 pmole of Cas9 RNP (sgRNA+Cas9 Protein) was mixed with (i) Polymer A, (ii) Polymer B, or (iii) Polymer C as prepared in Examples 1 and 2, or pAsp(DET) as a comparative, to produce nanoparticles. Polymers were added in dosages 2.5 µg. GFP-HEK cells were treated with the resulting mixture in non-serum conditions. The results are set forth in FIG. 5.

Figure 5:
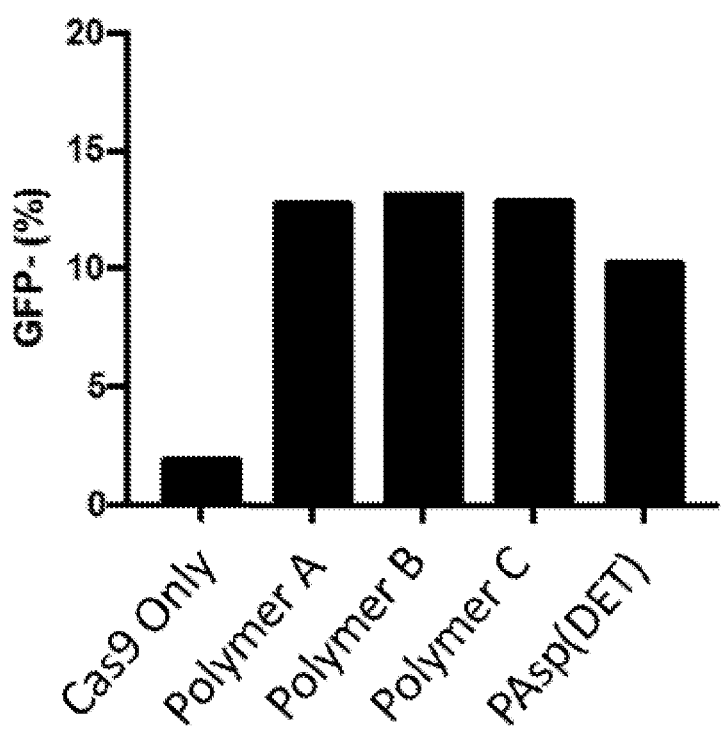
FIG. 5 is a graph of the level of Cas9 RNP delivery to GFP-HEK cells as measured by % GFP-cells at different dosages of polymer/Cas9 compositions.

FIG. 5 shows the level of Cas9 RNP delivery as measured by the GFP-% of the GFP-HEK cells treated with the four mixtures. All four polymers (i.e., Polymer A, Polymer B, Polymer C, and pAsp(DET)) showed an ability to deliver Cas9 RNP at a polymer dosage of 2.5 µg, relative to the control. However, Polymers A, B, and C outperformed pAsp(DET) at a polymer dosage of 2.5 µg.

Example 5

This example demonstrates the ability of the polymers described herein to deliver nucleic acids. The level of eGFP mRNA delivery to HEK 293T cells was assessed using green fluorescent protein ("GFP").

eGFP mRNA (200 ng) was mixed with Polymer C (600 ng) as prepared in Example 2, and incubated for 5 min. The resulting polymer nanoparticles were treated to HEK 293T cells in OptiMEM medium. After 24 hours, the cells were detached from the plate and analyzed with flow cytometry. Lipofectamine was used as a positive control for eGFP mRNA delivery. The results are set forth in FIG. 6.

Figure 6:
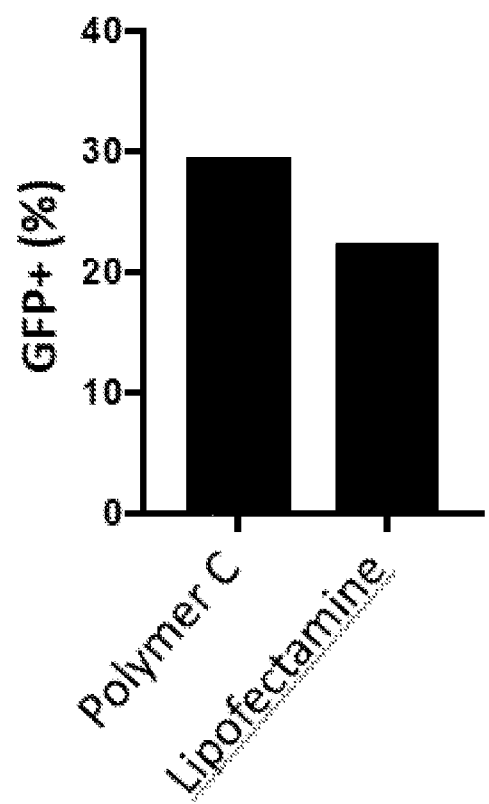
FIG. 6 illustrates the level of eGFP mRNA delivery to HEK 293T cells as measured by % GFP(+).

FIG. 6 shows that relative to the control, Polymer C provides increased delivery of eGFP mRNA to HEK 293T cells.

Example 6

This example demonstrates the effect incubation time has on the ability of the polymers described herein to deliver nucleic acids. The level of eGFP mRNA delivery to HEK 293T cells was assessed using green fluorescent protein ("GFP").

eGFP mRNA (200 ng) was mixed with Polymer C (1.2 µg) as prepared in Example 2, and incubated for periods of 2 min, 5 min, 10 min, and 30 min. The resulting polymer nanoparticles were treated to HEK 293T cells in OptiMEM medium. After 24 hours, the cells were detached from the plate and analyzed with flow cytometry. Lipofectamine was used as a positive control for eGFP mRNA delivery. The results are set forth in FIG. 7.

Figure 7:
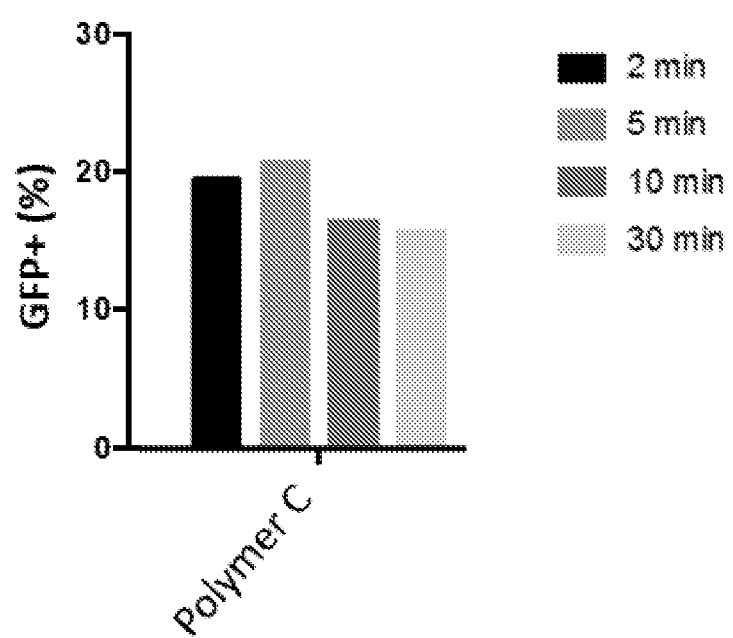
FIG. 7 shows the incubation time dependence of the level of eGFP mRNA delivery to HEK 293T cells as measured by % GFP(+).

FIG. 7 shows that nanoparticles formed within 2 minutes of incubation and polymer C provided efficient delivery of eGFP mRNA at all incubation times.

Example 7

This example demonstrates the ability of the polymers described herein to deliver plasmids. The level of red fluorescent protein ("RFP") encoding plasmid delivery to HEK 293T cells was assessed using RFP+ expression.

RFP plasmid (200 ng) was mixed with (i) Polymer A or (ii) Polymer C as prepared in Examples 1 and 2, or pAsp (DET) as a comparative to produce nanoparticles. Polymers A, C, and pAsp(DET) were added in dosages of (i) 600 ng or (ii) 480 ng in combination with 120 ng of a 1.5 kDa PEG-PAsp(DET) polymer. The 1.5 kDa PEG-PAsp(DET) polymer can help play a role in controlling the size of the nanoparticles. TLR-HEK293T cells were treated with the resulting nanoparticles, and the RFP+ population was quantified using flow cytometry 24 hours after treatment. The results are set forth in FIG. 8.

Figure 8:
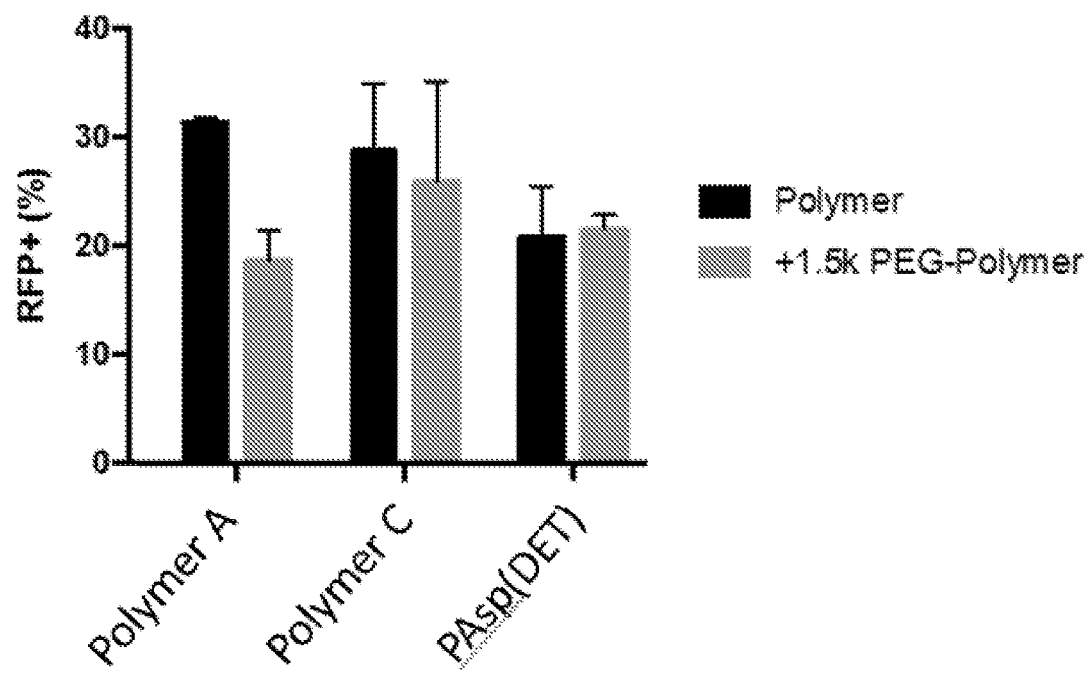
FIG. 8 illustrates level of red fluorescent protein ("RFP") encoding plasmid delivery to HEK 293T cells as measured by RFP+ expression in both the presence and absence of a 1.5 kDa PEG-PAsp(DET) polymer.

FIG. 8 shows that relative to the comparative polymer (PAsp(DET)), Polymers A and C provide comparable or improved delivery of plasmids to HEK 293T cells, both in the presence and in the absence of the 1.5 kDa PEG-PAsp (DET) polymer. In addition, FIG. 8 shows that 600 ng of Polymer A or Polymer C provide more efficient delivery of plasmids to HEK 293T cells than 480 ng Polymer A or Polymer C in combination with 120 ng of a 1.5 kDa PEG-PAsp(DET) polymer.

Example 8

This example demonstrates the ability of the polymers described herein to deliver plasmids. The level of red fluorescent protein ("RFP") encoding plasmid delivery to HEK 293T cells was assessed using RFP+ expression.

RFP plasmid (200 ng) was mixed with (i) Polymer A or (ii) Polymer C as prepared in Examples 1 and 2, or pAsp (DET) as a comparative to produce nanoparticles. Polymers A, C, and pAsp(DET) were added in dosages of (i) 1 µg or (ii) 800 ng in combination with 200 ng of a 1.5 kDa PEG-PAsp(DET) polymer. TLR-HEK293T cells were treated with the resulting nanoparticles, and the RFP+ population was quantified using flow cytometry 24 hours after treatment. The results are set forth in FIG. 9.

Figure 9:
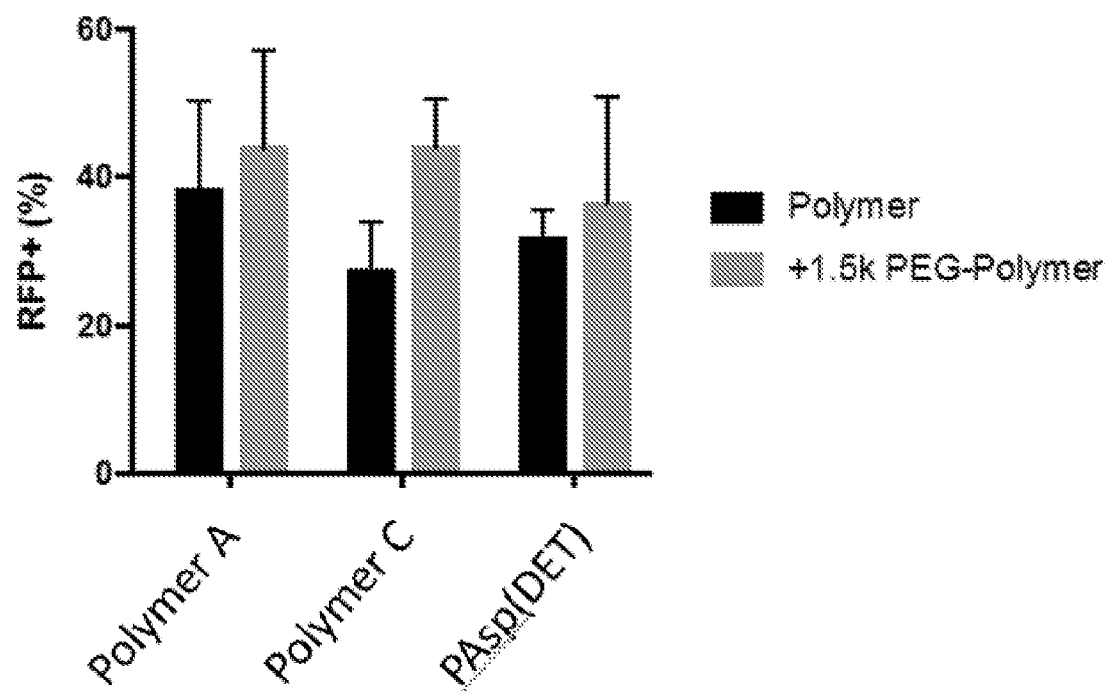
FIG. 9 illustrates level of red fluorescent protein ("RFP") encoding plasmid delivery to HEK 293T cells as measured by RFP+ expression in both the presence and absence of a 1.5 kDa PEG-PAsp(DET) polymer.

FIG. 9 shows that relative to the comparative polymer (PAsp(DET)), Polymers A and C provide comparable or improved delivery of plasmids to HEK 293T cells, both in the presence and in the absence of the 1.5 kDa PEG-PAsp (DET) polymer.

Example 9

This example demonstrates the ability of the polymers described herein to deliver a Cas9 ribonucleoprotein ("Cas9 RNP") into the cell using different buffers. The level of Cas9 RNP delivery was assessed using green fluorescent protein ("GFP") inducible HEK293T ("GFP-HEK") cells.

30 pmole of Cas9 RNP (sgRNA+Cas9 Protein) was mixed with 4 µg of (i) Polymer A or (ii) Polymer C as prepared in Examples 1 and 2, or 5 µg of pAsp(DET) as a comparative, to produce nanoparticles. GFP-HEK cells (200,000 cells) were treated under three different buffer conditions, namely (i) (4-(2-hydroxyethyl)-1-piperazineethanesulfonic acid) ("HEPES"; 20 mM), (ii) Opti-MEM™ (commercially available from Thermo Fisher Scientific; Waltham, MA), or Dulbecco's Modified Eagle's Medium ("DMEM"; commercially available from Thermo Fisher Scientific; Waltham, MA). The results are set forth in FIG. 10.

Figure 10:
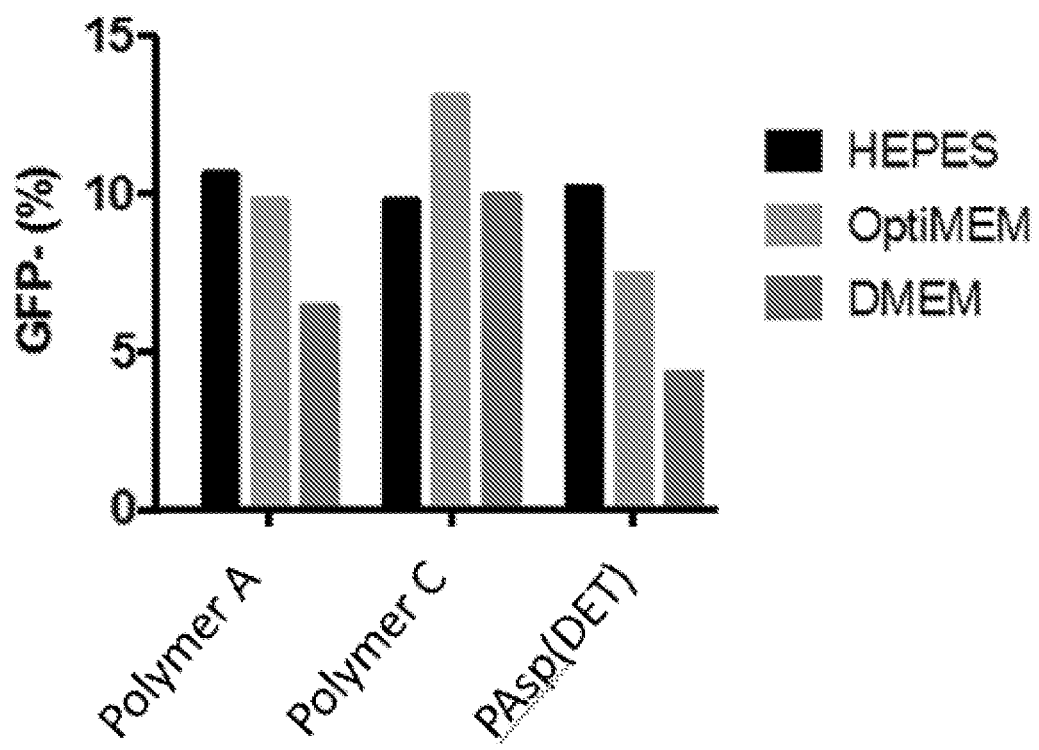
FIG. 10 is a graph of the level of Cas9 RNP delivery to GFP-HEK cells as measured by green fluorescence % GFP-cells for polymer/Cas9 nanoparticles in different buffers.

FIG. 10 shows the level of Cas9 RNP delivery as measured by the GFP-% of the GFP-HEK cells treated with the three mixtures (i.e., 4 µg or Polymer A or Polymer C, or 5 µg pAsp(DET)). All three polymers (i.e., Polymer A, Polymer C, and pAsp(DET)) showed an ability to deliver Cas9 RNP under the three different buffer conditions. Polymer A and pAsp(DET)) showed the same trend for the three different buffers, with HEPES outperforming Opti-MEM™, and Opti-MEM™ outperforming DMEM, while Polymer C performed best in the Opti-MEM™ buffer. Polymer A and Polymer C provided results consistent with, or outperformed pAsp(DET) under all three buffer conditions.

Example 10

This example demonstrates the use of the polymers described herein to deliver mRNA to a cell.

mRNA encoding green or red fluorescent protein was mixed with test polymer and combined with one of several different cell types as indicated in Tables 2 and 3. Transfection was measured as a function of fluorescence. The results are presented in Tables 2 and 3, which shows that almost all polymers produced some level of transfection in at least one cell type.

TABLE 2

| Polymer | Hepatocyte | | Mouse Primary Myoblast | | |
|---|---|---|---|---|---|
| | HUH-7 | HEPG2 | No-Serum | Serum | Neuron |
| A | 0 | 0 | 28 | 2 | 41 |
| B | 0 | 0 | 0 | 0 | 0 |
| C | 31 | 0 | 39 | 4 | 33 |
| D | 2 | 0 | 0 | N/A | N/A |
| E | 1 | 0 | 0 | N/A | N/A |
| Lipo | 84 | 43 | 39 | 52 | 22 |
| Mock | 0 | 0 | 0 | 0 | N/A |
| pAsp[DET] | 0 | 0 | N/A | N/A | N/A |

TABLE 3

| Polymer | Human Neural Stem Cell | | HEK293 |
|---|---|---|---|
| | No-Serum | Serum | No-Serum |
| A | 44 | 4 | 30 |
| B | 0 | 1 | 0 |
| C | 43 | 3 | 28 |
| D | N/A | N/A | 12 |
| E | N/A | N/A | 11 |
| Lipo | 58.6 | N/A | 26 |
| Mock | N/A | N/A | N/A |
| pAsp[DET] | 39 | 3 | 28 |

In Tables 2 and 3:
N/A=Not tested
Lipo=lipofectamine
Mock=polymer without mRNA
Mouse primary myoblast testing was performed using mRNA encoding green fluorescent protein. All other cell types were tested using mRNA encoding red fluorescent protein.

Example 11

This example demonstrates the use of the polymers described herein to deliver Cas9 ribonucleoprotein (Cas9 RNP) to a cell.

GFP-HEK cells were transfected with Cas9 RNP formulated with polymer D or E in non-serum medium. Flow cytometry was conducted 4 days after the transfection. About 15% of the treated cells lost GFP expression due to GFP gene knock-out by Cas9 RNP.

Preferred embodiments of this invention are described herein, including the best mode known to the inventors for carrying out the invention. Variations of those preferred embodiments can become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a complex" includes a plurality of such complexes and reference to "the Cas9 polypeptide" includes reference to one or more Cas9 polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The invention claimed is:

1. A polymer comprising a structure of Formula 1:

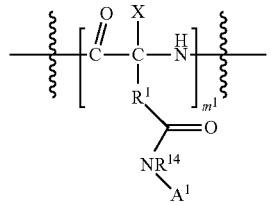

wherein,
$m^1$ is an integer from 1 to 2000;
$R^1$ is a methylene or ethylene group;
$R^{14}$ is hydrogen or a $C_1$-$C_{12}$ alkyl group, alkenyl group, cycloalkyl group, or cycloalkenyl group;
X is a $C_1$-$C_{12}$ alkyl group, cycloalkyl group, alkenyl group, cycloalkenyl group, aryl group, heteroalkyl group, or heterocyclic group;
$A^1$ is a group of formula —$(CH_2)_{p1}$—[$NR^2$—$(CH_2)_{q1}$—]$_{r1}NR^2_2$;

—$(CH_2)_{p2}$—N[—$(CH_2)_{q2}$—$NR^2_2$]$_2$;

—$(CH_2)_{p3}$—N{[—$(CH_2)_{q3}$—$NR^2_2$][—$(CH_2)_{q4}$—$NR^2$—]$_{r2}R^2$}; or

—$(CH_2)_{p4}$—N{—$(CH_2)_{q5}$—N[—$(CH_2)_{q6}$—$NR^2_2$]$_2$}$_2$, wherein p1 to p4, q1 to q6, and r1 and r2 are each independently an integer of 1 to 5; and
each instance of $R^2$ is independently hydrogen or a $C_1$-$C_{12}$ alkyl group, alkenyl group, cycloalkyl group, or cycloalkenyl group.

2. The polymer of claim 1, having the structure of Formula 1A:

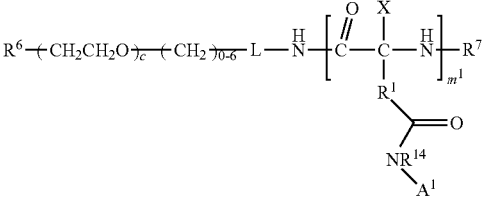

wherein,
c is an integer from 0 to 50;
L is optionally present and is a cleavable linker;
$m^1$ is an integer from 1 to 2000;
$R^1$ is a methylene or ethylene group;
$R^6$ is hydrogen, an amino group, an aryl group, a heterocyclic group, a $C_1$-$C_{12}$ alkyl group, alkenyl group, cycloalkyl group, or cycloalkenyl group, a $C_1$-$C_{12}$ linear or branched alkyl group optionally substituted with one or more amines; or a tissue-specific or cell-specific targeting moiety;
$R^7$ is hydrogen, an aryl group, a heterocyclic group, a $C_1$-$C_{12}$ alkyl group, alkenyl group, cycloalkyl group, or cycloalkenyl group, or a $C_1$-$C_{12}$ linear or branched alkyl group optionally substituted with one or more substituents;
$R^{14}$ is hydrogen or a $C_1$-$C_{12}$ alkyl group, alkenyl group, cycloalkyl group, or cycloalkenyl group;
X is a $C_1$-$C_{12}$ alkyl group, cycloalkyl group, alkenyl group, cycloalkenyl group, aryl group, heteroalkyl group, or heterocyclic group;
$A^1$ is a group of formula

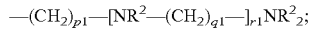

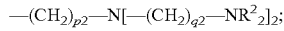

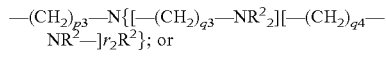

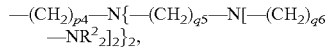

wherein p1 to p4, q1 to q6, and r1 and r2 are each independently an integer of 1 to 5; and
each instance of $R^2$ is independently hydrogen or a $C_1$-$C_{12}$ alkyl group, alkenyl group, cycloalkyl group, or cycloalkenyl group.

3. The polymer of claim 1, comprising a structure of Formula 2:

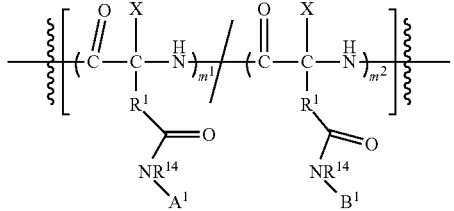

wherein,
$m^1$ is an integer from 1 to 1000;
$m^2$ is an integer from 1 to 1000;
the symbol "/" indicates that the units separated thereby are linked randomly or in any order;
each $R^1$ independently is a methylene or ethylene group;
each instance of $R^{14}$ is independently hydrogen or a $C_1$-$C_{12}$ alkyl group, alkenyl group, cycloalkyl group, or cycloalkenyl group;
each instance of X is independently a $C_1$-$C_{12}$ alkyl group, cycloalkyl group, alkenyl group, cycloalkenyl group, aryl group, heteroalkyl group, or heterocyclic group;

$A^1$ is a group of formula

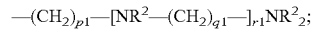

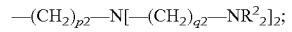

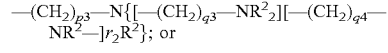

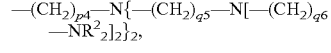

$B^1$ is a group of formula

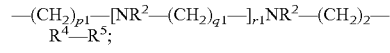

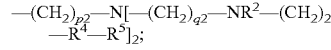

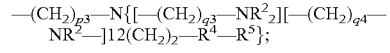

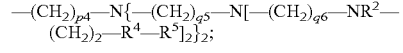

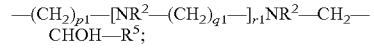

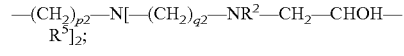

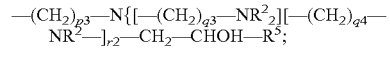

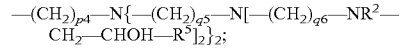

wherein p1 to p4, q1 to q6, and r1 and r2 are each independently an integer of 1 to 5; each instance of $R^2$ is independently hydrogen or a $C_1$-$C_{12}$ alkyl group, alkenyl group, cycloalkyl group, or cycloalkenyl group; each instance of $R^4$ is independently —C(O)O—, —C(O)NH—, or —S(O)(O)—; and each instance of $R^5$ is independently an alkyl group, cycloalkyl group, alkenyl group, cycloalkenyl group, aryl group, heteroalkyl group, or heterocyclic group optionally comprising from 2 to 8 tertiary amines or a substituent comprising a tissue-specific or cell-specific targeting moiety.

4. The polymer of claim 3, having the structure of Formula 2A:

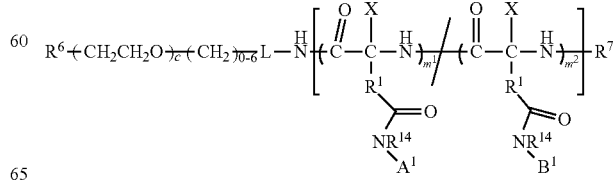

wherein,
c is an integer from 0 to 50;
L is optionally present and is a cleavable linker;
$m^1$ is an integer from 1 to 1000;
$m^2$ is an integer from 1 to 1000;
the symbol "/" indicates that the units separated thereby are linked randomly or in any order;
each $R^1$ independently is a methylene or ethylene group;
$R^6$ is hydrogen, an amino group, an aryl group, a heterocyclic group, a $C_1$-$C_{12}$ alkyl group, alkenyl group, cycloalkyl group, or cycloalkenyl group, a $C_1$-$C_{12}$ linear or branched alkyl group optionally substituted with one or more amines; or a tissue-specific or cell-specific targeting moiety;
$R^7$ is hydrogen, an aryl group, a heterocyclic group, a $C_1$-$C_{12}$ alkyl group, alkenyl group, cycloalkyl group, or cycloalkenyl group, or a $C_1$-$C_{12}$ linear or branched alkyl group optionally substituted with one or more substituents;
each instance of $R^{14}$ is independently hydrogen or a $C_1$-$C_{12}$ alkyl group, alkenyl group, cycloalkyl group, or cycloalkenyl group;
each instance of X is independently a $C_1$-$C_{12}$ alkyl group, cycloalkyl group, alkenyl group, cycloalkenyl group, aryl group, heteroalkyl group, or heterocyclic group;
$A^1$ is a group of formula

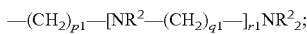

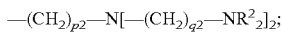

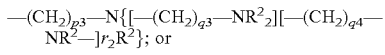

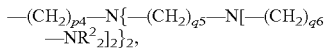

$B^1$ is a group of formula

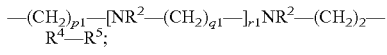

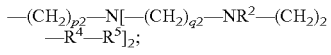

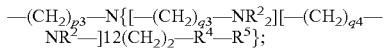

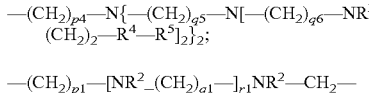

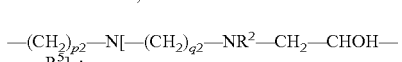

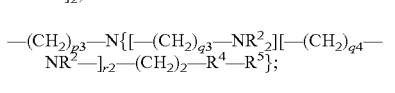

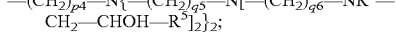

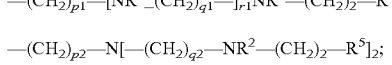

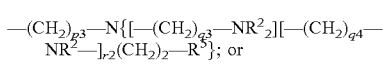

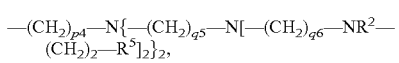

wherein p1 to p4, q1 to q6, and r1 and r2 are each independently an integer of 1 to 5; each instance of $R^2$ is independently hydrogen or a $C_1$-$C_{12}$ alkyl group, alkenyl group, cycloalkyl group, or cycloalkenyl group; each instance of $R^4$ is independently —C(O)O—, —C(O)NH—, or —S(O)(O)—; and each instance of $R^5$ is independently an alkyl group, cycloalkyl group, alkenyl group, cycloalkenyl group, aryl group, heteroalkyl group, or heterocyclic group optionally comprising from 2 to 8 tertiary amines or a substituent comprising a tissue-specific or cell-specific targeting moiety.

5. A method of preparing a polymer according to claim 3 comprising a structure of Formula 2:

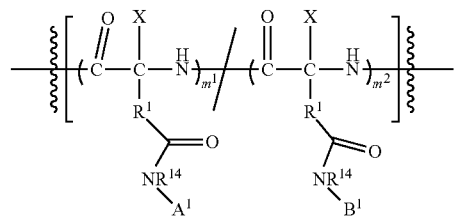

wherein,
$m^1$ is an integer from 1 to 1000;
$m^2$ is an integer from 1 to 1000;
the symbol "/" indicates that the units separated thereby are linked randomly or in any order;
each $R^1$ independently is a methylene or ethylene group;
each instance of $R^{14}$ is independently hydrogen or a $C_1$-$C_{12}$ alkyl group, alkenyl group, cycloalkyl group, or cycloalkenyl group;
each instance of X is independently a $C_1$-$C_{12}$ alkyl group, cycloalkyl group, alkenyl group, cycloalkenyl group, aryl group, heteroalkyl group, or heterocyclic group;
$A^1$ is a group of formula

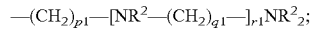

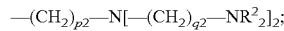

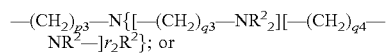

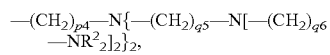

$B^1$ is a group of formula

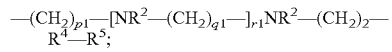

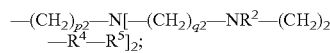

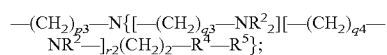

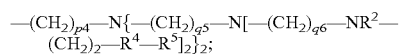

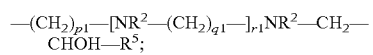

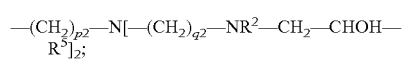

—(CH$_2$)$_{p3}$—N{[—(CH$_2$)$_{q3}$—NR$^2$$_2$][—(CH$_2$)$_{q4}$—NR$^2$—]$_{r2}$—CH$_2$—CHOH—R$^5$;

—(CH$_2$)$_{p4}$—N{—(CH$_2$)$_{q5}$—N[—(CH$_2$)$_{q6}$—NR$^2$—CH$_2$—CHOH—R$^5$]$_2$}$_2$;

—(CH$_2$)$_{p1}$—[NR$^2$—(CH$_2$)$_{q1}$—]$_{r1}$NR$^2$—(CH$_2$)$_2$—R$^5$;

—(CH$_2$)$_{p2}$—N[—(CH$_2$)$_{q2}$—NR$^2$—(CH$_2$)$_2$—R$^5$]$_2$;

—(CH$_2$)$_{p3}$—N{[—(CH$_2$)$_{q3}$—NR$^2$$_2$][—(CH$_2$)$_{q4}$—NR$^2$—]12(CH$_2$)$_2$—R$^5$}; or

—(CH$_2$)$_{p4}$—N{—(CH$_2$)$_{q5}$—N[—(CH$_2$)$_{q6}$—NR$^2$—(CH$_2$)$_2$—R$^5$]$_2$}$_2$, wherein p1 to p4, q1 to q6, and r1 and r2 are each independently an integer of 1 to 5;

each instance of R$^2$ is independently hydrogen or a C$_1$-C$_{12}$ alkyl group, alkenyl group, cycloalkyl group, or cycloalkenyl group; each instance of R$^4$ is independently —C(O)O—, —C(O)NH—, or —S(O)(O)—; and each instance of R$^5$ is independently an alkyl group, cycloalkyl group, alkenyl group, cycloalkenyl group, aryl group, heteroalkyl group, or heterocyclic group optionally comprising from 2 to 8 tertiary amines or a substituent comprising a tissue-specific or cell-specific targeting moiety from a polymer comprising a structure of Formula 1:

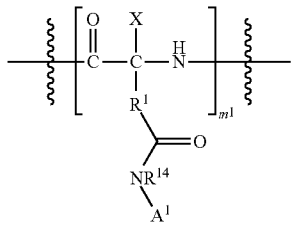

wherein,
m$^1$ is an integer from 1 to 2000;
R$^1$ is a methylene or ethylene group;
R$^{14}$ is hydrogen or a C$_1$-C$_{12}$ alkyl group, alkenyl group, cycloalkyl group, or cycloalkenyl group;
X is a C$_1$-C$_{12}$ alkyl group, cycloalkyl group, alkenyl group, cycloalkenyl group, aryl group, heteroalkyl group, or heterocyclic group;
A$^1$ is a group of formula —(CH$_2$)$_{p1}$—[NR$^2$—(CH$_2$)$_{q1}$—]$_{r1}$NR$^2$$_2$;

—(CH$_2$)$_{p2}$—N[—(CH$_2$)$_{q2}$—NR$^2$$_2$]$_2$;

—(CH$_2$)$_{p3}$—N{[—(CH$_2$)$_{q3}$—NR$^2$$_2$][—(CH$_2$)$_{q4}$—NR$^2$—]$_{r2}$R$^2$}; or

—(CH$_2$)$_{p4}$—N{—(CH$_2$)$_{q5}$—N[—(CH$_2$)$_{q6}$—NR$^2$$_2$]$_2$}$_2$, wherein p1 to p4, q1 to q6, and r1 and r2 are each independently an integer of 1 to 5; and each instance of R$^2$ is independently hydrogen or a C$_1$-C$_{12}$ alkyl group, alkenyl group, cycloalkyl group, or cycloalkenyl group, the method comprising modifying at least a portion of groups designated A$^1$ to produce groups designated B$^1$.

6. The method of claim 5, wherein the polymer comprising a structure of Formula 2 is a polymer of Formula 2A:

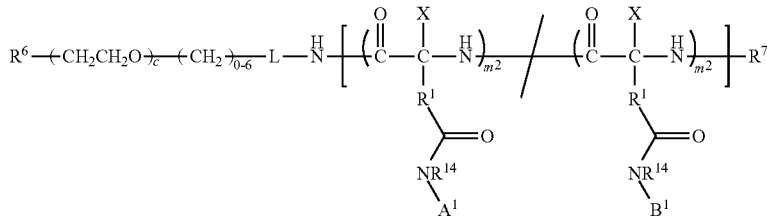

wherein,
c is an integer from 0 to 50;
L is optionally present and is a cleavable linker;
m$^1$ is an integer from 1 to 1000;
m$^2$ is an integer from 1 to 1000;
the symbol "/" indicates that the units separated thereby are linked randomly or in any order;
each R$^1$ independently is a methylene or ethylene group;
R$^6$ is hydrogen, an amino group, an aryl group, a heterocyclic group, a C$_1$-C$_{12}$ alkyl group, alkenyl group, cycloalkyl group, or cycloalkenyl group, a C$_1$-C$_{12}$ linear or branched alkyl group optionally substituted with one or more amines; or a tissue-specific or cell-specific targeting moiety;
R$^7$ is hydrogen, an aryl group, a heterocyclic group, a C$_1$-C$_{12}$ alkyl group, alkenyl group, cycloalkyl group, or cycloalkenyl group, or a C$_1$-C$_{12}$ linear or branched alkyl group optionally substituted with one or more substituents;
each instance of R$^{14}$ is independently hydrogen or a C$_1$-C$_{12}$ alkyl group, alkenyl group, cycloalkyl group, or cycloalkenyl group;
each instance of X is independently a C$_1$-C$_{12}$ alkyl group, cycloalkyl group, alkenyl group, cycloalkenyl group, aryl group, heteroalkyl group, or heterocyclic group;
A$^1$ is a group of formula —(CH$_2$)$_{p1}$—[NR$^2$—(CH$_2$)$_{q1}$—]$_{r1}$NR$^2$$_2$;

—(CH$_2$)$_{p2}$—N[—(CH$_2$)$_{q2}$—NR$^2$$_2$]$_2$;

—(CH$_2$)$_{p3}$—N{[—(CH$_2$)$_{q3}$—NR$^2$$_2$][—(CH$_2$)$_{q4}$—NR$^2$—]$_{r2}$R$^2$}; or

—(CH$_2$)$_{p4}$—N{—(CH$_2$)$_{q5}$—N[—(CH$_2$)$_{q6}$—NR$^2$$_2$]$_2$}$_2$, $B^1$ is a group of formula $-(CH_2)_{p1}-[NR^2-(CH_2)_{q1}-]_{r1}NR^2-(CH_2)_2-R^4-R^5;$ $-(CH_2)_{p2}-N[-(CH_2)_{q2}-NR^2-(CH_2)_2-R^4-R^5]_2;$ $-(CH_2)_{p3}-N\{[-(CH_2)_{q3}-NR^2_2][-(CH_2)_{q4}-NR^2-]_{r2}(CH_2)_2-R^4-R^5\};$ $-(CH_2)_{p4}-N\{-(CH_2)_{q5}-N[-(CH_2)_{q6}-NR^2-(CH_2)_2-R^4-R^5]_2\}_2;$ $-(CH_2)_{p1}-[NR^2-(CH_2)_{q1}-]_{r1}NR^2-CH_2-CHOH-R^5;$ $-(CH_2)_{p2}-N[-(CH_2)_{q2}-NR^2-CH_2-CHOH-R^5]_2;$ $-(CH_2)_{p3}-N\{[-(CH_2)_{q3}-NR^2_2][-(CH_2)_{q4}-NR^2-]_{r2}-CH_2-CHOH-R^5\};$ $-(CH_2)_{p4}-N\{-(CH_2)_{q5}-N[-(CH_2)_{q6}-NR^2-CH_2-CHOH-R^5]_2\}_2;$ $-(CH_2)_{p1}-[NR^2-(CH_2)_{q1}-]_{r1}NR^2-(CH_2)_2-R^5;$ $-(CH_2)_{p2}-N[-(CH_2)_{q2}-NR^2-(CH_2)_2-R^5]_2;$ $-(CH_2)_{p3}-N\{[-(CH_2)_{q3}-NR^2_2][-(CH_2)_{q4}-NR^2-]12(CH_2)_2-R^5\};$ or $-(CH_2)_{p4}-N\{-(CH_2)_{q5}-N[-(CH_2)_{q6}-NR^2-(CH_2)_2-R^5]_2\}_2,$ wherein p1 to p4, q1 to q6, and r1 and r2 are each independently an integer of 1 to 5; each instance of $R^2$ is independently hydrogen or a $C_1$-$C_{12}$ alkyl group, alkenyl group, cycloalkyl group, or cycloalkenyl group; each instance of $R^4$ is independently —C(O)O—, —C(O)NH—, or —S(O)(O)—; and each instance of $R^5$ is independently an alkyl group, cycloalkyl group, alkenyl group, cycloalkenyl group, aryl group, heteroalkyl group, or heterocyclic group optionally comprising from 2 to 8 tertiary amines or a substituent comprising a tissue-specific or cell-specific targeting moiety.

7. A composition comprising the polymer of claim 1 and a nucleic acid and/or polypeptide.

8. A method of delivering a nucleic acid and/or polypeptide to a cell, the method comprising administering the composition of claim 7 to the cell.

9. A polymer comprising a structure of Formula 3:

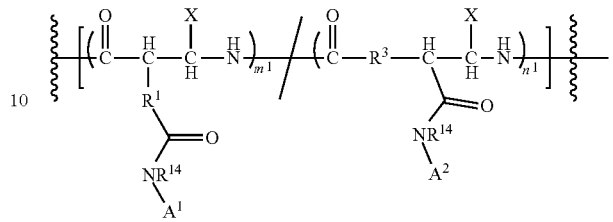

wherein,
each of $m^1$ and $n^1$ is an integer from 0 to 1000; provided that the sum of $m^1+n^1$ is greater than 5;
the symbol "/" indicates that the units separated thereby are linked randomly or in any order;
$R^1$ and $R^3$ each independently are a methylene or ethylene group;
each instance of $R^{14}$ is independently hydrogen or a $C_1$-$C_{12}$ alkyl group, alkenyl group, cycloalkyl group, or cycloalkenyl group;
each instance of X is independently a $C_1$-$C_{12}$ alkyl group, cycloalkyl group, alkenyl group, cycloalkenyl group, aryl group, heteroalkyl group, or heterocyclic group;
$A^1$ and $A^2$ are each independently a group of formula $-(CH_2)_{p1}-[NR^2-(CH_2)_{q1}-]_{r1}NR^2_2;$ $-(CH_2)_{p2}-N[-(CH_2)_{q2}-NR^2_2]_2;$ $-(CH_2)_{p3}-N\{[-(CH_2)_{q3}-NR^2_2][-(CH_2)_{q4}-NR^2-]_{r2}R^2\};$ or $-(CH_2)_{p4}-N\{-(CH_2)_{q5}-N[-(CH_2)_{q6}-NR^2_2]_2\}_2,$ wherein p1 to p4, q1 to q6, and r1 and r2 are each independently an integer of 1 to 5; and
each instance of $R^2$ is independently hydrogen or a $C_1$-$C_{12}$ alkyl group, alkenyl group, cycloalkyl group, or cycloalkenyl group.

10. The polymer of claim 9, having the structure of Formula 3A:

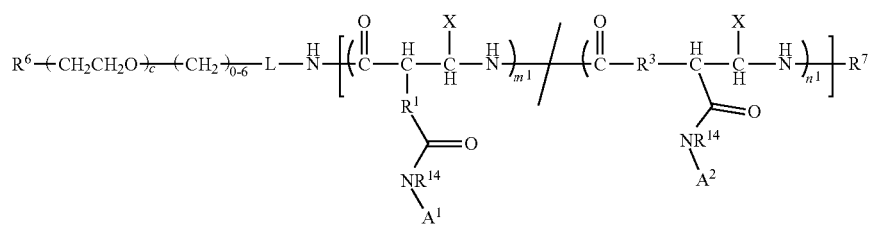

wherein,
c is an integer from 0 to 50;
L is optionally present and is a cleavable linker;
each of $m^1$ and $n^1$ is an integer from 0 to 1000; provided that the sum of $m^1+n^1$ is greater than 5;
the symbol "/" indicates that the units separated thereby are linked randomly or in any order;
$R^1$ and $R^3$ each independently are a methylene or ethylene group;
$R^6$ is hydrogen, an amino group, an aryl group, a heterocyclic group, a $C_1$-$C_{12}$ alkyl group, alkenyl group, cycloalkyl group, or cycloalkenyl group, a $C_1$-$C_{12}$ linear or branched alkyl group optionally substituted with one or more amines; or a tissue-specific or cell-specific targeting moiety;
$R^7$ is hydrogen, an aryl group, a heterocyclic group, a $C_1$-$C_{12}$ alkyl group, alkenyl group, cycloalkyl group, or cycloalkenyl group, or a $C_1$-$C_{12}$ linear or branched alkyl group optionally substituted with one or more substituents;
each instance of $R^{14}$ is independently hydrogen or a $C_1$-$C_{12}$ alkyl group, alkenyl group, cycloalkyl group, or cycloalkenyl group;
$A^1$ and $A^2$ are each independently a group of formula $-(CH_2)_{p1}-[NR^2-(CH_2)_{q1}-]_{r1}NR^2_2$;

$-(CH_2)_{p2}-N[-(CH_2)_{q2}-NR^2_2]_2$;

$-(CH_2)_{p3}-N\{[-(CH_2)_{q3}-NR^2_2][-(CH_2)_{q4}-NR^2-]_{r2}R^2\}$; or $-(CH_2)_{p4}-N\{-(CH_2)_{q5}-N[-(CH_2)_{q6}-NR^2_2]_2\}_2$, wherein p1 to p4, q1 to q6, and r1 and r2 are each independently an integer of 1 to 5; each instance of X is independently a $C_1$-$C_{12}$ alkyl group, cycloalkyl group, alkenyl group, cycloalkenyl group, aryl group, heteroalkyl group, or heterocyclic group; and each instance of $R^2$ is independently hydrogen or a $C_1$-$C_{12}$ alkyl group, alkenyl group, cycloalkyl group, or cycloalkenyl group.

11. The polymer of claim 9, comprising a structure of Formula 4:

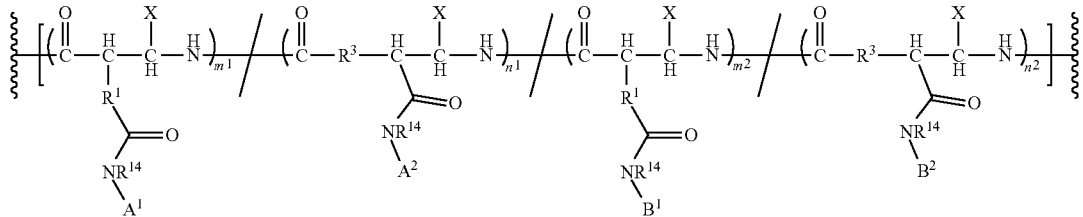

wherein,
each of $m^1$ and $n^1$ is an integer from 0 to 1000;
each of $m^2$ and $n^2$ is an integer from 0 to 1000, provided that the sum of $m^2+n^2$ is greater than 5;
the symbol "/" indicates that the units separated thereby are linked randomly or in any order;
each instance of $R^1$ and $R^3$ independently is a methylene or ethylene group;
each instance of $R^{14}$ is independently hydrogen or a $C_1$-$C_{12}$ alkyl group, alkenyl group, cycloalkyl group, or cycloalkenyl group;

each instance of X is independently a $C_1$-$C_{12}$ alkyl group, cycloalkyl group, alkenyl group, cycloalkenyl group, aryl group, heteroalkyl group, or heterocyclic group;
$A^1$ and $A^2$ are each independently a group of formula $-(CH_2)_{p1}-[NR^2-(CH_2)_{q1}-]_{r1}NR^2_2$;

$-(CH_2)_{p2}-N[-(CH_2)_{q2}-NR^2_2]_2$;

$-(CH_2)_{p3}-N\{[-(CH_2)_{q3}-NR^2_2][-(CH_2)_{q4}-NR^2-]_{r2}R^2\}$; or $-(CH_2)_{p4}-N\{-(CH_2)_{q5}-N[-(CH_2)_{q6}-NR^2_2]_2\}_2$, $B^1$ and $B^2$ are each independently $-(CH_2)_{p1}-[NR^2-(CH_2)_{q1}-]_{r1}NR^2-(CH_2)_2-R^4-R^5$;

$-(CH_2)_{p2}-N[-(CH_2)_{q2}-NR^2-(CH_2)_2-R^4-R^5]_2$;

$-(CH_2)_{p3}-N\{[-(CH_2)_{q3}-NR^2_2][-(CH_2)_{q4}-NR^2-]_{r2}(CH_2)_2-R^4-R^5\}$;

$-(CH_2)_{p4}-N\{-(CH_2)_{q5}-N[-(CH_2)_{q6}-NR^2-(CH_2)_2-R^4-R^5]_2\}_2$;

$-(CH_2)_{p1}-[NR^2-(CH_2)_{q1}-]_{r1}NR^2-CH_2-CHOH-R^5$;

$-(CH_2)_{p2}-N[-(CH_2)_{q2}-NR^2-CH_2-CHOH-R^5]_2$;

$-(CH_2)_{p3}-N\{[-(CH_2)_{q3}-NR^2_2][-(CH_2)_{q4}-NR^2-]_{r2}-CH_2-CHOH-R^5\}$;

$-(CH_2)_{p4}-N\{-(CH_2)_{q5}-N[-(CH_2)_{q6}-NR^2-CH_2-CHOH-R^5]_2\}_2$;

$-(CH_2)_{p1}-[NR^2-(CH_2)_{q1}-]_{r1}NR^2-(CH_2)_2-R^5$;

$-(CH_2)_{p2}-N[-(CH_2)_{q2}-NR^2-(CH_2)_2-R^5]_2$;

$-(CH_2)_{p3}-N\{[-(CH_2)_{q3}-NR^2_2][-(CH_2)_{q4}-NR^2-]_{r2}(CH_2)_2-R^5\}$; or $-(CH_2)_{p4}-N\{-(CH_2)_{q5}-N[-(CH_2)_{q6}-NR^2-(CH_2)_2-R^5]_2\}_2$, wherein p1 to p4, q1 to q6, and r1 and r2 are each independently an integer of 1 to 5;
each instance of $R^2$ is independently hydrogen or a $C_1$-$C_{12}$ alkyl group, alkenyl group, cycloalkyl group, or cycloalkenyl group; each instance of $R^4$ is independently —C(O)O—, —C(O)NH—, or —S(O)(O)—; and each instance of $R^5$ is independently an alkyl group, cycloalkyl group, alkenyl group, cycloalkenyl group, aryl group, heteroalkyl group, or heterocyclic group optionally comprising from 2 to 8 tertiary amines or a substituent comprising a tissue-specific or cell-specific targeting moiety.

12. The polymer of claim 11, having the structure of Formula 4A:

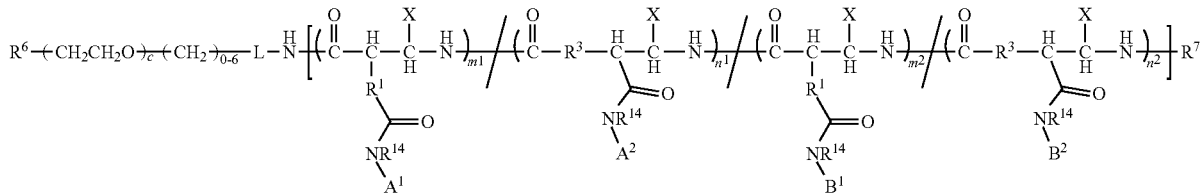

wherein,
c is an integer from 0 to 50;
L is optionally present and is a cleavable linker;
each of $m^1$ and $n^1$ is an integer from 0 to 1000;
each of $m^2$ and $n^2$ is an integer from 0 to 1000, provided that the sum of $m^2+n^2$ is greater than 5;
the symbol "/" indicates that the units separated thereby are linked randomly or in any order;
each instance of $R^1$ and $R^3$ independently is a methylene or ethylene group;
$R^6$ is hydrogen, an amino group, an aryl group, a heterocyclic group, a $C_1$-$C_{12}$ alkyl group, alkenyl group, cycloalkyl group, or cycloalkenyl group, a $C_1$-$C_{12}$ linear or branched alkyl group optionally substituted with one or more amines; or a tissue-specific or cell-specific targeting moiety;
$R^7$ is hydrogen, an aryl group, a heterocyclic group, a $C_1$-$C_{12}$ alkyl group, alkenyl group, cycloalkyl group, or cycloalkenyl group, or a $C_1$-$C_{12}$ linear or branched alkyl group optionally substituted with one or more substituents;
each instance of $R^{14}$ is independently hydrogen or a $C_1$-$C_{12}$ alkyl group, alkenyl group, cycloalkyl group, or cycloalkenyl group;
each instance of X is independently a $C_1$-$C_{12}$ alkyl group, cycloalkyl group, alkenyl group, cycloalkenyl group, aryl group, heteroalkyl group, or heterocyclic group;
$A^1$ and $A^2$ are each independently a group of formula —(CH$_2$)$_{p1}$—[NR$^2$—(CH$_2$)$_{q1}$—]$_{r1}$NR$^2_2$;

—(CH$_2$)$_{p2}$—N[—(CH$_2$)$_{q2}$—NR$^2_2$]$_2$;

—(CH$_2$)$_{p3}$—N{[—(CH$_2$)$_{q3}$—NR$^2_2$][—(CH$_2$)$_{q4}$—NR$^2$—]$_{r2}$R$^2$}; or

—(CH$_2$)$_{p4}$—N{—(CH$_2$)$_{q5}$—N[—(CH$_2$)$_{q6}$—NR$^2_2$]$_2$}$_2$, $B^1$ and $B^2$ are each independently —(CH$_2$)$_{p1}$—[NR$^2$—(CH$_2$)$_{q1}$—]$_{r1}$NR$^2$—(CH$_2$)$_2$—R$^4$—R$^5$;

—(CH$_2$)$_{p2}$—N[—(CH$_2$)$_{q2}$—NR$^2$—(CH$_2$)$_2$—R$^4$—R$^5$]$_2$;

—(CH$_2$)$_{p3}$—N{[—(CH$_2$)$_{q3}$—NR$^2_2$][—(CH$_2$)$_{q4}$—NR$^2$—]$_{r2}$(CH$_2$)$_2$—R$^4$—R$^5$};

—(CH$_2$)$_{p4}$—N{—(CH$_2$)$_{q5}$—N[—(CH$_2$)$_{q6}$—NR$^2$—(CH$_2$)$_2$—R$^4$—R$^5$]$_2$}$_2$;

—(CH$_2$)$_{p1}$—[NR$^2$—(CH$_2$)$_{q1}$—]$_{r1}$NR$^2$—CH$_2$—CHOH—R$^5$;

—(CH$_2$)$_{p2}$—N[—(CH$_2$)$_{q2}$—NR$^2$—CH$_2$—CHOH—R$^5$]$_2$;

—(CH$_2$)$_{p3}$—N{[—(CH$_2$)$_{q3}$—NR$^2_2$][—(CH$_2$)$_{q4}$—NR$^2$—]$_{r2}$—CH$_2$—CHOH—R$^5$};

—(CH$_2$)$_{p4}$—N{—(CH$_2$)$_{q5}$—N[—(CH$_2$)$_{q6}$—NR$^2$—CH$_2$—CHOH—R$^5$]$_2$}$_2$;

—(CH$_2$)$_{p1}$—[NR$^2$—(CH$_2$)$_{q1}$—]$_{r1}$NR$^2$—(CH$_2$)$_2$—R$^5$;

—(CH$_2$)$_{p2}$—N[—(CH$_2$)$_{q2}$—NR$^2$—(CH$_2$)$_2$—R$^5$]$_2$;

—(CH$_2$)$_{p3}$—N{[—(CH$_2$)$_{q3}$—NR$^2_2$][—(CH$_2$)$_{q4}$—NR$^2$—]12(CH$_2$)$_2$—R$^5$}; or

—(CH$_2$)$_{p4}$—N{—(CH$_2$)$_{q5}$—N[—(CH$_2$)$_{q6}$—NR$^2$—(CH$_2$)$_2$—R$^5$]$_2$}$_2$, wherein p1 to p4, q1 to q6, and r1 and r2 are each independently an integer of 1 to 5;

each instance of $R^2$ is independently hydrogen or a $C_1$-$C_{12}$ alkyl group, alkenyl group, cycloalkyl group, or cycloalkenyl group; each instance of $R^4$ is independently —C(O)O—, —C(O)NH—, or —S(O)(O)—; and each instance of $R^5$ is independently an alkyl group, cycloalkyl group, alkenyl group, cycloalkenyl group, aryl group, heteroalkyl group, or heterocyclic group optionally comprising from 2 to 8 tertiary amines or a substituent comprising a tissue-specific or cell-specific targeting moiety.

13. A method of preparing a polymer according to claim 11 comprising a structure of Formula 4:

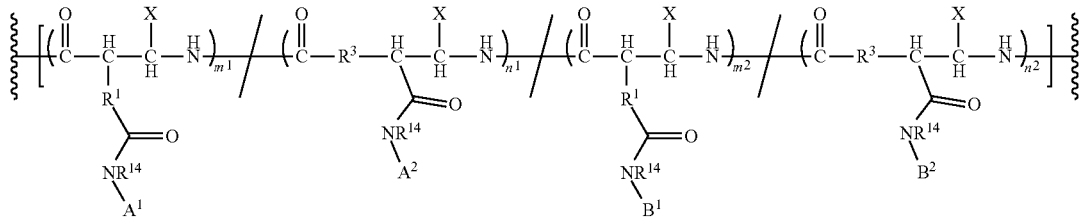

wherein,
each of $m^1$ and $n^1$ is an integer from 0 to 1000;
each of $m^2$ and $n^2$ is an integer from 0 to 1000, provided that the sum of $m^2+n^2$ is greater than 5;
the symbol "/" indicates that the units separated thereby are linked randomly or in any order;
each instance of $R^1$ and $R^3$ independently is a methylene or ethylene group;
each instance of $R^{14}$ is independently hydrogen or a $C_1$-$C_{12}$ alkyl group, alkenyl group, cycloalkyl group, or cycloalkenyl group;
each instance of X is independently a $C_1$-$C_{12}$ alkyl group, cycloalkyl group, alkenyl group, cycloalkenyl group, aryl group, heteroalkyl group, or heterocyclic group;
$A^1$ and $A^2$ are each independently a group of formula —$(CH_2)_{p1}$—$[NR^2$—$(CH_2)_{q1}$—$]_{r1}NR^2_2$;

—$(CH_2)_{p2}$—$N[$—$(CH_2)_{q2}$—$NR^2_2]_2$;

—$(CH_2)_{p3}$—$N\{[$—$(CH_2)_{q3}$—$NR^2_2][$—$(CH_2)_{q4}$—$NR^2$—$]_{r2}R^2\}$; or

—$(CH_2)_{p4}$—$N\{$—$(CH_2)_{q5}$—$N[$—$(CH_2)_{q6}$—$NR^2_2]_2\}_2$, $B^1$ and $B^2$ are each independently —$(CH_2)_{p1}$—$[NR^2$—$(CH_2)_{q1}$—$]_{r1}NR^2$—$(CH_2)_2$—$R^4$—$R^5$;

—$(CH_2)_{p2}$—$N[$—$(CH_2)_{q2}$—$NR^2$—$(CH_2)_2$—$R^4$—$R^5]_2$;

—$(CH_2)_{p3}$—$N\{[$—$(CH_2)_{q3}$—$NR^2_2][$—$(CH_2)_{q4}$—$NR^2$—$]_{r2}(CH_2)_2$—$R^4$—$R^5\}$;

—$(CH_2)_{p4}$—$N\{$—$(CH_2)_{q5}$—$N[$—$(CH_2)_{q6}$—$NR^2$—$(CH_2)_2$—$R^4$—$R^5]_2\}_2$;

—$(CH_2)_{p1}$—$[NR^2$—$(CH_2)_{q1}$—$]_{r1}NR^2$—$CH_2$—$CHOH$—$R^5$;

—$(CH_2)_{p2}$—$N[$—$(CH_2)_{q2}$—$NR^2$—$CH_2$—$CHOH$—$R^5]_2$;

—$(CH_2)_{p3}$—$N\{[$—$(CH_2)_{q3}$—$NR^2_2][$—$(CH_2)_{q4}$—$NR^2$—$]_{r2}$—$CH_2$—$CHOH$—$R^5\}$;

—$(CH_2)_{p4}$—$N\{$—$(CH_2)_{q5}$—$N[$—$(CH_2)_{q6}$—$NR^2$—$CH_2$—$CHOH$—$R^5]_2\}_2$;

—$(CH_2)_{p1}$—$[NR^2$—$(CH_2)_{q1}$—$]_{r1}NR^2$—$(CH_2)_2$—$R^5$;

—$(CH_2)_{p2}$—$N[$—$(CH_2)_{q2}$—$NR^2$—$(CH_2)_2$—$R^5]_2$;

—$(CH_2)_{p3}$—$N\{[$—$(CH_2)_{q3}$—$NR^2_2][$—$(CH_2)_{q4}$—$NR^2$—$]12(CH_2)_2$—$R^5\}$; or

—$(CH_2)_{p4}$—$N\{$—$(CH_2)_{q5}$—$N[$—$(CH_2)_{q6}$—$NR^2$—$(CH_2)_2$—$R^5]_2\}_2$, wherein p1 to p4, q1 to q6, and r1 and r2 are each independently an integer of 1 to 5;
each instance of $R^2$ is independently hydrogen or a $C_1$-$C_{12}$ alkyl group, alkenyl group, cycloalkyl group, or cycloalkenyl group; each instance of $R^4$ is independently —C(O)O—, —C(O)NH—, or —S(O)(O)—; and each instance of $R^5$ is independently an alkyl group, cycloalkyl group, alkenyl group, cycloalkenyl group, aryl group, heteroalkyl group, or heterocyclic group optionally comprising from 2 to 8 tertiary amines or a substituent comprising a tissue-specific or cell-specific targeting moiety from a polymer comprising a structure of Formula 3:

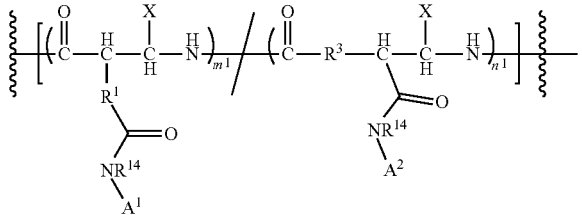

wherein,
each of $m^1$ and $n^1$ is an integer from 0 to 1000; provided that the sum of $m^1+n^1$ is greater than 5;
the symbol "/" indicates that the units separated thereby are linked randomly or in any order;
$R^1$ and $R^3$ each independently are a methylene or ethylene group;
each instance of $R^{14}$ is independently hydrogen or a $C_1$-$C_{12}$ alkyl group, alkenyl group, cycloalkyl group, or cycloalkenyl group;
$A^1$ and $A^2$ are each independently a group of formula —$(CH_2)_{p1}$—$[NR^2$—$(CH_2)_{q1}$—$]_{r1}NR^2_2$;

—$(CH_2)_{p2}$—$N[$—$(CH_2)_{q2}$—$NR^2_2]_2$;

—$(CH_2)_{p3}$—$N\{[$—$(CH_2)_{q3}$—$NR^2_2][$—$(CH_2)_{q4}$—$NR^2$—$]_{r2}R^2\}$; or

—$(CH_2)_{p4}$—$N\{$—$(CH_2)_{q5}$—$N[$—$(CH_2)_{q6}$—$NR^2_2]_2\}_2$, wherein p1 to p4, q1 to q6, and r1 and r2 are each independently an integer of 1 to 5; each instance of X is independently a $C_1$-$C_{12}$ alkyl group, cycloalkyl group, alkenyl group, cycloalkenyl group, aryl group, heteroalkyl group, or heterocyclic group; and each instance of $R^2$ is independently hydrogen or a $C_1$-$C_{12}$ alkyl group, alkenyl group, cycloalkyl group, or cycloalkenyl group, the method comprising modifying at least a portion of groups designated $A^1$ and/or $A^2$ to produce groups designated $B^1$ and/or $B^2$.

14. The method of claim 13, wherein the polymer comprising a structure of Formula 4 is a polymer of Formula 4A:

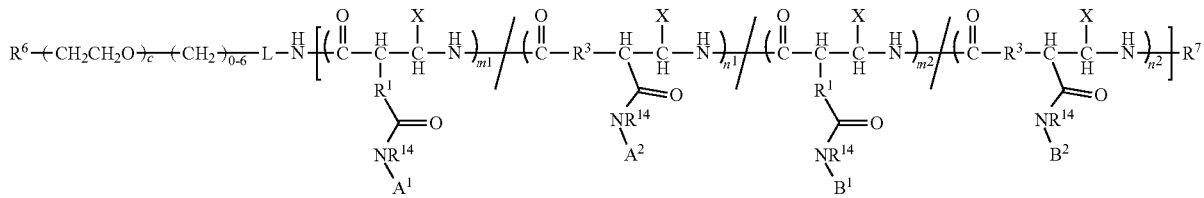

wherein, c is an integer from 0 to 50;

L is optionally present and is a cleavable linker;

each of $m^1$ and $n^1$ is an integer from 0 to 1000;

each of $m^2$ and $n^2$ is an integer from 0 to 1000, provided that the sum of $m^2+n^2$ is greater than 5;

the symbol "/" indicates that the units separated thereby are linked randomly or in any order;

each instance of $R^1$ and $R^3$ independently is a methylene or ethylene group;

$R^6$ is hydrogen, an amino group, an aryl group, a heterocyclic group, a $C_1$-$C_{12}$ alkyl group, alkenyl group, cycloalkyl group, or cycloalkenyl group, a $C_1$-$C_{12}$ linear or branched alkyl group optionally substituted with one or more amines; or a tissue-specific or cell-specific targeting moiety;

$R^7$ is hydrogen, an aryl group, a heterocyclic group, a $C_1$-$C_{12}$ alkyl group, alkenyl group, cycloalkyl group, or cycloalkenyl group, or a $C_1$-$C_{12}$ linear or branched alkyl group optionally substituted with one or more substituents;

each instance of $R^{14}$ is independently hydrogen or a $C_1$-$C_{12}$ alkyl group, alkenyl group, cycloalkyl group, or cycloalkenyl group;

each instance of X is independently a $C_1$-$C_{12}$ alkyl group, cycloalkyl group, alkenyl group, cycloalkenyl group, aryl group, heteroalkyl group, or heterocyclic group;

$A^1$ and $A^2$ are each independently a group of formula

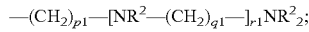

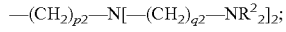

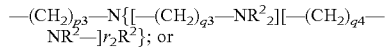

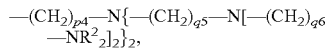

$B^1$ and $B^2$ are each independently

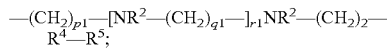

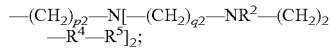

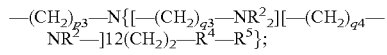

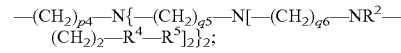

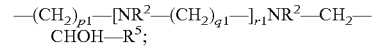

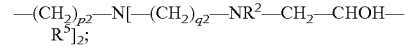

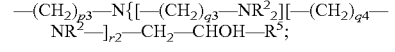

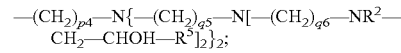

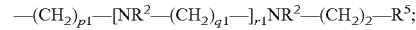

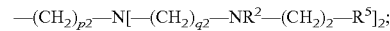

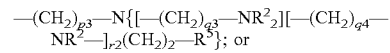

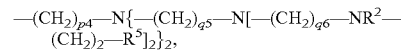

wherein p1 to p4, q1 to q6, and r1 and r2 are each independently an integer of 1 to 5;

each instance of $R^2$ is independently hydrogen or a $C_1$-$C_{12}$ alkyl group, alkenyl group, cycloalkyl group, or cycloalkenyl group; each instance of $R^4$ is independently —C(O)O—, —C(O)NH—, or —S(O)(O)—; and each instance of $R^5$ is independently an alkyl group, cycloalkyl group, alkenyl group, cycloalkenyl group, aryl group, heteroalkyl group, or heterocyclic group optionally comprising from 2 to 8 tertiary amines or a substituent comprising a tissue-specific or cell-specific targeting moiety.

15. A composition comprising the polymer of claim 9 and a nucleic acid and/or polypeptide.

16. A method of delivering a nucleic acid and/or polypeptide to a cell, the method comprising administering the composition of claim 15 to the cell.

17. A method of preparing a polymer according to claim 1 comprising a structure of Formula 1:

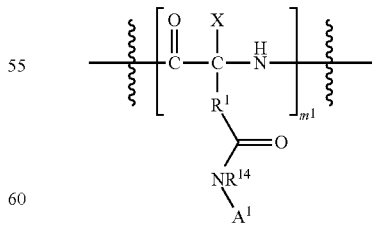

wherein, $m^1$ is an integer from 1 to 2000;

$R^1$ is a methylene or ethylene group;

$R^{14}$ is hydrogen or a $C_1$-$C_{12}$ alkyl group, alkenyl group, cycloalkyl group, or cycloalkenyl group;

X is a $C_1$-$C_{12}$ alkyl group, cycloalkyl group, alkenyl group, cycloalkenyl group, aryl group, heteroalkyl group, or heterocyclic group;

$A^1$ is a group of formula

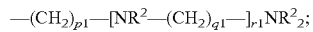

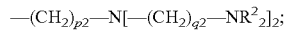

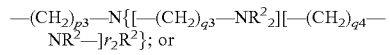

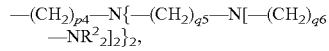

wherein p1 to p4, q1 to q6, and r1 and r2 are each independently an integer of 1 to 5; and each instance of $R^2$ is independently hydrogen or a $C_1$-$C_{12}$ alkyl group, alkenyl group, cycloalkyl group, or cycloalkenyl group, from a compound of Formula A:

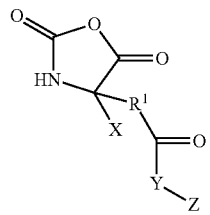

wherein, $R^1$ is a methylene or ethylene group;

X is a $C_1$-$C_{12}$ alkyl group, cycloalkyl group, alkenyl group, cycloalkenyl group, aryl group, heteroalkyl group, or heterocyclic group;

Y is —$NR^{14}$— or —O—, wherein $R^{14}$ is hydrogen or a $C_1$-$C_{12}$ alkyl group, alkenyl group, cycloalkyl group, or cycloalkenyl group;

Z is $A^1$, or an alkyl group, cycloalkyl group, alkenyl group, cycloalkenyl group, aryl group, arylalkyl group, heteroalkyl group, or heterocyclic group optionally comprising from 2 to 8 tertiary amines or a substituent comprising a tissue-specific or cell-specific targeting moiety;

$A^1$ is a group of formula

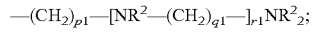

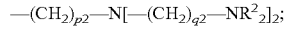

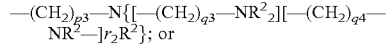

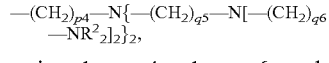

wherein p1 to p4, q1 to q6, and r1 and r2 are each independently an integer of 1 to 5; and each instance of $R^2$ is independently hydrogen or a $C_1$-$C_{12}$ alkyl group, alkenyl group, cycloalkyl group, or cycloalkenyl group, the method comprising a ring-opening polymerization of the compound Formula A.

18. The method of claim 17, wherein the polymer comprising a structure of Formula 1 is a polymer of Formula 1A:

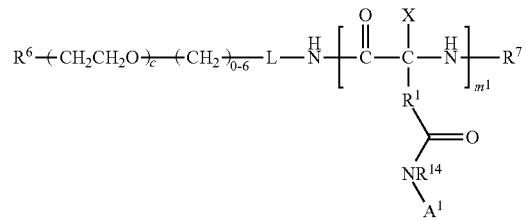

wherein, c is an integer from 0 to 50;

L is optionally present and is a cleavable linker;

$m^1$ is an integer from 1 to 2000;

$R^1$ is a methylene or ethylene group;

$R^6$ is hydrogen, an amino group, an aryl group, a heterocyclic group, a $C_1$-$C_{12}$ alkyl group, alkenyl group, cycloalkyl group, or cycloalkenyl group, a $C_1$-$C_{12}$ linear or branched alkyl group optionally substituted with one or more amines; or a tissue-specific or cell-specific targeting moiety;

$R^7$ is hydrogen, an aryl group, a heterocyclic group, a $C_1$-$C_{12}$ alkyl group, alkenyl group, cycloalkyl group, or cycloalkenyl group, or a $C_1$-$C_{12}$ linear or branched alkyl group optionally substituted with one or more substituents;

$R^{14}$ is hydrogen or a $C_1$-$C_{12}$ alkyl group, alkenyl group, cycloalkyl group, or cycloalkenyl group;

X is a $C_1$-$C_{12}$ alkyl group, cycloalkyl group, alkenyl group, cycloalkenyl group, aryl group, heteroalkyl group, or heterocyclic group;

$A^1$ is a group of formula

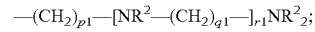

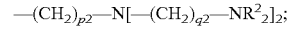

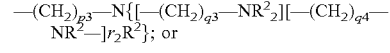

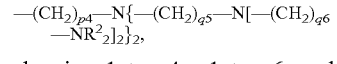

wherein p1 to p4, q1 to q6, and r1 and r2 are each independently an integer of 1 to 5; and each instance of $R^2$ is independently hydrogen or a $C_1$-$C_{12}$ alkyl group, alkenyl group, cycloalkyl group, or cycloalkenyl group.

19. A method of preparing a polymer according to claim 9 comprising a structure of Formula 3:

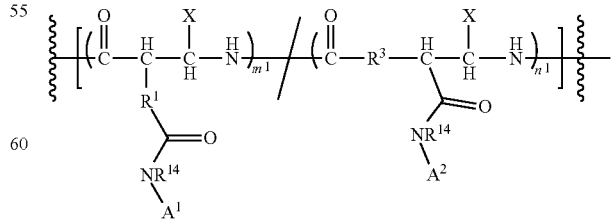

wherein, each of $m^1$ and $n^1$ is an integer from 0 to 1000; provided that the sum of $m^1$+$n^1$ is greater than 5;

the symbol "/" indicates that the units separated thereby are linked randomly or in any order;

$R^1$ and $R^3$ each independently are a methylene or ethylene group;

each instance of $R^{14}$ is independently hydrogen or a $C_1$-$C_{12}$ alkyl group, alkenyl group, cycloalkyl group, or cycloalkenyl group;

each instance of X is independently a $C_1$-$C_{12}$ alkyl group, cycloalkyl group, alkenyl group, cycloalkenyl group, aryl group, heteroalkyl group, or heterocyclic group;

$A^1$ and $A^2$ are each independently a group of formula

—$(CH_2)_{p1}$—[$NR^2$—$(CH_2)_{q1}$—]$_{r1}NR^2{}_2$;

—$(CH_2)_{p2}$—N[—$(CH_2)_{q2}$—$NR^2{}_2$]$_2$;

—$(CH_2)_{p3}$—N{[—$(CH_2)_{q3}$—$NR^2{}_2$][—$(CH_2)_{q4}$—$NR^2$—]$_{r2}R^2$}; or

—$(CH_2)_{p4}$—N{—$(CH_2)_{q5}$—N[—$(CH_2)_{q6}$—$NR^2{}_2$]$_2$}$_2$, wherein p1 to p4, q1 to q6, and r1 and r2 are each independently an integer of 1 to 5; and each instance of $R^2$ is independently hydrogen or a $C_1$-$C_{12}$ alkyl group, alkenyl group, cycloalkyl group, or cycloalkenyl group, from a compound of Formula B:

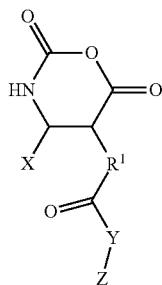

wherein, $R^1$ is a methylene or ethylene group;

X is a $C_1$-$C_{12}$ alkyl group, cycloalkyl group, alkenyl group, cycloalkenyl group, aryl group, heteroalkyl group, or heterocyclic group;

Y is —$NR^{14}$— or —O—, wherein $R^{14}$ is hydrogen or a $C_1$-$C_{12}$ alkyl group, alkenyl group, cycloalkyl group, or cycloalkenyl group;

Z is $A^1$, or an alkyl group, cycloalkyl group, alkenyl group, cycloalkenyl group, aryl group, arylalkyl group, heteroalkyl group, or heterocyclic group optionally comprising from 2 to 8 tertiary amines or a substituent comprising a tissue-specific or cell-specific targeting moiety;

$A^1$ is a group of formula

—$(CH_2)_{p1}$—[$NR^2$—$(CH_2)_{q1}$—]$_{r1}NR^2{}_2$;

—$(CH_2)_{p2}$—N[—$(CH_2)_{q2}$—$NR^2{}_2$]$_2$;

—$(CH_2)_{p3}$—N{[—$(CH_2)_{q3}$—$NR^2{}_2$][—$(CH_2)_{q4}$—$NR^2$—]$_{r2}R^2$}; or

—$(CH_2)_{p4}$—N{—$(CH_2)_{q5}$—N[—$(CH_2)_{q6}$—$NR^2{}_2$]$_2$}$_2$, wherein p1 to p4, q1 to q6, and r1 and r2 are each independently an integer of 1 to 5; and each instance of $R^2$ is independently hydrogen or a $C_1$-$C_{12}$ alkyl group, alkenyl group, cycloalkyl group, or cycloalkenyl group, the method comprising a ring-opening polymerization of the compound formula B.

20. The method of claim 19, wherein the polymer comprising a structure of Formula 3 is a polymer of Formula 3A:

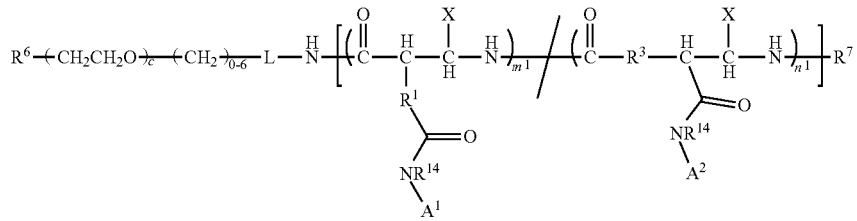

wherein, c is an integer from 0 to 50;

L is optionally present and is a cleavable linker;

each of $m^1$ and $n^1$ is an integer from 0 to 1000; provided that the sum of $m^1$+$n^1$ is greater than 5;

the symbol "/" indicates that the units separated thereby are linked randomly or in any order;

$R^1$ and $R^3$ each independently are a methylene or ethylene group;

$R^6$ is hydrogen, an amino group, an aryl group, a heterocyclic group, a $C_1$-$C_{12}$ alkyl group, alkenyl group, cycloalkyl group, or cycloalkenyl group, a $C_1$-$C_{12}$ linear or branched alkyl group optionally substituted with one or more amines; or a tissue-specific or cell-specific targeting moiety;

$R^7$ is hydrogen, an aryl group, a heterocyclic group, a $C_1$-$C_{12}$ alkyl group, alkenyl group, cycloalkyl group, or cycloalkenyl group, or a $C_1$-$C_{12}$ linear or branched alkyl group optionally substituted with one or more substituents;

each instance of $R^{14}$ is independently hydrogen or a $C_1$-$C_{12}$ alkyl group, alkenyl group, cycloalkyl group, or cycloalkenyl group;

$A^1$ and $A^2$ are each independently a group of formula

—$(CH_2)_{p1}$—[$NR^2$—$(CH_2)_{q1}$—]$_{r1}NR^2{}_2$;

—$(CH_2)_{p2}$—N[—$(CH_2)_{q2}$—$NR^2{}_2$]$_2$;

—$(CH_2)_{p3}$—N{[—$(CH_2)_{q3}$—$NR^2{}_2$][—$(CH_2)_{q4}$—$NR^2$—]$_{r2}R^2$}; or

—$(CH_2)_{p4}$—N{—$(CH_2)_{q5}$—N[—$(CH_2)_{q6}$—$NR^2{}_2$]$_2$}$_2$, wherein p1 to p4, q1 to q6, and r1 and r2 are each independently an integer of 1 to 5;

each instance of X is independently a $C_1$-$C_{12}$ alkyl group, cycloalkyl group, alkenyl group, cycloalkenyl group, aryl group, heteroalkyl group, or heterocyclic group, or cycloalkenyl group; and each instance of $R^2$ is independently hydrogen or a $C_1$-$C_{12}$ alkyl group, alkenyl group, cycloalkyl group, or cycloalkenyl group.

* * * * *

SEQUENCE LISTING

```
<160> NUMBER OF SEQ ID NOS: 20

<210> SEQ ID NO 1
<211> LENGTH: 1368
<212> TYPE: PRT
<213> ORGANISM: Streptococcus pyogenes
<220> FEATURE:
<221> NAME/KEY: MISC_FEATURE
<222> LOCATION: (1)..(1368)
<223> OTHER INFORMATION: AKP81606.1

<400> SEQUENCE: 1

Met Asp Lys Lys Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Phe
            20                  25                  30

Lys Val Leu Gly Asn Thr Asp Arg His Ser Ile Lys Lys Asn Leu Ile
```

-continued

```
                35                  40                  45
Gly Ala Leu Leu Phe Asp Ser Gly Glu Thr Ala Glu Ala Thr Arg Leu
 50                  55                  60
Lys Arg Thr Ala Arg Arg Tyr Thr Arg Arg Lys Asn Arg Ile Cys
 65                  70                  75                  80
Tyr Leu Gln Glu Ile Phe Ser Asn Glu Met Ala Lys Val Asp Asp Ser
                     85                  90                  95
Phe Phe His Arg Leu Glu Glu Ser Phe Leu Val Glu Glu Asp Lys Lys
                    100                 105                 110
His Glu Arg His Pro Ile Phe Gly Asn Ile Val Asp Glu Val Ala Tyr
                    115                 120                 125
His Glu Lys Tyr Pro Thr Ile Tyr His Leu Arg Lys Lys Leu Val Asp
                    130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                    165                 170                 175
Asp Asn Ser Asp Val Asp Lys Leu Phe Ile Gln Leu Val Gln Thr Tyr
                    180                 185                 190
Asn Gln Leu Phe Glu Glu Asn Pro Ile Asn Ala Ser Gly Val Asp Ala
                    195                 200                 205
Lys Ala Ile Leu Ser Ala Arg Leu Ser Lys Ser Arg Arg Leu Glu Asn
210                 215                 220
Leu Ile Ala Gln Leu Pro Gly Glu Lys Lys Asn Ser Leu Phe Gly Asn
225                 230                 235                 240
Leu Ile Ala Leu Ser Leu Gly Leu Thr Pro Asn Phe Lys Ser Asn Phe
                    245                 250                 255
Asp Leu Ala Glu Asp Ala Lys Leu Gln Leu Ser Lys Asp Thr Tyr Asp
                    260                 265                 270
Asp Asp Leu Asp Asn Leu Leu Ala Gln Ile Gly Asp Gln Tyr Ala Asp
                    275                 280                 285
Leu Phe Leu Ala Ala Lys Asn Leu Ser Asp Ala Ile Leu Leu Ser Asp
                    290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                    325                 330                 335
Ala Leu Val Arg Gln Gln Leu Pro Glu Lys Tyr Lys Glu Ile Phe Phe
                    340                 345                 350
Asp Gln Ser Lys Asn Gly Tyr Ala Gly Tyr Ile Asp Gly Gly Ala Ser
                    355                 360                 365
Gln Glu Glu Phe Tyr Lys Phe Ile Lys Pro Ile Leu Glu Lys Met Asp
                    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                    405                 410                 415
Gly Glu Leu His Ala Ile Leu Arg Arg Gln Glu Asp Phe Tyr Pro Phe
                    420                 425                 430
Leu Lys Asp Asn Arg Glu Lys Ile Glu Lys Ile Leu Thr Phe Arg Ile
                    435                 440                 445
Pro Tyr Tyr Val Gly Pro Leu Ala Arg Gly Asn Ser Arg Phe Ala Trp
450                 455                 460
```

```
Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
                530             535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
                690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
                770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
                835                 840                 845

Asp Asp Ser Ile Asp Asn Lys Val Leu Thr Arg Ser Asp Lys Asn Arg
                850                 855                 860

Gly Lys Ser Asp Asn Val Pro Ser Glu Glu Val Val Lys Lys Met Lys
865                 870                 875                 880
```

```
Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
        900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
```

```
                  1280            1285            1290
Tyr Asn Lys His Arg Asp Lys Pro Ile Arg Glu Gln Ala Glu Asn
            1295            1300            1305
Ile Ile His Leu Phe Thr Leu Thr Asn Leu Gly Ala Pro Ala Ala
            1310            1315            1320
Phe Lys Tyr Phe Asp Thr Thr Ile Asp Arg Lys Arg Tyr Thr Ser
            1325            1330            1335
Thr Lys Glu Val Leu Asp Ala Thr Leu Ile His Gln Ser Ile Thr
            1340            1345            1350
Gly Leu Tyr Glu Thr Arg Ile Asp Leu Ser Gln Leu Gly Gly Asp
            1355            1360            1365

<210> SEQ ID NO 2
<211> LENGTH: 1300
<212> TYPE: PRT
<213> ORGANISM: Francisella tularensis

<400> SEQUENCE: 2

Met Ser Ile Tyr Gln Glu Phe Val Asn Lys Tyr Ser Leu Ser Lys Thr
1               5                   10                  15
Leu Arg Phe Glu Leu Ile Pro Gln Gly Lys Thr Leu Glu Asn Ile Lys
            20                  25                  30
Ala Arg Gly Leu Ile Leu Asp Asp Glu Lys Arg Ala Lys Asp Tyr Lys
        35                  40                  45
Lys Ala Lys Gln Ile Ile Asp Lys Tyr His Gln Phe Phe Ile Glu Glu
    50                  55                  60
Ile Leu Ser Ser Val Cys Ile Ser Glu Asp Leu Leu Gln Asn Tyr Ser
65                  70                  75                  80
Asp Val Tyr Phe Lys Leu Lys Lys Ser Asp Asp Asp Asn Leu Gln Lys
                85                  90                  95
Asp Phe Lys Ser Ala Lys Asp Thr Ile Lys Lys Gln Ile Ser Glu Tyr
            100                 105                 110
Ile Lys Asp Ser Glu Lys Phe Lys Asn Leu Phe Asn Gln Asn Leu Ile
        115                 120                 125
Asp Ala Lys Lys Gly Gln Glu Ser Asp Leu Ile Leu Trp Leu Lys Gln
    130                 135                 140
Ser Lys Asp Asn Gly Ile Glu Leu Phe Lys Ala Asn Ser Asp Ile Thr
145                 150                 155                 160
Asp Ile Asp Glu Ala Leu Glu Ile Ile Lys Ser Phe Lys Gly Trp Thr
                165                 170                 175
Thr Tyr Phe Lys Gly Phe His Glu Asn Arg Lys Asn Val Tyr Ser Ser
            180                 185                 190
Asn Asp Ile Pro Thr Ser Ile Ile Tyr Arg Ile Val Asp Asp Asn Leu
        195                 200                 205
Pro Lys Phe Leu Glu Asn Lys Ala Lys Tyr Glu Ser Leu Lys Asp Lys
    210                 215                 220
Ala Pro Glu Ala Ile Asn Tyr Glu Gln Ile Lys Lys Asp Leu Ala Glu
225                 230                 235                 240
Glu Leu Thr Phe Asp Ile Asp Tyr Lys Thr Ser Glu Val Asn Gln Arg
                245                 250                 255
Val Phe Ser Leu Asp Glu Val Phe Glu Ile Ala Asn Phe Asn Asn Tyr
            260                 265                 270
Leu Asn Gln Ser Gly Ile Thr Lys Phe Asn Thr Ile Ile Gly Gly Lys
        275                 280                 285
```

```
Phe Val Asn Gly Glu Asn Thr Lys Arg Lys Gly Ile Asn Glu Tyr Ile
290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
                340                 345                 350

Gln Ser Phe Tyr Glu Gln Ile Ala Ala Phe Lys Thr Val Glu Glu Lys
            355                 360                 365

Ser Ile Lys Glu Thr Leu Ser Leu Leu Phe Asp Asp Leu Lys Ala Gln
370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Thr Glu Lys Ala
                435                 440                 445

Lys Tyr Leu Ser Leu Glu Thr Ile Lys Leu Ala Leu Glu Glu Phe Asn
450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
                500                 505                 510

Asp Leu Leu Gln Ala Ser Ala Glu Asp Val Lys Ala Ile Lys Asp
                515                 520                 525

Leu Leu Asp Gln Thr Asn Asn Leu Leu His Lys Leu Lys Ile Phe His
530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
                580                 585                 590

Asp Glu Lys Phe Lys Leu Asn Phe Glu Asn Ser Thr Leu Ala Asn Gly
            595                 600                 605

Trp Asp Lys Asn Lys Glu Pro Asp Asn Thr Ala Ile Leu Phe Ile Lys
610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
            675                 680                 685

Leu Arg Ile Arg Asn His Ser Thr His Thr Lys Asn Gly Ser Pro Gln
690                 695                 700

Lys Gly Tyr Glu Lys Phe Glu Phe Asn Ile Glu Asp Cys Arg Lys Phe
```

```
       705                 710                 715                 720
Ile Asp Phe Tyr Lys Gln Ser Ile Ser Lys His Pro Glu Trp Lys Asp
                    725                 730                 735

Phe Gly Phe Arg Phe Ser Asp Thr Gln Arg Tyr Asn Ser Ile Asp Glu
                740                 745                 750

Phe Tyr Arg Glu Val Glu Asn Gln Gly Tyr Lys Leu Thr Phe Glu Asn
                755                 760                 765

Ile Ser Glu Ser Tyr Ile Asp Ser Val Val Asn Gln Gly Lys Leu Tyr
                770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                    805                 810                 815

Leu Gln Asp Val Val Tyr Lys Leu Asn Gly Glu Ala Glu Leu Phe Tyr
                820                 825                 830

Arg Lys Gln Ser Ile Pro Lys Lys Ile Thr His Pro Ala Lys Glu Ala
                835                 840                 845

Ile Ala Asn Lys Asn Lys Asp Asn Pro Lys Lys Glu Ser Val Phe Glu
850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                    885                 890                 895

Asn Asp Glu Ile Asn Leu Leu Leu Lys Glu Lys Ala Asn Asp Val His
                900                 905                 910

Ile Leu Ser Ile Asp Arg Gly Glu Arg His Leu Ala Tyr Tyr Thr Leu
                915                 920                 925

Val Asp Gly Lys Gly Asn Ile Ile Lys Gln Asp Thr Phe Asn Ile Ile
                930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                    965                 970                 975

Ile Lys Glu Met Lys Glu Gly Tyr Leu Ser Gln Val Val His Glu Ile
                980                 985                 990

Ala Lys Leu Val Ile Glu Tyr Asn Ala Ile Val Val Phe Glu Asp Leu
                995                1000                1005

Asn Phe Gly Phe Lys Arg Gly Arg Phe Lys Val Glu Lys Gln Val
   1010                1015                1020

Tyr Gln Lys Leu Glu Lys Met Leu Ile Glu Lys Leu Asn Tyr Leu
   1025                1030                1035

Val Phe Lys Asp Asn Glu Phe Asp Lys Thr Gly Gly Val Leu Arg
   1040                1045                1050

Ala Tyr Gln Leu Thr Ala Pro Phe Glu Thr Phe Lys Lys Met Gly
   1055                1060                1065

Lys Gln Thr Gly Ile Ile Tyr Tyr Val Pro Ala Gly Phe Thr Ser
   1070                1075                1080

Lys Ile Cys Pro Val Thr Gly Phe Val Asn Gln Leu Tyr Pro Lys
   1085                1090                1095

Tyr Glu Ser Val Ser Lys Ser Gln Glu Phe Phe Ser Lys Phe Asp
   1100                1105                1110

Lys Ile Cys Tyr Asn Leu Asp Lys Gly Tyr Phe Glu Phe Ser Phe
   1115                1120                1125
```

Asp Tyr Lys Asn Phe Gly Asp Lys Ala Ala Lys Gly Lys Trp Thr
        1130            1135                1140

Ile Ala Ser Phe Gly Ser Arg Leu Ile Asn Phe Arg Asn Ser Asp
        1145            1150                1155

Lys Asn His Asn Trp Asp Thr Arg Glu Val Tyr Pro Thr Lys Glu
        1160            1165                1170

Leu Glu Lys Leu Leu Lys Asp Tyr Ser Ile Glu Tyr Gly His Gly
        1175            1180                1185

Glu Cys Ile Lys Ala Ala Ile Cys Gly Glu Ser Asp Lys Lys Phe
        1190            1195                1200

Phe Ala Lys Leu Thr Ser Val Leu Asn Thr Ile Leu Gln Met Arg
        1205            1210                1215

Asn Ser Lys Thr Gly Thr Glu Leu Asp Tyr Leu Ile Ser Pro Val
        1220            1225                1230

Ala Asp Val Asn Gly Asn Phe Phe Asp Ser Arg Gln Ala Pro Lys
        1235            1240                1245

Asn Met Pro Gln Asp Ala Asp Ala Asn Gly Ala Tyr His Ile Gly
        1250            1255                1260

Leu Lys Gly Leu Met Leu Leu Gly Arg Ile Lys Asn Asn Gln Glu
        1265            1270                1275

Gly Lys Lys Leu Asn Leu Val Ile Lys Asn Glu Glu Tyr Phe Glu
        1280            1285                1290

Phe Val Gln Asn Arg Asn Asn
        1295            1300

<210> SEQ ID NO 3
<211> LENGTH: 15
<212> TYPE: PRT
<213> ORGANISM: Artificial Sequence
<220> FEATURE:
<223> OTHER INFORMATION: Synthetic

<400> SEQUENCE: 3

Ile Gly Leu Asp Ile Gly Thr Asn Ser Val Gly Trp Ala Val Ile
1               5                   10                  15

<210> SEQ ID NO 4
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 4

Ile Val Ile Glu Met Ala Arg Glu
1               5

<210> SEQ ID NO 5
<211> LENGTH: 27
<212> TYPE: PRT
<213> ORGANISM: Artificial Sequence
<220> FEATURE:
<223> OTHER INFORMATION: Synthetic Sequence

<400> SEQUENCE: 5

Asp Val Asp His Ile Val Pro Gln Ser Phe Leu Lys Asp Asp Ser Ile
1               5                   10                  15

Asp Asn Lys Val Leu Thr Arg Ser Asp Lys Asn
            20                  25

```
<210> SEQ ID NO 6
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 6

His His Ala His Asp Ala Tyr Leu
1               5

<210> SEQ ID NO 7
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 7

Tyr Gly Arg Lys Lys Arg Arg Gln Arg Arg Arg
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 8

Arg Arg Gln Arg Arg Thr Ser Lys Leu Met Lys Arg
1               5                   10

<210> SEQ ID NO 9
<211> LENGTH: 27
<212> TYPE: PRT
<213> ORGANISM: Artificial Sequence
<220> FEATURE:
<223> OTHER INFORMATION: Synthetic Sequence

<400> SEQUENCE: 9

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 10
<211> LENGTH: 33
<212> TYPE: PRT
<213> ORGANISM: Artificial Sequence
<220> FEATURE:
<223> OTHER INFORMATION: Synthetic Sequence

<400> SEQUENCE: 10

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 11
<211> LENGTH: 16
<212> TYPE: PRT
<213> ORGANISM: Artificial Sequence
<220> FEATURE:
```

```
<223> OTHER INFORMATION: Synthetic Sequence

<400> SEQUENCE: 11

Arg Gln Ile Lys Ile Trp Phe Gln Asn Arg Arg Met Lys Trp Lys Lys
1               5                   10                  15

<210> SEQ ID NO 12
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 12

Tyr Gly Arg Lys Lys Arg Arg Gln Arg Arg Arg
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 13

Arg Lys Lys Arg Arg Gln Arg Arg Arg
1               5

<210> SEQ ID NO 14
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 14

Tyr Gly Arg Lys Lys Arg Arg Gln Arg Arg
1               5                   10

<210> SEQ ID NO 15
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 15

Arg Lys Lys Arg Arg Gln Arg Arg
1               5

<210> SEQ ID NO 16
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 16

Tyr Ala Arg Ala Ala Ala Arg Gln Ala Arg Ala
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic Sequence
```

<400> SEQUENCE: 17

Thr His Arg Leu Pro Arg Arg Arg Arg Arg
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 18

Gly Gly Arg Arg Ala Arg Arg Arg Arg Arg
1               5                   10

<210> SEQ ID NO 19
<211> LENGTH: 1307
<212> TYPE: PRT
<213> ORGANISM: Artificial Sequence
<220> FEATURE:
<223> OTHER INFORMATION: Synthetic Sequence

<400> SEQUENCE: 19

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

```
Lys Ile Lys Gly Leu Asn Glu Val Leu Asn Leu Ala Ile Gln Lys Asn
            275                 280                 285

Asp Glu Thr Ala His Ile Ile Ala Ser Leu Pro His Arg Phe Ile Pro
            290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
            355                 360                 365

Lys Lys Leu Glu Thr Ile Ser Ser Ala Leu Cys Asp His Trp Asp Thr
            370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
            435                 440                 445

Ala Leu Asp Gln Pro Leu Pro Thr Thr Leu Lys Lys Gln Glu Glu Lys
            450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
            515                 520                 525

Glu Lys Phe Lys Leu Asn Phe Gln Met Pro Thr Leu Ala Ser Gly Trp
            530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
            595                 600                 605

Ser Thr Gln Leu Lys Ala Val Thr Ala His Phe Gln Thr His Thr Thr
            610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
                660                 665                 670

Leu Cys Lys Trp Ile Asp Phe Thr Arg Asp Phe Leu Ser Lys Tyr Thr
            675                 680                 685
```

-continued

Lys Thr Thr Ser Ile Asp Leu Ser Ser Leu Arg Pro Ser Ser Gln Tyr
    690             695             700

Lys Asp Leu Gly Glu Tyr Tyr Ala Glu Leu Asn Pro Leu Leu Tyr His
705             710             715             720

Ile Ser Phe Gln Arg Ile Ala Glu Lys Glu Ile Met Asp Ala Val Glu
        725             730             735

Thr Gly Lys Leu Tyr Leu Phe Gln Ile Tyr Asn Lys Asp Phe Ala Lys
            740             745             750

Gly His His Gly Lys Pro Asn Leu His Thr Leu Tyr Trp Thr Gly Leu
        755             760             765

Phe Ser Pro Glu Asn Leu Ala Lys Thr Ser Ile Lys Leu Asn Gly Gln
770             775             780

Ala Glu Leu Phe Tyr Arg Pro Lys Ser Arg Met Lys Arg Met Ala His
785             790             795             800

Arg Leu Gly Glu Lys Met Leu Asn Lys Lys Leu Lys Asp Gln Lys Thr
            805             810             815

Pro Ile Pro Asp Thr Leu Tyr Gln Glu Leu Tyr Asp Tyr Val Asn His
        820             825             830

Arg Leu Ser His Asp Leu Ser Asp Glu Ala Arg Ala Leu Leu Pro Asn
        835             840             845

Val Ile Thr Lys Glu Val Ser His Glu Ile Ile Lys Asp Arg Arg Phe
850             855             860

Thr Ser Asp Lys Phe Phe Phe His Val Pro Ile Thr Leu Asn Tyr Gln
865             870             875             880

Ala Ala Asn Ser Pro Ser Lys Phe Asn Gln Arg Val Asn Ala Tyr Leu
            885             890             895

Lys Glu His Pro Glu Thr Pro Ile Ile Gly Ile Asp Arg Gly Glu Arg
            900             905             910

Asn Leu Ile Tyr Ile Thr Val Ile Asp Ser Thr Gly Lys Ile Leu Glu
        915             920             925

Gln Arg Ser Leu Asn Thr Ile Gln Gln Phe Asp Tyr Gln Lys Lys Leu
    930             935             940

Asp Asn Arg Glu Lys Glu Arg Val Ala Ala Arg Gln Ala Trp Ser Val
945             950             955             960

Val Gly Thr Ile Lys Asp Leu Lys Gln Gly Tyr Leu Ser Gln Val Ile
            965             970             975

His Glu Ile Val Asp Leu Met Ile His Tyr Gln Ala Val Val Val Leu
        980             985             990

Glu Asn Leu Asn Phe Gly Phe Lys Ser Lys Arg Thr Gly Ile Ala Glu
        995             1000            1005

Lys Ala Val Tyr Gln Gln Phe Glu Lys Met Leu Ile Asp Lys Leu
    1010            1015            1020

Asn Cys Leu Val Leu Lys Asp Tyr Pro Ala Glu Lys Val Gly Gly
    1025            1030            1035

Val Leu Asn Pro Tyr Gln Leu Thr Asp Gln Phe Thr Ser Phe Ala
    1040            1045            1050

Lys Met Gly Thr Gln Ser Gly Phe Leu Phe Tyr Val Pro Ala Pro
    1055            1060            1065

Tyr Thr Ser Lys Ile Asp Pro Leu Thr Gly Phe Val Asp Pro Phe
    1070            1075            1080

Val Trp Lys Thr Ile Lys Asn His Glu Ser Arg Lys His Phe Leu
    1085            1090            1095

Glu Gly Phe Asp Phe Leu His Tyr Asp Val Lys Thr Gly Asp Phe

```
                1100                1105                1110
Ile Leu His Phe Lys Met Asn Arg Asn Leu Ser Phe Gln Arg Gly
    1115                1120                1125
Leu Pro Gly Phe Met Pro Ala Trp Asp Ile Val Phe Glu Lys Asn
    1130                1135                1140
Glu Thr Gln Phe Asp Ala Lys Gly Thr Pro Phe Ile Ala Gly Lys
    1145                1150                1155
Arg Ile Val Pro Val Ile Glu Asn His Arg Phe Thr Gly Arg Tyr
    1160                1165                1170
Arg Asp Leu Tyr Pro Ala Asn Glu Leu Ile Ala Leu Leu Glu Glu
    1175                1180                1185
Lys Gly Ile Val Phe Arg Asp Gly Ser Asn Ile Leu Pro Lys Leu
    1190                1195                1200
Leu Glu Asn Asp Asp Ser His Ala Ile Asp Thr Met Val Ala Leu
    1205                1210                1215
Ile Arg Ser Val Leu Gln Met Arg Asn Ser Asn Ala Ala Thr Gly
    1220                1225                1230
Glu Asp Tyr Ile Asn Ser Pro Val Arg Asp Leu Asn Gly Val Cys
    1235                1240                1245
Phe Asp Ser Arg Phe Gln Asn Pro Glu Trp Pro Met Asp Ala Asp
    1250                1255                1260
Ala Asn Gly Ala Tyr His Ile Ala Leu Lys Gly Gln Leu Leu Leu
    1265                1270                1275
Asn His Leu Lys Glu Ser Lys Asp Leu Lys Leu Gln Asn Gly Ile
    1280                1285                1290
Ser Asn Gln Asp Trp Leu Ala Tyr Ile Gln Glu Leu Arg Asn
    1295                1300                1305

<210> SEQ ID NO 20
<211> LENGTH: 1228
<212> TYPE: PRT
<213> ORGANISM: Artificial Sequence
<220> FEATURE:
<223> OTHER INFORMATION: Synthetic Sequence

<400> SEQUENCE: 20

Ala Ala Ser Lys Leu Glu Lys Phe Thr Asn Cys Tyr Ser Leu Ser Lys
1               5                   10                  15
Thr Leu Arg Phe Lys Ala Ile Pro Val Gly Lys Thr Gln Glu Asn Ile
                    20                  25                  30
Asp Asn Lys Arg Leu Leu Val Glu Asp Glu Lys Arg Ala Glu Asp Tyr
            35                  40                  45
Lys Gly Val Lys Lys Leu Leu Asp Arg Tyr Tyr Leu Ser Phe Ile Asn
    50                  55                  60
Asp Val Leu His Ser Ile Lys Leu Lys Asn Leu Asn Asn Tyr Ile Ser
65                  70                  75                  80
Leu Phe Arg Lys Lys Thr Arg Thr Glu Lys Glu Asn Lys Glu Leu Glu
                85                  90                  95
Asn Leu Glu Ile Asn Leu Arg Lys Glu Ile Ala Lys Ala Phe Lys Gly
                    100                 105                 110
Ala Ala Gly Tyr Lys Ser Leu Phe Lys Lys Asp Ile Ile Glu Thr Ile
            115                 120                 125
Leu Pro Glu Ala Ala Asp Asp Lys Asp Glu Ile Ala Leu Val Asn Ser
    130                 135                 140
Phe Asn Gly Phe Thr Thr Ala Phe Thr Gly Phe Phe Asp Asn Arg Glu
```

-continued

```
            145                 150                 155                 160
Asn Met Phe Ser Glu Glu Ala Lys Ser Thr Ser Ile Ala Phe Arg Cys
                    165                 170                 175
Ile Asn Glu Asn Leu Thr Arg Tyr Ile Ser Asn Met Asp Ile Phe Glu
                180                 185                 190
Lys Val Asp Ala Ile Phe Asp Lys His Glu Val Gln Glu Ile Lys Glu
            195                 200                 205
Lys Ile Leu Asn Ser Asp Tyr Asp Val Glu Asp Phe Phe Glu Gly Glu
        210                 215                 220
Phe Phe Asn Phe Val Leu Thr Gln Glu Gly Ile Asp Val Tyr Asn Ala
225                 230                 235                 240
Ile Ile Gly Gly Phe Thr Glu Ser Gly Lys Ile Lys Gly Leu
                    245                 250                 255
Asn Glu Tyr Ile Asn Leu Tyr Asn Ala Lys Thr Lys Gln Ala Leu Pro
                260                 265                 270
Lys Phe Lys Pro Leu Tyr Lys Gln Val Leu Ser Asp Arg Glu Ser Leu
            275                 280                 285
Ser Phe Tyr Gly Glu Gly Tyr Thr Ser Asp Glu Glu Val Leu Glu Val
        290                 295                 300
Phe Arg Asn Thr Leu Asn Lys Asn Ser Glu Ile Phe Ser Ser Ile Lys
305                 310                 315                 320
Lys Leu Glu Lys Leu Phe Lys Asn Phe Asp Tyr Ser Ser Ala Gly
                    325                 330                 335
Ile Phe Val Lys Asn Gly Pro Ala Ile Ser Thr Ile Ser Lys Asp Ile
                340                 345                 350
Phe Gly Glu Trp Asn Leu Ile Arg Asp Lys Trp Asn Ala Glu Tyr Asp
            355                 360                 365
Asp Ile His Leu Lys Lys Ala Val Val Thr Glu Lys Tyr Glu Asp
        370                 375                 380
Asp Arg Arg Lys Ser Phe Lys Lys Ile Gly Ser Phe Ser Leu Glu Gln
385                 390                 395                 400
Leu Gln Glu Tyr Ala Asp Ala Asp Leu Ser Val Val Glu Lys Leu Lys
                    405                 410                 415
Glu Ile Ile Ile Gln Lys Val Asp Glu Ile Tyr Lys Val Tyr Gly Ser
                420                 425                 430
Ser Glu Lys Leu Phe Asp Ala Asp Phe Val Leu Glu Lys Ser Leu Lys
            435                 440                 445
Lys Asn Asp Ala Val Val Ala Ile Met Lys Asp Leu Leu Asp Ser Val
        450                 455                 460
Lys Ser Phe Glu Asn Tyr Ile Lys Ala Phe Phe Gly Glu Gly Lys Glu
465                 470                 475                 480
Thr Asn Arg Asp Glu Ser Phe Tyr Gly Asp Phe Val Leu Ala Tyr Asp
                    485                 490                 495
Ile Leu Leu Lys Val Asp His Ile Tyr Asp Ala Ile Arg Asn Tyr Val
                500                 505                 510
Thr Gln Lys Pro Tyr Ser Lys Asp Lys Phe Lys Leu Tyr Phe Gln Asn
            515                 520                 525
Pro Gln Phe Met Gly Gly Trp Asp Lys Asp Lys Glu Thr Asp Tyr Arg
        530                 535                 540
Ala Thr Ile Leu Arg Tyr Gly Ser Lys Tyr Tyr Leu Ala Ile Met Asp
545                 550                 555                 560
Lys Lys Tyr Ala Lys Cys Leu Gln Lys Ile Asp Lys Asp Val Asn
                    565                 570                 575
```

```
Gly Asn Tyr Glu Lys Ile Asn Tyr Lys Leu Leu Pro Gly Pro Asn Lys
            580                 585                 590

Met Leu Pro Lys Val Phe Phe Ser Lys Lys Trp Met Ala Tyr Tyr Asn
            595                 600                 605

Pro Ser Glu Asp Ile Gln Lys Ile Tyr Lys Asn Gly Thr Phe Lys Lys
            610                 615                 620

Gly Asp Met Phe Asn Leu Asn Asp Cys His Lys Leu Ile Asp Phe Phe
625                 630                 635                 640

Lys Asp Ser Ile Ser Arg Tyr Pro Lys Trp Ser Asn Ala Tyr Asp Phe
                645                 650                 655

Asn Phe Ser Glu Thr Glu Lys Tyr Lys Asp Ile Ala Gly Phe Tyr Arg
            660                 665                 670

Glu Val Glu Glu Gln Gly Tyr Lys Val Ser Phe Glu Ser Ala Ser Lys
            675                 680                 685

Lys Glu Val Asp Lys Leu Val Glu Glu Gly Lys Leu Tyr Met Phe Gln
            690                 695                 700

Ile Tyr Asn Lys Asp Phe Ser Asp Lys Ser His Gly Thr Pro Asn Leu
705                 710                 715                 720

His Thr Met Tyr Phe Lys Leu Leu Phe Asp Glu Asn Asn His Gly Gln
                725                 730                 735

Ile Arg Leu Ser Gly Gly Ala Glu Leu Phe Met Arg Arg Ala Ser Leu
            740                 745                 750

Lys Lys Glu Glu Leu Val Val His Pro Ala Asn Ser Pro Ile Ala Asn
            755                 760                 765

Lys Asn Pro Asp Asn Pro Lys Lys Thr Thr Thr Leu Ser Tyr Asp Val
            770                 775                 780

Tyr Lys Asp Lys Arg Phe Ser Glu Asp Gln Tyr Glu Leu His Ile Pro
785                 790                 795                 800

Ile Ala Ile Asn Lys Cys Pro Lys Asn Ile Phe Lys Ile Asn Thr Glu
                805                 810                 815

Val Arg Val Leu Leu Lys His Asp Asp Asn Pro Tyr Val Ile Gly Ile
            820                 825                 830

Asp Arg Gly Glu Arg Asn Leu Leu Tyr Ile Val Val Val Asp Gly Lys
            835                 840                 845

Gly Asn Ile Val Glu Gln Tyr Ser Leu Asn Glu Ile Ile Asn Asn Phe
850                 855                 860

Asn Gly Ile Arg Ile Lys Thr Asp Tyr His Ser Leu Leu Asp Lys Lys
865                 870                 875                 880

Glu Lys Glu Arg Phe Glu Ala Arg Gln Asn Trp Thr Ser Ile Glu Asn
                885                 890                 895

Ile Lys Glu Leu Lys Ala Gly Tyr Ile Ser Gln Val Val His Lys Ile
            900                 905                 910

Cys Glu Leu Val Glu Lys Tyr Asp Ala Val Ile Ala Leu Glu Asp Leu
            915                 920                 925

Asn Ser Gly Phe Lys Asn Ser Arg Val Lys Val Glu Lys Gln Val Tyr
            930                 935                 940

Gln Lys Phe Glu Lys Met Leu Ile Asp Lys Leu Asn Tyr Met Val Asp
945                 950                 955                 960

Lys Lys Ser Asn Pro Cys Ala Thr Gly Gly Ala Leu Lys Gly Tyr Gln
                965                 970                 975

Ile Thr Asn Lys Phe Glu Ser Phe Lys Ser Met Ser Thr Gln Asn Gly
            980                 985                 990
```

| | | | | | | | | | | | | |
|---|---|---|---|---|---|---|---|---|---|---|---|---|
| Phe | Ile | Phe | Tyr | Ile | Pro | Ala | Trp | Leu | Thr | Ser | Lys | Ile | Asp Pro Ser |
| | | 995 | | | | 1000 | | | | | 1005 | | |
| Thr | Gly | Phe | Val | Asn | Leu | Leu | Lys | Thr | Lys | Tyr | Thr | Ser Ile Ala |
| | 1010 | | | | | 1015 | | | | | 1020 | |
| Asp | Ser | Lys | Lys | Phe | Ile | Ser | Ser | Phe | Asp | Arg | Ile | Met Tyr Val |
| | 1025 | | | | | 1030 | | | | | 1035 | |
| Pro | Glu | Glu | Asp | Leu | Phe | Glu | Phe | Ala | Leu | Asp | Tyr | Lys Asn Phe |
| | 1040 | | | | | 1045 | | | | | 1050 | |
| Ser | Arg | Thr | Asp | Ala | Asp | Tyr | Ile | Lys | Lys | Trp | Lys | Leu Tyr Ser |
| | 1055 | | | | | 1060 | | | | | 1065 | |
| Tyr | Gly | Asn | Arg | Ile | Arg | Ile | Phe | Ala | Ala | Ala | Lys | Lys Asn Asn |
| | 1070 | | | | | 1075 | | | | | 1080 | |
| Val | Phe | Ala | Trp | Glu | Glu | Val | Cys | Leu | Thr | Ser | Ala | Tyr Lys Glu |
| | 1085 | | | | | 1090 | | | | | 1095 | |
| Leu | Phe | Asn | Lys | Tyr | Gly | Ile | Asn | Tyr | Gln | Gln | Gly | Asp Ile Arg |
| | 1100 | | | | | 1105 | | | | | 1110 | |
| Ala | Leu | Leu | Cys | Glu | Gln | Ser | Asp | Lys | Ala | Phe | Tyr | Ser Ser Phe |
| | 1115 | | | | | 1120 | | | | | 1125 | |
| Met | Ala | Leu | Met | Ser | Leu | Met | Leu | Gln | Met | Arg | Asn | Ser Ile Thr |
| | 1130 | | | | | 1135 | | | | | 1140 | |
| Gly | Arg | Thr | Asp | Val | Asp | Phe | Leu | Ile | Ser | Pro | Val | Lys Asn Ser |
| | 1145 | | | | | 1150 | | | | | 1155 | |
| Asp | Gly | Ile | Phe | Tyr | Asp | Ser | Arg | Asn | Tyr | Glu | Ala | Gln Glu Asn |
| | 1160 | | | | | 1165 | | | | | 1170 | |
| Ala | Ile | Leu | Pro | Lys | Asn | Ala | Asp | Ala | Asn | Gly | Ala | Tyr Asn Ile |
| | 1175 | | | | | 1180 | | | | | 1185 | |
| Ala | Arg | Lys | Val | Leu | Trp | Ala | Ile | Gly | Gln | Phe | Lys | Lys Ala Glu |
| | 1190 | | | | | 1195 | | | | | 1200 | |
| Asp | Glu | Lys | Leu | Asp | Lys | Val | Lys | Ile | Ala | Ile | Ser | Asn Lys Glu |
| | 1205 | | | | | 1210 | | | | | 1215 | |
| Trp | Leu | Glu | Tyr | Ala | Gln | Thr | Ser | Val | Lys | | | |
| | 1220 | | | | | 1225 | | | | | | |